(12) United States Patent
Popko et al.

(10) Patent No.: US 8,309,790 B2
(45) Date of Patent: *Nov. 13, 2012

(54) ANIMAL MODELS FOR DEMYELINATION DISORDERS

(75) Inventors: Brian Popko, Chicago, IL (US); Wensheng Lin, Chicago, IL (US)

(73) Assignee: University of Chicago, Chicago, IL (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/799,670

(22) Filed: Apr. 28, 2010

(65) Prior Publication Data

US 2010/0281548 A1 Nov. 4, 2010

Related U.S. Application Data

(60) Division of application No. 11/729,242, filed on Mar. 27, 2007, now Pat. No. 7,754,941, which is a continuation of application No. 11/431,372, filed on May 9, 2006, now Pat. No. 7,423,194.

(60) Provisional application No. 60/690,691, filed on Jun. 14, 2005, provisional application No. 60/744,826, filed on Apr. 13, 2006, provisional application No. 60/792,007, filed on Apr. 14, 2006.

(51) Int. Cl.
G01N 33/00 (2006.01)
A01K 67/00 (2006.01)

(52) U.S. Cl. .................. 800/3; 800/9; 435/7.1; 435/325

(58) Field of Classification Search .................. 800/3, 9; 435/7.1, 325
See application file for complete search history.

(56) References Cited

U.S. PATENT DOCUMENTS

| | | | |
|---|---|---|---|
| 5,175,384 A | 12/1992 | Krimpenfort et al. | |
| 5,175,385 A | 12/1992 | Wagner et al. | |
| 5,210,015 A | 5/1993 | Gelfand et al. | |
| 5,445,934 A | 8/1995 | Fodor et al. | |
| 7,306,905 B2 | 12/2007 | Ron et al. | |
| 2002/0116730 A1 | 8/2002 | Allen et al. | |
| 2006/0068496 A1 | 3/2006 | Kelly | |
| 2006/0280685 A1 | 12/2006 | Popko et al. | |
| 2006/0280744 A1 | 12/2006 | Popko et al. | |
| 2006/0282905 A1 | 12/2006 | Popko et al. | |
| 2008/0096202 A1 | 4/2008 | Popko et al. | |
| 2011/0207126 A1 | 8/2011 | Popko et al. | |

OTHER PUBLICATIONS

Agresti, et al. Reversible inhibitory effects of interferon-gamma and tumour necrosis factor-alpha on oligodendroglial lineage cell proliferation and differentiation in vitro. Eur J Neurosci. 1996; 8(6): 1106-16.

Agresti, et al. Synergistic stimulation of MHC class I and IRF-1 gene expression by IFN-gamma and TNF-alpha in oligodendrocytes. Eur J Neurosci. 1998; 10(9): 2975-83.

Alexander, et al. Socs1 is a critical inhibitor of interferon-gamma signaling and prevents the potentially fatal action of the cytokine. Cell. 1999; 98: 597-608.

Andorfer, et al. PKA phosphorylations on tau: developmental studies in the mouse. Dev Neurosci. 2000;22(4):303-9.

Andrews, et al. TNFalpha potentiates IFNgamma-induced cell death in oligodendrocyte progenitors. J Neurosci Res. 1998; 54(5): 574-83.

Aridor, et al. Integration of endoplasmic reticulum signaling in health and disease. Nat Med. Jul. 1999;5(7):745-51.

Armstrong, et al. Endogenous cell repair of chronic demyelination. J Neuropathol Exp Neurol. Mar. 2006;65(3):245-56.

Baerwald, et al. Developing and mature oligodendrocytes respond differently to the immune cytokine interferon-gamma. J. Neurosci Res. 1998; 52(2): 230-9.

Baerwald, et al. Major histocompatibility complex heavy chain accumulation in the endoplasmic reticulum of oligodendrocytes results in myelin abnormalities. J Neurosci Res. 2000; 59(2): 160-9.

Becher, et al. Interferon-gamma secretion by peripheral blood T-cell subsets in multiple sclerosis: correlation with disease phase and interferon-beta therapy. Ann Neurol. 1999; 45(2): 247-50.

Billiau, A. Interferon-γ: biology and role in pathogenesis. Adv Immunol. 1996; 62: 61-130.

Bordignon, et al. Retroviral vector-mediated high-efficiency expression of adenosine deaminase (ADA) in hemtopoietic long-term cultures of ADA-deficient marrow cells. Proc Natl Acad Sci USA. 1989; 86(17): 6748-52.

Boyce, et al. A selective inhibitor of eIF2alpha dephosphorylation protects cells from ER stress. Science. 2005; 307(5711): 935-9.

Brenner, et al. GFAP promoter directs astrocyte-specific expression in transgenic mice. J Neurosci. 1994; 14(3 Pt 1): 1030-7.

Brown, et al. Gene delivery with synthetic (non viral) carriers. Int J Pharm. Oct. 23, 2001;229(1-2):1-21.

Brück, et al. Remyelination in multiple sclerosis. J Neurol Sci. 2003; 206(2): 181-5.

Brummelkamp, et al. A system for stable expression of short interfering RNAs in mammalian cells. Science. 2002; 296(5567): 550-3.

Brummelkamp, et al. Stable suppression of tumorigenicity by virus-mediated RNA interference. Cancer Cell. 2002; 2(3): 243-7.

Brungorg, et al. The cuprizone model for demyelination. Acta Neurol Scand Suppl. 2008;188:72-6.

Bullen, et al. Neutralization of interferon-gamma in neonatal SOCS1–/– mice prevents fatty degeneration of the liver but not subsequent inflammatory disease. Immunol. 2001; 104: 92-8.

Calabresi, et al. Cytokine gene expression in cells derived from CSF of multiple sclerosis patients. J Neuroimmunol. 1998; 89(1-2): 198-205.

Caplen, et al. Specific inhibition of gene expression by small double-stranded RNAs in invertebrate and vertebrate systems. Proc Natl Acad Sci USA. 2001; 98(17): 9742-7.

(Continued)

Primary Examiner — Maria Leavitt
(74) Attorney, Agent, or Firm — Wilson Sonsini Goodrich & Rosati

(57) ABSTRACT

This invention is in the field of neurology. Specifically, the invention relates to the discovery and characterization of molecular components that play a role in neuronal demyelination or remyelination. In addition, the invention relates to the generation of an animal model that exhibits hypomyelination. The compositions and methods embodied in the present invention are particularly useful for drug screening and/or treatment of demyelination disorders.

14 Claims, 37 Drawing Sheets

OTHER PUBLICATIONS

Chakrabarty, et al. Quantifying immunohistochemical staining of phospho-eIF2alpha, heme oxygenase-2 and NADPH cytochrome P450 reductase in oligodendrocytes during experimental autoimmune encephalomyelitis. J Neurosci Methods. 2005; 144(2): 227-34.
Chan-Hui, et al. Applications of eTag assay platform to systems biology approaches in molecular oncology and toxicology studies. Clinical Immunology. 2003; 111(2): 162-74.
Chernajovsky, et al. Gene therapy for autoimmune diseases: quo vadis? Nat Rev Immunol. 2004; 4(10): 800-11.
Chew, et al. Interferon-gamma inhibits cell cycle exit in differentiating oligodendrocyte progenitor cells. Glia. 2005; 52(2): 127-43.
Chong, et al. Gamma-Interferon signaling in pancreatic beta-cells is persistent but can be terminated by overexpression of suppressor of cytokine signaling-1. Diabetes. 2001; 50: 2744-51.
Coetzee, et al. Myelination in the absence of galactocerebroside and sulfatide: normal structure with abnormal function and regional instability. Cell. 1996; 86(2): 209-19.
Compston, et al. Multiple sclerosis. Lancet. Oct. 25, 2008;372(9648):1502-17.
Connor, et al. Growth arrest and DNA damage-inducible protein GADD34 assembles a novel signaling complex containing protein phosphatase 1 and inhibtor 1. Mol Cell Biol. 2001; 21(20): 6841-50.
Corbin, et al. Targeted CNS expression of interferon-gamma in transgenic mice leads to hypomyelination, reactive gliosis, and abnormal cerebellar development. Mol Cell Neurosci. 1996; 7(5): 354-70.
Culver, et al. Lymphocytes as cellular vehicles for gene therapy in mouse and man. Proc Natl Acad Sci USA. 1991; 88(8): 3155-9.
Dell'Albani, et al. Oligodendroglial survival factors, PDGF-AA and CNTF, activate similar JAK/STAT signaling pathways. J Neurosci Res. 1998; 54(2): 191-205.
Dighe, et al. Enhanced in vivo growth and resistance to rejection of tumor cells expressing dominant negative IFN gamma receptors. Immunity. 1994; 1(6): 447-56.
Doerflinger, et al. Inducible site-specific recombination in myelinating cells. Genesis. 2003; 35(1): 63-72.
Economides, et al. Cytokine traps: multi-component, high-affinity blockers of cytokine action. Nat Med. 2003; 9(1): 47-52.
Einhauer, A. et al. The FLAG™ peptide, a versatile fusion tag for the purification of recombinant proteins. J Biochem Biophys Methods. 2001; 49(1-3): 455-65.
Federici, et al. Impaired IFN-gamma-dependent inflammatory response in human keratinocytes overexpressing the suppressor of cytokine signaling 1. J Immunol. 2002; 169(1): 434-43.
Feldhaus, et al. Effects of interferon-gamma and tumor necrosis factor-alpha on survival and differentiation of oligodendrocyte progenitors. J Soc Gynecol Investig. 2004; 11(2): 89-96.
Flodström, et al. Target cell defense prevents development of diabetes after viral infection. Nature Immunol. 2001; 3: 373-82.
Fuss, B. et al. Purification and analysis of in vivo-differentiated oligodendrocytes expressing the green fluorescent protein. Dev Biol. 2000; 218(2): 259-74.
Fuss, et al. Normal CNS myelination in transgenic mice overexpressing MHC class I H-2L(d) in oligodendrocytes. Mol Cell Neurosci. 2001; 18(2): 221-34.
Gao, X. et al. Interferon-γ protects against cuprizone-induced demyelination. Mol Cell Neurosci. 2000; 16(4): 338-49.
Glabinski, et al. Chemokine expression in GRO mice (lacking interferon-gamma) with experimental autoimmune encephalomyelitis. J Neurovirol. 1999; 5(1): 95-101.
Gonzales, J.M. et al. Expression of dominant negative IFN-γ receptor on mouse oligodendrocytes. GLIA. 2005; 51(1): 22-34.
Hammond, et al. Argonaute2, a link between genetic and biochemical analyses of RNAi. Science. 2001; 293(5532): 1146-50.
Harding, et al. Regulated translation initiation controls stress-induced gene expression in mammalian cells. Mol Cell. 2000; 6(5): 1099-108.
Harding, et al. An integrated stress response regulates amino acid metabolism and resistance to oxidative stress. Mol Cell. 2003; 11(3): 619-33.
Harding, et al. Diabetes mellitus and exocrine pancreatic dysfunction in perk-/- mice reveals a role for translational control in secretory cell survival. Mol Cell. 2001; 7(6): 1153-63.
Harding, et al. Protein translation and folding are coupled by an endoplasmic-reticulum-resident kinase. Nature. 1999; 397(6716): 271-4.
Hindinger, C. et al. Astrocyte expression of dominant-negative interferon-gamma receptor. J Neurosci Res. 2005; 82(1): 20-31.
Hisahara, et al. Caspase-11 mediates oligodendrocyte cell death and pathogenesis of autoimmune-mediated demyelination. J Exp Med. 2001; 193(1); 111-22.
Hisahara, et al. Targeted expression of baculovirus p35 caspase inhibitor in oligodendrocytes protects mice against autoimmune-mediated demyelination. EMBO J. 2000; 19(3): 341-8.
Hochepied, et al. Breaking the species barrier: derivation of germline-competent embryonic stem cells from Mus spretus x C57BL/6 hybrids. Stem Cells. 2004;22(4):441-7.
Horwitz, M.S. et al. Primary demyelination in transgenic mice expressing interferon-gamma. Nature Med. 1997; 3(9): 1037-41.
Jiang, et al. Activating transcription factor 3 is integral to the eukaryotic initiation factor 2 kinase stress response. Mol Cell Biol. 2004; 24(3): 1365-77.
Jousse, et al. Inhibition of a constitutive translation initiation factor 2alpha phosphatase, CReP, promotes survival of stressed cells. J Cell Biol. 2003; 163(4): 767-75.
Jurevics, et al. Alterations in metabolism and gene expression in brain regions during cuprizone-induced demyelination and remyelination. J Neurochem. 2002; 82(1): 126-36.
Keirstead, H. Stem cells for the treatment of myelin loss. TRENDS in Neurosci. 2005; 28(12): 677-83.
Kubo, M. et al. Suppressors of cytokine signaling and immunity. Nature Immunol. 2003; 4: 1169-76.
Kunkler, et al. Reactive astrocytosis from excitotoxic injury in hippocampal organ culture parallels that seen in vivo. J Cereb Blood Flow Metab. 1997; 17(1): 26-43.
Laferla, F.M. et al. Regional hypomyelination and dysplasia in transgenic mice with astrocyte-directed expression of interferon-gamma. J Mol Neurosci. 2000; 15(1): 45-59.
Lamkanfi, et al. Caspase-12: an overview. Cell Death Differ. 2004; 11(4): 365-8.
Leegwater, et al. Subunits of the translation initiation factor eIF2B are mutant in leukoencephalopathy with vanishing white matter. Nat Genet. 2001; 29(4): 383-8.
Lees, et al. A little stress is good: IFN-gamma, demyelination, and multiple sclerosis. J Clin Invest. 2007;117(2):297-9.
Li, et al. Generation of purified neural precursors from embryonic stem cells by lineage selection. Curr Biol. 1998; 8(17): 971-4.
Lin, et al. Endoplasmic reticulum stress modulates the response of myelinating oligodendrocytes to the immune cytokine interferon-gamma. J Cell Biol. 2005; 169: 603-12.
Lin, et al. Interferon-gamma induced medulloblastoma in the developing cerebellum. J Neurosci. 2004; 24(45): 10074-83.
Lin, et al. The integrated stress response prevents demyelination by protecting oligodendrocytes against immune-mediated damage. J Clin Invest. 2007;117(2):448-56.
Lin, W. et al. Interferon-gamma inhibits central nervous system remyelination through a process modulated by endoplasmic reticulum stress. Brain. 2006; 129(5): 1306-18.
Loughlin, A.J. et al. Myelination and remyelination of aggregate rat brain cell cultures enriched with macrophages. J Neurosci Res. 1997; 47(4): 384-92.
Lu, et al. Cytoprotection by pre-emptive conditional phosphorylation of translation initiation factor 2. EMBO J. 2004; 23(1): 169-79.
Lucchinetti, et al. Multiple sclerosis: recent developments in neuropathology, pathogenesis, magnetic resonance imaging studies and treatment. Curr Opin Neurol. Jun. 2001;14(3):259-69.
Ma, et al. The unfolding tale of the unfolded protein response. Cell. 2001; 107(7): 827-30.
Maier, et al. Regulation of signal transducer and activator of transcription and suppressor of cytokine-signaling gene expression in the brain of mice with astrocyte-targeted production of interleukin-12 or experimental autoimmune encephalomyelitis. Am J Pathol. 2002; 160: 271-88.

Marciniak, et al. CHOP induces death by promoting protein synthesis and oxidation in the stressed endoplasmic reticulum. Genes Dev. 2004; 18(24): 3066-77.

Matsushima, et al. The neurotoxicant, cuprizone, as a model to study demyelination and remyelination in the central nervous system. Brain Pathol. 2001; 11(1): 107-16. (Abstract).

Meraz, et al. Targeted disruption of Stat1 gene in mice reveals unexpected physiologic specificity in the JAK-STAT signaling pathway. Cell. 1996; 84: 431-42.

Merrill, J.E. et al. Microglial cell cytotoxicity of oligodendrocytes is mediated through nitric oxide. J Immunol, 1993; 151(4): 2132-41.

Merrill, J.E. et al. Natural and induced cytotoxicity of oligodendrocytes by microglia is inhibitable by TGFβ. GLIA. 1991; 4(3): 327-31.

Miller, et al. Improved retroviral vectors for gene transfer and expression. Biotechniques. 1989; 7(9): 980-90.

Moldovan, I.R. et al. Interferon gamma responses to myelin peptides in multiple sclerosis correlate with a new clinical measure of disease progression. J Neuroimmunol. 2003; 141(1-2): 132-40.

Morris, et al. Immunoglobulin binding protein (BiP) function is required to protect cells from endoplasmic reticulum stress but is not required for the secretion of selective proteins. J Biol Chem. 1997; 272(7): 4327-34.

Muhl, et al. Anti-inflammatory properties of pro-inflammatory interferon-gamma. Int Immunopharmacol. 2005; 3(9): 1247-55.

Nakagawa, et al. Caspase-12 mediates endoplasmic-reticulum-specific apoptosis and cytotoxicity by amyloid-beta. Nature. 2000; 403(6765): 98-103.

Novoa, et al. Feedback inhibition of the unfolded protein response by GADD34-mediated dephosphorylation of eIF2alpha. J Cell Biol. 2001; 153(5): 1011-22.

Paddison, et al. Short hairpin RNAs (shRNAs) induce sequence-specific silencing in mammalian cells. Genes Dev. 2002; 16(8): 948-58.

Panitch, H. Interferons in multiple sclerosis. A review of the evidence. Drugs. 1992; 44(6): 946-62.

Panitch, H.S. etal. Exacerbations of multiple sclerosis in patients treated with gamma interferon. Lancet. 1987; 1(8538): 893-5.

Polizzotto, M.N. et al. Expression of "suppressor of cytokine signaling" (SOCS) genes in the developing and adult mouse nervous system. J Compar Neurol. 2000; 423(2): 348-58.

Popko, et al. Oligodendroglial response to the immune cytokine interferon gama. Neurochem Res. 1999; 24(2): 331-8.

Popko, et al. The effects of interferon-gamma on the central nervous system. *Mol. Neurobiol*. 1997; 14: 19-35.

Pouly, S. et al. Interferon-gamma modulates human oligodendrocyte susceptibility to Fas-mediated injury. J Neuropathol Exp Neurol. 2000; 59(4): 280-6.

Proud, C. eIF2 and the control of cell physiology. Semin Cell Dev Biol. 2005; 16(1): 3-12.

Rao, et al. Coupling endoplasmic reticulum stress to the cell death program. Cell Death Differ. 2004; 11(4): 372-80.

Rill, et al. An approach for the analysis of relapse and marrow reconstitution after autolgous marrow transplantation using retrovirus-mediated gene transfer. Blood. 1992; 79(10): 2688-93.

Rutkowski, et al. A trip to the ER: coping with stress. Trends Cell Biol. 2004; 14(1): 20-8.

Schoonjans, et al. Improved generation of germline-competent embryonic stem cell lines from inbred mouse strains. Stem Cells. 2003;21(1):90-7.

Scientific Considerations Related to Developing Follow-On Protein Products. Division of Dockets Management U.S. Food and Drug Administration. Nov. 12, 2004; pp. 1-12.

Skurkovich, et al. Randomized study of antibodies to IFN-gamma and TNF-alpha in secondary progressive multiple sclerosis. Mult Scler. 2001; 7(5): 277-84.

Song, et al. The suppressor of cytokine signaling (SOCS1) and SOSC3 but not SOCS2 proteins inhibit interferon-mediated antiviral and antiproliferative activities. J Biol Chem. 1998; 273(52): 35056-62.

Southwood, et al. The unfolded protein response modulates disease severity in Pelizaeus-Merzbacher disease. Neuron. 2002; 36(4): 585-96.

Srivastava, et al. Phosphorylation of eukaryotic translation initiation factor 2 mediates apoptosis in response to activation of the double-stranded RNA-dependent protein kinase. J Biol Chem. Jan. 23, 1998;273(4):2416-23.

Stark, G.R. et al. How cells respond to interferons. Ann Rev Biochem. 1998; 67: 227-64.

Starr, et al. Liver degeneration and lymphoid deficiency in mice lacking suppressor of cytokine signaling-1. PNAS USA. 1998; 95: 14395-9.

Starr, R. et al. A family of cytokine inducible inhibitors of signalling. Nature. 1997; 387(6636): 917-21.

Steinman, et al. Virtues and pitfalls of EAE for the development of therapies for multiple sclerosis. Trends Immunol. Nov. 2005;26(11):565-71.

Svendsen, et al. New prospects for human stem-cell therapy in the nervous system. Trends Neurosci. 1999; 22(8): 357-64.

Tassabehji, M. Williams-Beuren syndrome: a challenge for genotype-phenotype correlations. Hum Mol Genet. Oct. 15, 2003;12 Spec No. 2:R229-37.

Torres, et al. Expression of interferon-gamma receptors on murine oligodendrocytes and its regulation by cytokines and mitogens. Immunology. 1995; 86(2): 250-5.

Tran, et al. IFN-gamma shapes immune invasion of the central nervous system via regulation of chemokines. J Immunol. 2000; 164: 2759-68.

Traugott, U. Evidence for immunopathogenesis. In: Handbook of Multiple Sclerosis, 3rd Edition. Cook, S, ed. New York, NY: Marcel Deker, 2001: 157-185.

Turnley, A.M. et al. Failure of sensory neurons to express class I MHC is due to differential SOCS1 expression. Journal of Neuroimmunology. 2002; 123(1-2): 35-40.

Turnley, A.M. et al. SOCS1 regulates interferon-gamma mediated sensory neuron survival. Neuroreport. 2001; 16: 3443-5.

Vartanian, et al. Interferon-γ induced oligodendrocyte cell death: implications for the pathogenesis of multiple sclerosis. Mol Med. 1996; 1(7): 732-43.

Wang, et al. Cytokine signaling in the brain: putting a SOCS in it? J Neurosci Res. 2002; 67: 423-7.

Watson, et al. (Recombinant DNA, Second Edition. 2001, pp. 153-154.).

Wight, et al. A myelin proteolipid protein-lacZ fusion protein is developmentally regulated and targeted to the myelin membrane in transgenic mice. J Cell Biol. 1993; 123(2): 443-54.

Wu, et al. Receptor-mediated in vitro gene transformation by a soluble DNA carrier system. J Biol Chem. 1987; 262(10): 4429-32.

Yasukawa, et al. Negative regulation of cytokine signaling pathways. Annu Rev Immunol. 2000; 18: 143-64.

Zabner, et al. Cellular and molecular barriers to gene transfer by a cationic lipid. J Biol Chem. Aug. 11, 1995;270(32):18997-9007.

International search report dated Jun. 12, 2007 for PCT Application No. US06/23215.

Chakrabarty, et al. Immunohistochemical localization of phoshorylated protein kinase R and phosphorylated eukaryotic initiation factor-2 alpha in the central nervous system of SJL mice with experimental allergic encephalomyelitis. J Neurosci Res. 2004; 76(6): 822-33.

Correll, et al. Production of human glucocerebrosidase in mice after retroviral gene transfer into multipotential hematopoietic progenitor cells. Proc Natl Acad Sci USA. 1989; 86(22): 8912-6.

Gao, X. et al. Advanced transgenic and gene-targeting approaches. Neurochem Res. 1999; 24(9): 1181-1188.

Levy, et al. STATs: transcriptional control and biological impact. Nature Rev Mol Cell Biol. 2002; 3: 651-62.

Nanua, et al., abstract Loss of PERK Signaling Results in Impaired Granulopoiesis in Transgenic Mice Expressing Mutant Ela2.Blood, (Nov. 20, 2009) vol. 114, No. 22, pp. 230.

Novoa, et al. Stress-induced gene expression requires programmed recovery from translational repression. EMBO J. 2003; 22(5): 1180-7.

Sakamoto, H. et al. The janus kinase inhibitor, JAB/SOCS-1, is an interferon-gamma inducible gene and determines the sensitivity to interferons. Leuk Lymphoma. 2000; 38(1-2): 49-58.

Steinman, L. Blockade of gamma interferon might be beneficial in MS. Mult Scler. 2001; 7(5): 275-6.

Wang, et al. The unfolded protein response in familial amyotrophic lateral sclerosis. Hum Mol Genet. Mar. 1, 2011;20(5):1008-15. Epub Dec. 15, 2010.

A

B

ANIMAL MODELS FOR DEMYELINATION DISORDERS

CROSS-REFERENCE

This application is a division of U.S. patent application Ser. No. 11/729,242, filed Mar. 27, 2007, now U.S. Pat. No. 7,754,941, which is a continuation of U.S. patent application Ser. No. 11/431,372, filed May 9, 2006, now U.S. Pat. No. 7,423,194, which claims the benefit of U.S. Provisional Application No. 60/690,691, filed Jun. 14, 2005, U.S. Provisional Application No. 60/744,826, filed Apr. 13, 2006, and U.S. Provisional Application No. 60/792,007, filed Apr. 14, 2006, all of which are incorporated herein by reference in their entirety.

STATEMENT AS TO FEDERALLY SPONSORED RESEARCH

This invention was made with the support of the United States government under Grant Number ROI NS034939 awarded by the National Institute of Health. The government has certain rights in the invention.

SEQUENCE LISTING

The instant application contains a Sequence Listing which has been submitted via EFS-Web and is hereby incorporated by reference in its entirety. Said ASCII copy, created on Jul. 6, 2010, is named 28890401.txt and is 13,287 bytes in size.

TECHNICAL FIELD

This invention is in the field of neurology. Specifically, the invention relates to the discovery and characterization of molecular components that play a role in neuronal demyelination or remyelination. In addition, the invention relates to the generation of an animal model that exhibits hypomyelination. The compositions and methods embodied in the present invention are particularly useful for drug screening and/or treatment of demyelination disorders.

BACKGROUND OF THE INVENTION

Neuronal demyelination is a deleterious condition characterized by a reduction of myelin protein in the nervous system. Myelin is a vital component of the central (CNS) and peripheral (PNS) nervous system, which encases the axons of neurons and forms an insulating layer known as the myelin sheath. The presence of the myelin sheath enhances the speed and integrity of nerve signal in form of electric potential propagating down the neural axon. The loss of myelin sheath produces significant impairment in sensory, motor and other types of functioning as nerve signals reach their targets either too slowly, asynchronously (for example, when some axons in a nerve conduct faster than others), intermittently (for example, when conduction is impaired only at high frequencies), or not at all.

The myelin sheath is formed by the plasma membrane, or plasmalemma, of glial cells—oligodendrocytes in the CNS, and Schwann cells in the PNS. During the active phase of myelination, each oligodendrocyte in the CNS must produce as much as approximately 5000 $\mu m^2$ of myelin surface area per day and approximately $10^5$ myelin protein molecules per minute (Pfeiffer, et al. (1993) Trends Cell Biol. 3: 191-197). Myelinating oligodendrocytes have been identified at demyelinated lesions, indicating that demyelinated axons may be repaired with the newly synthesized myelin.

Neuronal demyelination is manifested in a large number of hereditary and acquired disorders of the CNS and PNS. These disorders include Multiple Sclerosis (MS), Progressive Multifocal Leukoencephalopathy (PML), Encephalomyelitis, Central Pontine Myelolysis (CPM), Anti-MAG Disease, Leukodystrophies: Adrenoleukodystrophy (ALD), Alexander's Disease, Canavan Disease, Krabbe Disease, Metachromatic Leukodystrophy (MLD), Pelizaeus-Merzbacher Disease, Refsum Disease, Cockayne Syndrome, Van der Knapp Syndrome, and Zellweger Syndrome, Guillain-Barre Syndrome (GBS), chronic inflammatory demyelinating polyneuropathy (CIDP), multifocual motor neuropathy (MMN), Alzheimer's disease and progressive supernuclear palsy. For many of these disorders, there are no cures and few effective therapies.

Multiple sclerosis is the most common demyelinating disease of the central nervous system, affecting approximately 1,000,000 people worldwide and some 250,000 to 350,000 people in the United States. The disease is characterized clinically by relapses and remissions, and leading eventually to chronic disability. The earlier phase of multiple sclerosis is characterized by the autoimmune inflammatory strike against myelin sheath leading to paralysis, lack of coordination, sensory disturbances and visual impairment. The subsequent chronic progressive phase of the disease is typically due to active degeneration of the myelin sheath and inadequate remyelination of the demyelinated lesions (Franklin (2002) Nat. Rev. Neurosci. 3: 705-714; Bruck, et at (2003) J. Neurol. Sci. 206: 181-185; Compston, et al. (2002) Lancet 359: 1221-1231).

The precise etiology and pathogenesis of this disease remain unknown. However, pathologic, genetic, and immunologic features have been identified which suggest that the disease involves inflammatory and autoimmune basis. See, for example Waksman, et al. (1984) Proc. Soc. Exp. Biol. Med. 175:282-294; Hafler et al. (1987) Immunol. Rev. 100: 307-332. It is now known that pleotropic cytokine interferon-γ (IFN-γ) which is secreted by activated T Lymphocytes and natural killer cells, plays a deleterious role in immune-mediated demyelinating disorders including MS and experimental allergic encephalomyelitis (EAE) (Popko et al. (1997) Mol. Neurobiol. 14:19-35; Popko and Baerwald (1999) Neurochem. Res. 24:331-338; Steinman (2001a) Mult. Scler. 7:275-276). This cytokine is normally absent in the CNS, and becomes detectable during the symptomatic phase of these disorders (Panitch (1992) Drugs 44:946-962). In vitro studies have shown that IFN-γ is capable of promoting apoptosis in purified developing oligodendrocytes (Baerwald and Popko (1998) J. NeuroSci. Res. 52:230-239; Andrews et al. (1998) J. Neurosci. Res. 54:574-583; Feldhaus et al. (2004) J. Soc. Gynecol. Investig. 11:89-96). Despite these extensive studies, the precise mechanism by which the secretion of IFN-γ leads to oligodendroglial abnormalities and alteration to the myelin sheath is not well understood.

There thus remains a considerable need for compositions and methods applicable for elucidating the molecular bases of neuronal demyelination. There also exists a pressing need for developing biologically active agents effective in treating demyelination disorders.

SUMMARY OF THE INVENTION

The present invention provides a method of developing a biologically active agent that reduces neuronal demyelination. The method involves the steps of (a) contacting a candidate agent with a myelinating cell; (b) detecting an altered expression of a gene or gene product or an altered activity of said gene product relative to a control cell, said gene or gene product being correlated with endoplasmic reticulum (ER) stress; and (c) selecting said agent as a candidate if the level of expression of said gene or gene product, or the level of activity of said gene product is modulated relative to said control cell.

The present invention also provides a method of developing a biologically active agent that promotes neuronal remyelination. The method comprises (a) contacting a candidate biologically active agent with a myelinating cell from a demyelinated lesion of a subject; and (b) detecting an altered expression of a gene or gene product or an altered activity of said gene product relative to a control cell, said gene or gene product being correlated with endoplasmic reticulum (ER) stress; and (c) selecting said agent as a candidate if the level of expression of said gene or gene product, or the level of activity of said gene product is modulated relative to said control cell.

The present invention further provides a method of testing for a biologically active agent that modulates a phenomenon associated with a demyelination disorder. Such method involves (a) administering a candidate agent to a non-human transgenic animal, wherein demyelination occurs in said animal upon expression of said INF-γ; and (b) determining the effect of said agent upon a phenomenon associated with a demyelination disorder.

Also provided in the present invention is a method of testing for a biologically active agent that modulates a phenomenon associated with a demyelination disorder, by performing the following steps: (a) contacting a candidate agent with a cell derived from a non-human transgenic animal; (b) detecting an altered expression of a gene or gene product or an altered activity of said gene product relative to a control cell, said gene or gene product being correlated with endoplasmic reticulum (ER) stress; and (c) selecting the agent as effective to modulate a phenomenon associated with demyelination disorder if the level of expression of said gene or gene product, or the level of activity of said gene product is modulated relative to said control cell.

The present invention provides another method for testing for a biologically active agent that modulates a phenomenon associated with a demyelination disorder. The method involves the steps of: (a) administering a candidate biologically active agent to a test animal generated by a method comprising (i) inducing neuronal demyelination in said test animal, and (ii) allowing said test animal to recover from the demyelination induction for a sufficient amount of time so that remyelination of a demyelinated lesion is exhibited; and (b) determining the effect of said agent upon a phenomenon associated with a demyelination disorder.

In various embodiments of the present invention, the phenomenon associated with a demyelination disorder is characterized by a loss of oligodendrocytes in the central nervous system or Schwann cells in the peripheral nervous system. In other embodiments, the phenomenon associated with a demyelination disorder is characterized by a decrease in myelinated axons in the central nervous system or peripheral nervous system. In yet other embodiments, phenomenon associated with a demyelination disorder is characterized by a reduction in the levels oligodendrocytes or Schwann cell markers, preferably proteinaceous markes. Non-limiting exemplary marker protein of a myelinating cell (including oligodendrocyte and Schwann cell) is selected from the group consisting of CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide and proteolipid protein (PLP). MPZ, PMP22 and P2 are preferred markers for Schwann cells.

In certain embodiments, the demyelination disorder referred therein is multiple sclerosis. In other embodiments, the demyelination disorder is selected from the group consisting of Progressive Multifocal Leukoencephalopathy (PML), Encephalomyelitis, Central Pontine Myelolysis (CPM), Anti-MAG Disease, Leukodystrophies: Adrenoleukodystrophy (ALD), Alexander's Disease, Canavan Disease, Krabbe Disease, Metachromatic Leukodystrophy (MLD), Pelizaeus-Merzbacher Disease, Refsum Disease, Cockayne Syndrome, Van der Knapp Syndrome, and Zellweger Syndrome, Guillain-Barre Syndrome (GBS), chronic inflammatory demyelinating polyneuropathy (CIDP), multifocal motor neuropathy (NON), Alzheimer's disease and progressive supernuclear palsy.

In one aspect of the present invention, the biologically active agent employed in the cell-based assays may be selected from the group consisting of biological or chemical compound such as a simple or complex organic or inorganic molecule, peptide, peptide mimetic, protein (e.g. antibody), liposome, small interfering RNA, or a polynucleotide (e.g. anti-sense).

The present invention also provides a non-human transgenic animal having: (a) stably integrated into the genome of said animal a transgenic nucleotide sequence encoding interferon-gamma (INF-γ); and (b) an altered expression of at least one other gene; wherein upon expression of said INF-γ, said animal exhibits a greater degree of demyelination relative to a transgenic animal having a stably integrated transgenic nucleotide sequence encoding interferon-gamma (INF-γ) as in (a), but lacking said altered expression of said at least one other gene.

In one aspect, the at least one other gene is correlated with endoplasmic reticulum stress. Such genes include but are not limited to pancreatic ER kinase gene (p-PERK), eukaryotic translation initiation factor 2 alpha (eIF-2α, eukaryotic translation initiation factor beta (eIF-2α, inositol requiring 1 (IRE1), activating transcription factor 6 (ARTF6), CAATT enhancer-binding protein homologous protein (CHOP), binding-immunoglobulin protein (BIP), caspase-12, growth and DNA damage protein 34 (GADD34), CreP (a constitutive repressor of eIF2alpha phosphorylation), suppressor of cytokine signaling 1 (SOCS1), and X-box-binding protein-1 (XBP-1).

In another aspect, the non-human transgenic animal comprises a heterozygous knock-out of pancreatic ER kinase gene (PERK), and stably integrated into the genome of said animal a transgenic nucleotide sequence comprising interferon-gamma (INF-γ).

In yet another aspect, the animal exhibits an increased vulnerability to INF-γ-mediated neuronal demyelination relative to a wildtype animal.

Cells derived from such the subject transgenic animals are also provided.

Also included in the present invention is a method of inhibiting neuronal demyelination in a subject comprising administering to said subject an amount of biologically active agent effective to modulate stress level of endoplasmic reticulum (ER) in a myelinating cell, in the perheral or in the central nervous system. The myelinating cell can be an oligodendrocyte or a Schwann cell. In one aspect of this embodiment, the biologically active agent is effective to reduce a sustained stress level of endoplasmic reticulum (ER) in a myelinating cell. In some aspects, the biologically active agent is an interferon-gamma (INF-γ) antagonist with the proviso that said interferon-gamma (INF-γ) antagonist is not an anti-INF-γ antibody when applied after the onset of neuronal demyelination. In other aspects, the biologically active agent is an interferon-gamma (INF-γ) or interferon-gamma (INF-γ) agonist administered prior to the onset of neuronal demyelination to yield a prophylactic effect. Where desired, the biologically active agent can be characterized by the ability to reduce a sustained stress level of ER, which in turn can be characterized by a decrease in the levels of proteins correlated with endoplasmic reticulum (ER) stress. Exemplary ER stress correlated proteins include but are not limited to phosphorylated pancreatic ER kinase gene (p-PERK), eukaryotic translation initiation factor 2 alpha (eIF-2α), eukaryotic translation initiation factor beta (eIF-2β), inositol requiring 1 (IRE 1), activating transcription factor 6 (ARTF6), CAATT enhancer-binding protein homologous protein (CHOP), binding-immunoglobulin protein (BIP), caspase-12, growth and DNA damage protein 34 (GADD34), CreP (a constitutive repressor of eIF2alpha phosphorylation), and X-box-binding protein-1 (XBP-1).

Further provided in the invention is a method of promoting remyelination of a neuron in a subject after an occurrence of neuronal demyelination, comprising administering to said subject an amount of pharmaceutical agent effective to modulate stress level of endoplasmic reticulum (ER) in neuronal tissues undergoing remyelination. In one aspect, the contemplated biologically active agent is an INF-γ antagonist, including but not limited to anti-INF-γ antibody or an antigen-binding fragment thereof. In another aspect, the biologically active agent is effective to reduce a sustained stress level of endoplasmic reticulum (ER) in a myelinating cell. In another aspect, the biologically active agent is effective to activate eIF-2α pathway by increasing eIF-2α kinase activity or increasing the level of phosphorylated eIF-2α present in a cell. In yet another aspect, the biologically active agent is effective to activate eIF-2α pathway by increasing PERK kinase activity or increasing the level of phosphorylated PERK or PERK dimer present in a cell. In still yet another aspect, the biologically active agent is effective to activate eIF-2α pathway by deactivating GADD34 pathway. In some instances, the deactivation of the GADD34 pathway results in reduced GADD34 signaling. In other instances, the deactivation of GADD34 pathway results in a reduction of PPI (protein phosphatase 1) phosphatase activity or a reduction in the level of PPI present in a cell.

The present invention further provides a method of ameliorating progression of a demyelination disorder in a subject in need for such treatment. The method comprises reducing in said subject the level of interferon-gamma (INF-γ) present in said subject's neuronal tissues that are undergoing remyelination or INF-γ signaling. In some instances, the reduction of the level of INF-γ is effected by delivering to a demyelinated lesion an amount of a pharmaceutical composition comprised of interferon-gamma (INF-γ) antagonist (e.g., an anti-INF-γ antibody or an antigen-binding fragment). In another aspect, a reduction in INF-γ signaling is effected by a reduction in the level of a downstream signaling molecule of INF-γ or biological activity thereof. The downstream signaling molecule of INF-γ comprises SOCS1 and/or Stat1.

DETAILED DESCRIPTION OF THE EMBODIMENTS

Figure 1:
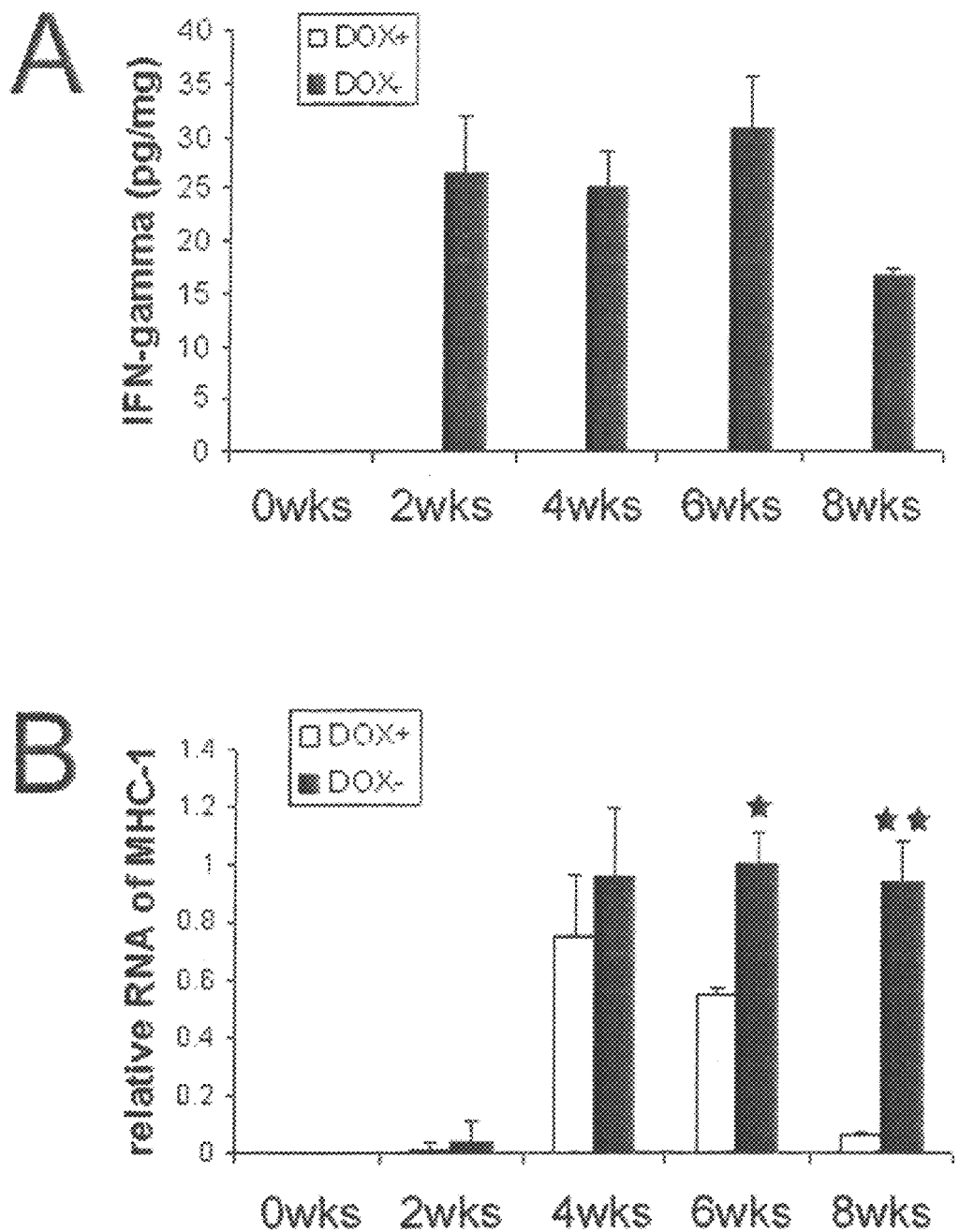
FIG. 1 depicts the results of ELISA analysis of IFN-γ expression pattern in double transgenic mice (GFAP/tTA, TRE/IFN-γ). (A) ELISA analysis of the expression of IFN-γ protein in the forebrain of double transgenic mice treated with cuprizone (n=2). (B) Real-time PCR analysis of the expression of MHC-I in the corpus callosum of double transgenic mice treated with cuprizone, n=3, *p<0.05, **p<0.01.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

General Techniques:

The practice of the present invention employs, unless otherwise indicated, conventional techniques of immunology, biochemistry, chemistry, molecular biology, microbiology, cell biology, genomics and recombinant DNA, which are within the skill of the'art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

DEFINITIONS

As used in the specification and claims, the singular form "a", "an" and "the" include plural references unless the context clearly dictates otherwise. For example, the term "a cell" includes a plurality of cells, including mixtures thereof.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" or "probe" refers to a polynucleotide used for detecting or identifying its corresponding target polynucleotide in a hybridization reaction.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product." If the polynucleotide is derived from genomic DNA, expression may include splicing of the mRNA in a eukaryotic cell.

"Differentially expressed," as applied to nucleotide sequence or polypeptide sequence in a subject, refers to overexpression or under-expression of that sequence when compared to that detected in a control. Underexpression also encompasses absence of expression of a particular sequence as evidenced by the absence of detectable expression in a test subject when compared to a control.

"Signal transduction" is a process during which stimulatory or inhibitory signals are transmitted into and within a cell to elicit an intracellular response. A molecule can mediate its signaling effect via direct or indirect interact with downstream molecules of the same pathway or related pathway(s). For instance, INFγ signaling can involve a host of downstream molecules including but not limited to one or more of the following proteins: PERK, eIF-2α, SOCS1, and Stat1.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

As used herein, "myelinating cell" refers to those cells capable of producing myelin which insulates axons in the nervous system. Exemplary myelinating cells are oligodendrocytes responsible for producing myelin in the central nervous system, and Schwann cells responsible for producing myelin in the peripheral nervous system.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

A "control" is an alternative subject or sample used in an experiment for comparison purpose.

A central aspect of the present invention is the discovery of the association of neuronal demyelination with endoplasmic reticulum (ER) stress level in cells that play a role in neuronal myelination.

Cell-Based Assays:

Accordingly, in one embodiment, the present invention provides method of developing a biologically active agent that reduces neuronal demyelination. The method involves the steps of (a) contacting a candidate agent with a myelinating cell; (b) detecting an altered expression of a gene or gene product or an altered activity of said gene product relative to a control cell, said gene or gene product being correlated with endoplasmic reticulum (ER) stress; and (c) selecting said agent as a candidate if the level of expression of said gene or gene product, or the level of activity of said gene product is modulated relative to said control cell.

In another embodiment, the present invention provides a method of developing a biologically active agent that promotes neuronal remyelination. The method comprises the steps of (a) contacting a candidate biologically active agent with a myelinating cell from a demyelinated lesion of a subject; and (b) detecting an altered expression of a gene or gene product or an altered activity of said gene product relative to a control cell, said gene or gene product being correlated with endoplasmic reticulum (ER) stress; and (c) selecting said agent as a candidate if the level of expression of said gene or gene product, or the level of activity of said gene product is modulated relative to said control cell.

The practice of the invention involves a comparison of the expression of a gene or gene product or the activity of said gene product in a test myelinating cell (whether oligodendrocyte or Schwann cell) relative to a control cell. The test myelinating cell used for this invention can be isolated from central or peripheral nervous systems, and includes cell culture derived therefrom and the progeny thereof, and section or smear prepared from the source, or any other samples of the brain that contain oligodendrocytes or Schwann cells or their progenitors. Where desired, one may choose to use enriched these cell cultures that are substantially free of other neuronal cell types such as neurons, microglial cells, and astrocytes.

Various methods of isolating, generating or maintaining matured oligodendrocytes and Schwann cells are known in the art (Baerwald, et al. (1998) *J. Neurosci. Res.* 52: 230-239; Levi, et al. (1996) *J Neurosci Methods.* 68(1): 21-6) and are exemplified herein.

In certain embodiments, it may be preferable to employ myelinating cells from young subjects whose nervous systems are actively undergoing myelination. In other embodiments, it may be preferable to use remyelinating cells derived from adult oligodendrocyte precursors in demyelinated lesions, including but not limited to lesions inflicted by pathogens or physical injuries, and lesions caused by toxic agents such as cuprizone. In yet other embodiments, it may be preferable to use myelinating cells that are directly exposed to IFN-γ or that are derived from subjects whose nervous systems have been exposed to IFN-γ. For instance, one may choose to employ oligodendrocytes derived from transgenic animals that are ectopically expressed IFN-γ in the central nervous systems. In still other embodiments, one may select test myelinating cells that differentially express any ER-stress related genes. Such myelinating cells may overexpress or underexpress ER-stress causing genes, or ER-stress suppressing genes (e.g., BIP, and pancreatic ER kinase gene (PERK)). These myelinating cells may be derived from transgenic animals that have one or more ER-stress related genes knocked-in (overexpress) or knocked-out (underexpress).

Alternatively, such myelinating cells can be generated by introducing into the cell a genetic vehicle to effect such overexpression or underexpression. A vast number of genetic vehicles suitable for the present invention are available in the art. They include both viral and non-viral expression vectors. Non-limiting exemplary viral expression vectors are vectors derived from RNA viruses such as retroviruses, and DNA viruses such as adenoviruses and adeno-associated viruses. Non-viral expression vectors include but are not limited to plasmids, cosmids, and DNA/liposome complexes. Where desired, the genetic vehicles can be engineered to carry regulatory sequences that direct tissue specific, cell specific, or even organelle specific expression of the exogenous genes carried therein.

A number of tissue or cell specific regulatory sequences have been demonstrated applicable for expressing transgenes in the central nervous systems and peripheral nervous system. An exemplary sequence is the transcriptional regulatory sequence of the glial fibrillary acidic gene (GFAP). The regulatory sequence allows ectopical expression of transgenes in the central nervous system and peripheral nervous system (e.g., in the Schwann cells).

A wide variety of subcellular localization sequences have been characterized and are applicable for directing organelle specific expression of transgenes. For instance, subcellular localization sequence can be any one of the following: (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence) that confines the encoded protein primarily to the ER; or (e) any other sequences that play a role in differential subcellular distribution of a encoded protein product.

The genetic vehicles can be inserted into a host cell (e.g., myelinating cells such as oligodendrocytes or Schwann cells) by any methods known in the art. Suitable methods may include transfection using calcium phosphate precipitation, DEAE-dextran, electroporation, or microinjection.

The selection of an appropriate control cell or tissue is dependent on the test cell or tissue initially selected and its phenotypic or genotypic characteristic which is under investigation. Whereas the test myelinating cell is derived from demyelinated lesions, one or more counterparts from non-demyelinated tissues can be used as control cells. Whereas the test myelinating cell is treated with IFN-γ, the control cell may be a non-treated counterpart. It is generally preferable to analyze the test cell and the control in parallel.

For the purposes of this invention, a biologically active agent effective to modulate neuronal demyelination is intended to include, but not be limited to a biological or chemical compound such as a simple or complex organic or inorganic molecule, peptide, peptide mimetic, protein (e.g. antibody), liposome, small interfering RNA, or a polynucleotide (e.g. anti-sense). A class of preferred agents include those that block the downstream signaling effect of a target molecule. This class of agents may include soluble ligand receptors or derivatives thereof that compete for the binding of the ligands with the native receptors, typically anchored on the cell, thereby preventing the ligands from mediating their downstream effect. The methodology is known in the art. See, e.g., Economides et al. (2003) Nat Med 9(1):47-52.

A vast array of compounds can be synthesized, for example polymers, such as polypeptides and polynucleotides, and synthetic organic compounds based on various core structures, and these are also contemplated herein. In addition, various natural sources can provide compounds for screening, such as plant or animal extracts, and the like. It should be understood, although not always explicitly stated that the active agent can be used alone or in combination with another modulator, having the same or different biological activity as the agents identified by the subject screening method. A preferred class of agent is IFN-γ antagonist. As is understood by one skilled in the art, an antagonist inhibits the biological activity mediated by a target that it interacts. An antagonist can assert its inhibitory effect by directly binding to or directly interacting with the target. An antagonist can also assert its inhibitory effect indirectly by first interacting with a molecule in the same signaling pathway. The IFN-γ antagonist of the present invention encompasses simple or complex organic or inorganic molecule, peptide, peptide mimetic, protein (e.g. antibody), liposome, small interfering RNA, or a polynucleotide (e.g. anti-sense) that can reduce the deleterious effect of IFN-γ on neuronal demyelination.

In some instances where prophylactic effect is desired, IFN-γ or IFN-γ agonist (e.g., salubrinol (Sal)) can be applied prior to the onset of neuronal demyelination. As is understood by one skilled in the art, an agonist activates the biological activity mediated by a target that it interacts. An agonist can assert its inhibitory effect by directly binding to or directly interacting with the target. An agonist can also assert its stimulatory effect indirectly by first interacting with a molecule in the same signaling pathway. The IFN-γ agonist of the present invention encompasses simple or complex organic or inorganic molecule, peptide, peptide mimetic, protein (e.g. antibody), liposome, small interfering RNA, or a polynucleotide (e.g. anti-sense) that can reduce the deleterious effect of IFN-γ on neuronal demyelination.

When the agent is a composition other than naked RNA, the agent may be directly added to the cell culture or added to culture medium for addition. As is apparent to those skilled in the art, an "effective" amount must be added which can be empirically determined. When the agent is a polynucleotide, it may be introduced directly into a cell by transfection or electroporation. Alternatively, it may be inserted into the cell using a gene delivery vehicle or other methods as described above.

As used herein, ER-stress related genes encompass all nucleic acids encoding proteins that correlate with stress in the ER. Generally, these proteins play a role in ER homeostasis. There are many ways in which stress, whether endogenous or exogenous, that can be manifested in a cell; these include but are not limited to pathogenic infection, chemical insult, genetic mutation, nutrient deprivation, and even normal cellular differentiation.

In general, disruption of the homeostasis and hence ER stress is evidenced by the accumulation of unfolded or misfolded proteins in the ER lumen (Rutkowski, et al. (2004) *Trends Cell Biol.* 14: 20-28; Ma, et al. (2001) *Cell* 107: 827-830). This stress elicits the unfolded protein response, a functional mechanism by which cells attempt to protect themselves against ER stress. The unfolded protein response may involve 1) transcriptional induction of ER chaperone proteins whose function is both to increase folding capacity of the ER and prevent protein aggregation; 2) translational attenuation to reduce protein overload and subsequent accumulation of unfolded proteins; and 3) removal of misfolded proteins from the ER through retrograde transport coupled to their degradation by the 26S proteasome. These protective responses act transiently to maintain homeostasis within the ER, but sustained ER stress can ultimately lead to the death of the cell (Rutkowski, et al. (2004) *Trends Cell Biol.* 14: 20-28; Ma, et al. (2001) *Cell* 107: 827-830; Rao, et al. (2004) *Cell Death Differ.* 11: 372-380). As such, genes involved in one or more aspects of the aforementioned unfolded protein response are suitable for practicing the present invention. Non-limiting examples of ER-stress related genes include pancreatic ER kinase gene (PERK), eukaryotic translation initiation factor 2 alpha (eIF-2α, eukaryotic translation initiation factor beta (eIF-2α, inositol requiring 1 (IRE1), activating transcription factor 6 (ARTF6), CAATT enhancer-binding protein homologous protein (CHOP), binding-immunoglobulin protein (BIP), caspase-12, growth and DNA damage protein 34 (GADD34), CreP (a constitutive repressor of eIF2alpha phosphorylation), and X-box-binding protein-1 (XBP-1).

An altered expression of an ER-stress related gene or gene product can be determined by assaying for a difference in the mRNA levels of the corresponding genes between the test myelinating cell and a control cell, when they are contacted with a candidate agent. Alternatively, the differential expression of the ER-stress related gene is determined by detecting a difference in the level of the encoded polypeptide or gene product.

To assay for an agent-induced alteration in the level of mRNA transcripts or corresponding polynucleotides, nucleic acid contained in a biological sample comprising myelinating cells is first extracted according to standard methods in the art. For instance, mRNA can be isolated using various lytic enzymes or chemical solutions according to the procedures set forth in Sambrook et al. (1989), supra or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of an ER-stress related gene.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with ER-stress related genes can be performed. Typically, probes are allowed to form stable complexes with the target polynucleotides (e.g., ER-stress related genes) contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

As is known to one skilled in the art, hybridization can be performed under conditions of various stringency. Suitable hybridization conditions for the practice of the present invention are such that the recognition interaction between the probe and target ER-stress related gene is both sufficiently specific and sufficiently stable. Conditions that increase the stringency of a hybridization reaction are widely known and published in the art. See, for example, (Sambrook, et al., (1989), supra; Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of ER-stress related genes can also be determined by examining the corresponding gene products. Determining the protein level typically involves a) contacting the protein contained in a biological sample comprising myelinating cells with an agent that specifically bind to the ER-stress related protein; and (b) identifying any agent:protein complex so formed. In one aspect of this embodiment, the agent that specifically binds an ER-stress related protein is an antibody, preferably a monoclonal antibody.

The reaction is performed by contacting the agent with a sample of the ER-stress related proteins derived from the test samples under conditions that will allow a complex to form between the agent and the ER-stress related proteins. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure requires the agent to contain a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radio-isotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent: polypeptide complex can be measured directly by the amount of label remained at the site of binding. In an alternative, the ER-stress related protein is tested for its ability to compete with a labeled analog for binding sites on the specific agent. In this competitive assay, the amount of label captured is inversely proportional to the amount of ER-stress related protein present in a test sample.

A number of techniques for protein analysis based on the general principles outlined above are available in the art. They include but are not limited to radioimmunoassays, ELISA (enzyme linked immunoradiometric assays), "sandwich"

immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to ER-stress related proteins are preferable for conducting the aforementioned protein analyses. Where desired, antibodies that recognize a specific type of post-translational modifications (e.g., ER-stress inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an ER-stress related protein in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

For example, to localize a target ER-stress related protein to a specific cell type such as oligodendrocyte, co-staining with one or more antibodies specific for oligodendrocyte markers can be used. Exemplary markers for oligodendrocyte include but are not limited to CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide and proteolipid protein (PLP). To detect or quantify an ER-stress related protein localized in a specific subcellular structure, co-staining with one or more antibodies directed to antigens differentially present in such structure is preferably performed. A wide variety of organelle specific antibodies is available in the art. Non-limiting examples include endoplasmic reticulum (ER) specific antibodies directed to the ER resident protein BIP, plasma membrane specific antibodies reactive with cell surface receptors such as epidermal growth factor receptor (EGF receptor), Golgi specific antibody γ-adaptin, and cytokeratin specific antibodies which differentiate cytokeratins from different cell types (e.g., between epithelial and stromal cells). To detect and quantify the immunospecific binding, digital image systems including but not limited to confocal microscope can be employed.

An altered expression of an ER-stress related gene can also be determined by examining a change in activity of the gene product relative to a control cell. The assay for an agent-induced change in the activity of an ER-stress related protein will dependent on the biological activity and/or the signal transduction pathway that is under investigation. For example, where the ER-stress related protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) *Clinical Immunology* 111: 162-174).

Where the ER-stress related protein is part of a signaling cascade leading to a fluctuation of intracellular pH condition, pH sensitive molecules such as fluorescent pH dyes can be used as the reporter molecules. In another example where the ER-stress related protein is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In yet another example where the ER-stress related protein is a protease, its activity in cleaving substrate proteins can be detected by analyzing the cleaved polypeptides. Several methods for analyzing polypeptides are available in the art. Non-limiting exemplary methods are 2-D electrophoresis, mass spectrum analysis, and peptide sequencing.

The candidate agents identified by the subject method can be further characterized, in whole or in part, by their abilities to modulate neuronal demyelination that occurs in a wide variety of conditions. For instance, neuronal demyelination may occur in disorders inflicted by pathogens or physical injuries, disorders attributable to genetic predispositions, inflammation and/or autoimmune responses. Specifically, neuronal demyelination may occur upon bacterial or viral infection as in, e.g., HIV-vacuolar myelinopathy and HTLV. It may also result from direct contact with toxic substances or accumulation of toxic metabolites in the body as in, e.g., central pontine myelinolysis and vitamin deficiencies. Neuronal demyelination may also manifest in spinal cord injury, genetic disorders including but not limited to leukodystrophies, adrenoleukodystrophy, degenerative multi-system atrophy, Binswanger encephalopathy, tumors in the central nervous system, and multiple sclerosis.

Morphologically, neuronal demyelination can be characterized by a loss of oligodendrocytes in the central nervous system or Schwann cells in the peripheral nervous system. It can also be determined by a decrease in myelinated axons in the nervous system, or by a reduction in the levels of oligodendrocyte or Schwann cell markers. Exemplary marker proteins of oligodendrocytes or Schwann cells include but are not limited to CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide and proteolipid protein (PLP). As such, the candidate agents identified by the subject method encompass substances that can inhibit the deleterious morphological characteristics of neuronal demyelination.

Candidate agents identified by the subject method can be broadly categorized into the following two classes. The first class encompasses agents that when administered into a cell or a subject, reduce the level of expression or activity of an ER-stress causing gene or protein. The second class includes agents that augment the level of expression or activity of an ER-stress suppressing gene or protein (e.g., BIP and PERK). In one aspect, the agent reduces the levels of proteins (e.g., major histocompatibility complex I) that are characteristic of an endoplasmic reticulum stress in remyelinating oligodendrocytes in the central nervous system or Schwann cells in the peripheral nervous system.

Animal Studies:

The development of a biologically active agent beneficial for a neuronal demyelination condition may also involve the use of animal models. Accordingly, the present invention provides a method of using animal models for testing a biologically active agent that modulates a phenomenon associated with a demyelination disorder. The method comprises the steps of: (a) administering a candidate biologically active agent to a test animal generated by a method comprising (i) inducing neuronal demyelination in said test animal, and (ii) allowing said test animal to recover from the demyelination induction for a sufficient amount of time so that remyelination of a demyelinated lesion is exhibited; and (b) determining the effect of said agent upon a phenomenon associated with a demyelination disorder.

The animal models of the present invention encompass any non-human vertebrates that are amenable to procedures yielding a neuronal demyelination condition in the animal's nervous systems including the central and peripheral nervous system. Preferred model organisms include but are not limited to mammals, primates, and rodents. Non-limiting examples of the preferred models are rats, mice, guinea pigs, cats, dogs, rabbits, pigs, chimpanzees, and monkeys. The test animals can be wildtype or transgenic.

In one aspect, the subject method employs a transgenic animal having stably integrated into the genome a transgenic nucleotide sequence encoding interferon-gamma (INF-$\gamma$). In another aspect, the subject method involves a transgenic animal having an altered expression of at least one other gene, wherein upon expression of INF-$\gamma$, the animal exhibits a greater degree of demyelination relative to a transgenic animal having a stably integrated transgenic nucleotide sequence encoding interferon-gamma (INF-$\gamma$) alone. In a preferred aspect, the at least one other gene encodes an ER-stress related protein. In another preferred aspect, the test animal is a heterozygous knock-out of pancreatic ER kinase gene (PERK), having a stably integrated into the genome a transgenic nucleotide sequence encoding interferon-gamma (INF-$\gamma$). Preferably, expression of the transgene(s) carried in the transgenic animal are inducible to effect expression that is ectopical, tissue specific, cell type specific, or even'organelle specific.

As described above, tissue specific and cell specific regulatory sequences are available for expressing transgenes in the central nervous systems. An exemplary sequence is the transcriptional regulatory sequence of the glial fibrillary acidic gene (GFAP). The regulatory sequence allows ectopical expression of transgenes in the central nervous system and specifically in the astrocytes. Where expression of the transgene in particular subcellular location is desired, the transgene can be operably linked to the corresponding subcellular localization sequences by recombinant DNA techniques widely practiced in the art. Exemplary subcellular localization sequences include but are not limited to (a) a signal sequence that directs secretion of the gene product outside of the cell; (b) a membrane anchorage domain that allows attachment of the protein to the plasma membrane or other membraneous compartment of the cell; (c) a nuclear localization sequence that mediates the translocation of the encoded protein to the nucleus; (d) an endoplasmic reticulum retention sequence (e.g. KDEL sequence) that confines the encoded protein primarily to the ER; or (e) any other sequences that play a role in differential subcellular distribution of a encoded protein product.

A demyelination condition in the test animal generally refers to a decrease in myelinated axons in the nervous systems (e.g., the central or peripheral nervous system), or by a reduction in the levels of markers of myelinating cells, such as oligodendrocytes and Schwann cells. Exemplary markers for identifying myelinating cells include but are not limited to CC1, myelin basic protein (MBP), ceramide galactosyltransferase (CGT), myelin associated glycoprotein (MAG), myelin oligodendrocyte glycoprotein (MOG), oligodendrocyte-myelin glycoprotein (OMG), cyclic nucleotide phosphodiesterase (CNP), NOGO, myelin protein zero (MPZ), peripheral myelin protein 22 (PMP22), protein 2 (P2), galactocerebroside (GalC), sulfatide and proteolipid protein (PLP).

These phenomena can be observed by immunohistochemical means or protein analysis described herein. In one aspect, sections of the test animal's brain can be stained with antibodies that specifically recognize an oligodendrocyte marker. In another aspect, the expression levels of oligodendrocyte markers can be quantified by immunoblotting, hybridization means, and amplification procedures, and any other methods that are well-established in the art and/or provided herein.

A number of methods for inducing demyelination in a test animal have been established. For instance, neuronal demyelination may be inflicted by pathogens or physical injuries, agents that induce inflammation and/or autoimmune responses in the test animal. A preferred method employs demyelination-induced agents including but not limited to IFN-$\gamma$ and cuprizone (bis-cyclohexanone oxaldihydrazone). The cuprizone-induced demyelination model is described in Matsushima, et al. (2001) *Brain Pathol.* 11: 107-116. In this method, the test animals are typically fed with a diet containing cuprizone for a few weeks ranging from about 1 to about 10 weeks.

After induction of a demyelination condition by an appropriate method, the animal is allowed to recover for a sufficient amount of time to allow remyelination at or near the previously demyelinated lesions. While the amount of time required for developing remyelinated axons varies among different animals, it generally requires at least about 1 week, more often requires at least about 2 to 10 weeks, and even more often requires about 4 to about 10 weeks. Remyelination can be ascertained by observing an increase in myelinated axons in the nervous systems (e.g., in the central or peripheral nervous system), or by detecting an increase in the levels of marker proteins of a myelinating cell. The same methods of detecting demyelination can be employed to determine whether remyelination has occurred.

Determining the effect of the test agent upon a phenomenon associated with a demyelination may involve any suitable methods known in the art, including but not limited to those mentioned in the above cell-based assay section. In general, immunohistochemical and electron microscopic analysis can be performed to visualize the effect of the test agent. In addition, procedures applicable for detecting differential expression of ER-stress related genes or gene products can be employed. Techniques for measuring activities of ER-stress related proteins are also applicable. As described above, non-limiting examples of ER-stress related genes include pancreatic ER kinase gene (PERK), eukaryotic translation initiation factor 2 alpha (eIF-2$\alpha$, eukaryotic translation initiation factor beta (eIF-2β, inositol requiring 1 (IRE1), activating transcription factor 6 (ARTF6), CAATT enhancer-binding protein homologous protein (CHOP), binding-immunoglobulin protein (BIP), caspase-12, growth and DNA damage protein 34 (GADD34), CreP (a constitutive repressor of eIF2alpha phosphorylation), and X-box-binding protein-1 (XBP-1).

In a separate embodiment, the present invention provides a non-human transgenic animal suitable for elucidating the pathogenesis of neuronal demyelination conditions. The transgenic animal is also useful for developing biologically active agent effective to inhibit neuronal demyelination or promote remyelination of demyelinated lesions. In one aspect, the subject transgenic animal has (a) stably integrated into the genome of the animal a transgenic nucleotide sequence encoding interferon-gamma (INF-γ); and (b) an altered expression of at least one other gene, wherein upon expression of said INF-γ, the animal exhibits a greater degree of demyelination relative to a transgenic animal having a stably integrated transgenic nucleotide sequence encoding interferon-gamma (INF-γ) as in (a), but lacking said altered expression of said at least one other gene.

The present invention contemplates transgenic animals that carry one or more desired transgenes in all their cells, as well as animals which carry the transgenes in some, but not all their cells, i.e., mosaic animals. Animals of any species, including, but not limited to, mice, rats, rabbits, guinea pigs, pigs, micro-pigs, goats, and non-human primates, e.g., baboons, monkeys, and chimpanzees may be used to generate the subject transgenic animals.

A desired transgene may be integrated as a single copy or in concatamers, e.g., head-to-head tandems or head-to-tail tandems. The desired transgene may also be selectively introduced into and activated in a particular tissue or cell type, preferably cells within the central nervous system. The regulatory sequences required for such a cell-type specific activation will depend upon the particular cell type of interest, and will be apparent to those of skill in the art. Preferably, the targeted cell types are located in the nervous systems, including the central and peripheral nervous systems.

When it is desired that the transgene be integrated into the chromosomal site of the endogenous counterpart, gene targeting is preferred. Briefly, when such a technique is to be utilized, vectors containing some nucleotide sequences homologous to the endogenous counterpart are designed for the purpose of integrating, via homologous recombination with chromosomal sequences, into and disrupting the function of the nucleotide sequence of the endogenous gene.

Advances in technologies for embryo micromanipulation now permit introduction of heterologous DNA into fertilized mammalian ova as well. For instance, totipotent or pluripotent stem cells can be transformed by microinjection, calcium phosphate mediated precipitation, liposome fusion, retroviral infection or other means. The transformed cells are then introduced into the embryo, and the embryo will then develop into a transgenic animal. In a preferred embodiment, developing embryos are infected with a viral vector containing a desired transgene so that the transgenic animals expressing the transgene can be produced from the infected embryo. In another preferred embodiment, a desired transgene is coinjected into the pronucleus or cytoplasm of the embryo, preferably at the single cell stage, and the embryo is allowed to develop into a mature transgenic animal. These and other variant methods for generating transgenic animals are well established in the art and hence are not detailed herein. See, for example, U.S. Pat. Nos. 5,175,385 and 5,175,384.

The transgenic animals of the present invention can be broadly categorized into two types: "knockouts" and "knockins". A "knockout" has an alteration in the target gene via the introduction of transgenic sequences that results in a decrease of function of the target gene, preferably such that target gene expression is insignificant or undetectable. A "knockin" is a transgenic animal having an alteration in a host cell genome that results in an augmented expression of a target gene, e.g., by introduction of an additional copy of the target gene, or by operatively inserting a regulatory sequence that provides for enhanced expression of an endogenous copy of the target gene. The knock-in or knock-out transgenic animals can be heterozygous or homozygous with respect to the target genes. Both knockouts and knockins can be "bigenic". Bigenic animals have at least two host cell genes being altered. A preferred bigenic animal carries a transgene encoding IFN-γ and another transgenic sequence that disrupts the function of at least one other gene.

In certain aspect of this embodiment, the at least one other gene is an ER-stress related gene. In another aspect, the other gene can be an exogenous gene, i.e., a gene that is not present in the host cell, or an endogenous gene, i.e., the introduced gene finds an endogenous counterpart native to the recipient animal. Such ER-stress related gene may be selected from the group consisting of pancreatic ER kinase gene (PERK), eukaryotic translation initiation factor 2 alpha (eIF-2α, eukaryotic translation initiation factor beta (eIF-2β, inositol requiring 1 (IRE 1), activating transcription factor 6 (ARTF6), CAATT enhancer-binding protein homologous protein (CHOP), binding-immunoglobulin protein (BIP), caspase-12, growth and DNA damage protein 34 (GADD34), CreP (a constitutive repressor of eIF2alpha phosphorylation), and X-box-binding protein-1 (XBP-1).

A preferred non-human transgenic animal comprises a heterozygous knockout of pancreatic ER kinase gene (PERK), and has stably integrated into the genome a transgenic nucleotide sequence comprising interferon-gamma (INF-γ). In one aspect, a preferred transgenic animal exhibits an increased vulnerability to INF-γ-mediated neuronal demyelination relative to a wildtype animal.

Also provided in the present invention are cells of the subject non-human transgenic animal. In one aspect, the cells comprise stably integrated in the genome a transgene encoding INF-γ and an alteration in at least one other gene encoding a protein correlated with ER stress. In another aspect, the subject cells are from the central nervous system. In yet another aspect, the subject cells are oligodendrocytes. In yet another aspect, the subject cells are from the peripheral nervous system including but not limited to Schwann cells.

As discussed in the sections above, these cells are particularly useful for conducting cell-based assays for elucidating the molecular bases of neuronal demyelination conditions, and for developing agents effective for inhibiting neuronal demyelination or promoting remyelination.

Pharmaceutical Compositions of the Present Invention:

The selected biologically active agents effective to modulate ER-stress related genes or proteins may be used for the preparation of medicaments for treating neuronal demyelination disorders. A preferred class of agents is effective to alleviate IFN-γ elicited ER stress in oligodendrocytes.

In one aspect, the selected agent of this invention can be administered to treat neuronal demyelination inflicted by pathogens such as bacteria and viruses. In another aspect, the selected agent can be used to treat neuronal demyelination caused by toxic substances or accumulation of toxic metabolites in the body as in, e.g., central pontine myelinolysis and vitamin deficiencies. In yet another aspect, the agent can be used to treat demyelination caused by physical injury, such as spinal cord injury. In still yet another aspect, the agent can be administered to treat demyelination manifested in disorders having genetic attributes, genetic disorders including but not limited to leukodystrophies, adrenoleukodystrophy, degenerative multi-system atrophy, Binswanger encephalopathy, tumors in the central nervous system, and multiple sclerosis.

Various delivery systems are known and can be used to administer a biologically active agent of the invention, e.g., encapsulation in liposomes, microparticles, microcapsules, expression by recombinant cells, receptor-mediated endocytosis (see, e.g., Wu and Wu, (1987), *J. Biol. Chem.* 262:4429-4432), construction of a therapeutic nucleic acid as part of a retroviral or other vector, etc. Methods of delivery include but are not limited to intra-arterial, intra-muscular, intravenous, intranasal, and oral routes. In a specific embodiment, it may be desirable to administer the pharmaceutical compositions of the invention locally to the area in need of treatment; this may be achieved by, for example, and not by way of limitation, local infusion during surgery, by injection, or by means of a catheter. In certain embodiment, the agents are delivered to a subject's nerve systems, preferably the central nervous system. In another embodiment, the agents are administered to neuronal tissues undergoing remyelination.

Administration of the selected agent can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician.

The preparation of pharmaceutical compositions of this invention is conducted in accordance with generally accepted procedures for the preparation of pharmaceutical preparations. See, for example, *Remington's Pharmaceutical Sciences* 18*th Edition* (1990), E. W. Martin ed., Mack Publishing Co., PA. Depending on the intended use and mode of administration, it may be desirable to process the active ingredient further in the preparation of pharmaceutical compositions. Appropriate processing may include mixing with appropriate non-toxic and non-interfering components, sterilizing, dividing into dose units, and enclosing in a delivery device.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or aerosol when used with an appropriate aerosolizer device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

Where desired, the pharmaceutical compositions can be formulated in slow release or sustained release forms, whereby a relatively consistent level of the active compound are provided over an extended period.

Other Applications of the Identified ER-Stress Related Genes:

Another embodiment of the present invention is a method of promoting remyelination using stem cells in a subject. In this approach, cultured stem cells are typically transfected with a gene capable of ameliorating ER stress in myelinating oligodendrocytes. The genetically modified stem cells are then introduced into the CNS of a subject suffering from a neuronal demyelination condition. Any means effective to deliver the genetically modified stem cells are applicable. Typically, the stem cells are directly injected into the nervous system of a subject. This methodology is described in detail in e.g., Morris, et al. (1997) *J Biol Chem.* 272(7): 4327-34, which is incorporated herein by reference. Candidate genes to be introduced into stem cells include but are not limited to BIP, PERK, and suppressor of cytokine signaling 1 (SOCS1).

It is documented that BIP is required to protect cells from ER stress; overexpression of BIP permits continued translation of cellular mRNAs, and hence reduces ER stress. SOCS1 is known to block INF-γ signal transduction. As such, stem cells overexpressing SOCS1 and hence myelinating cells derived from such stem cells, are expected to be less sensitive to the demyelinating effect mediate by INF-γ.

Populations of neuronal cells can be produced from differentiating cultures of embryonic stem cells (Li et al., (1998) *Curr. Biol.* 8: 971-974), and have been used in experimental models to correct various deficits in animal model systems (review, Svendsen and Smith, *Trends in Neurosci.* 22: 357-364).

In humans, neuronal cells can be derived from human embryonal carcinoma cells, and can be induced to differentiate using retinoic acid. These embryonic stem cells have been shown to correct deficits in experimental models of CNS disease. In some embodiments, modulators of ER stress can be expressed in pluripotent stem cells. Preferably, the engineered stem cells can be introduced into patients in need thereof to induce regeneration and/or protect neuronal cells from demyelination associated with anyone of the disorders cited herein. Pluripotent stem cells may be embryonic stem cells (ES) or embryonic germ cells (EG). Generation of neural progenitors from stem cells in vitro may serve as an unlimited source of cells for tissue reconstruction and for the delivery and expression of genes in the nervous system.

Methods for culturing ES and EG cells are known in the art. For instance, ES and EG lines may be cultured on feeder layers, and may be grown and maintained in an undifferentiated state in the presence of recombinant hormones such as Fibroblast Growth Factor and Leukemia Inhibitory Factor. Differentiation can be initiated either by changing the hormonal milieu, forming embryoid bodies or a combination of both. Embryoid body formation is the most widely used process. Alternatively, tissue-specific reversible transformation can be used for establishing differentiated neuronal cell lines using stem cells as a starting material according to the method described in US Patent Application 20060068496, which is incorporated herein by reference. US Patent Application 20060068496 discloses methods that employ tissue specific expression of a transforming gene, which can be used to identify and culture the particular cell type. This transforming event can, in some forms of the method, then be reversed, using one of a number of possible processes, leaving a clonal or semi-purified population of non-transformed, differentiated cells, including populations of different or semi-purified cells, or a clonal population of cells, as discussed herein. The glial fibrillary acetic protein (GFAP) promoter has been used to selectively express genes in cells of glial origin. Neuronal progenitor cells can be differentiated to give rise to neurons and glial cells. Markers that can be used to identify a neuronal cell include but are not limited to GFAP and MPB.

The preferred cell for use in cell therapy is human embryonic stem cell. In one aspect, the present invention provides an enriched preparation of undifferentiated human embryonic stem cells capable of expressing a modulator of one or more ER stress proteins and that can proliferate in vitro and differentiate into neural progenitor cells, neuron cells and/or glial cells. In another embodiment of the present invention, neural progenitor cells are first derived from human ES cells, which are engineered to express one or more modulators of the ER stress pathway, and subsequently are differentiated into mature neuronal cells, and glial cells including oligodendrocyte and astrocyte cells. Alternatively, the neuronal progenitor cells are first differentiated into mature neuronal cells that include oligodendrocytes and astrocytes, which are subsequently engineered to express one or more modulators of the ER stress response.

The modulators that can be induced to be expressed in the neural progenitor cells include modulators of protein folding and maturation, protein transport, protein synthesis and modification, $Ca^{2+}$ homeostasis, transcription factors, UPR target genes, and proteins that mediate apoptosis. Modulators of protein folding and maturation include but are not limited to modulators of BIP/GRP78, protein disulfide-isomerase-related protein P5, collagen binding protein 2, fourth mammalian ER DNAJ protein (ERdj4), oxygen regulated protein 150 kD (ORP150), FK506-binding protein (FKBP13), GRP94, protein disulfide-isomerase ERp70-like, protein disulfide-isomerase ERp60-like, proline 4-hydroxylase β-subunit (P4HB), hsc70 (71-kD heat shock cognate protein). Modulators of protein transport include but are not limited to modulators of putative mitochondrial membrane protein import receptor (hTIM44), translocon-associated protein delta subunit (TRAP δ), and transmembrane protein mp24. Modulators of protein synthesis and modification include but are not limited to modulators of glycyl-tRNA synthase, alanyl-tRNA synathase, asparagine synthase, glutamine-fructose-6-phosphate amidotransferase (GFAT), and integral membrane protein 1 (ITM1). Modulators of $Ca^{2+}$ homeostasis include but are not limited to modulators of calreticulin, stanniocalcin 2, plasma membrane $Ca^{2+}$ pumping ATPase, calnexin, novel DNA-binding/EF-hand/leucine zipper protein (NEFA), and nucleonidin 1. Modulators of transcription factors include but are not limited to modulators of CHOP, C/EBP-beta, TGF-β-stimulated clone 22 (TSC22)-like, X-box-binding protein 1 (XBP-1), and Egr-1. Modulators of UPR target genes include but are not limited to modulators of HERP and SERP/RAMP4. Modulators of apoptosis include but are not limited to modulators of Bbc3/PUMA, caspase 3, and caspase 12.

Preferably, the modulators that are expressed in the undifferentiated or differentiated neuronal cells are modulators of the PERK pathway. In an embodiment, one or more modulators of the PERK pathway can be expressed in the undifferentiated or differentiated neural cells. For example, the neural progenitor cells can be induced to express a synthetic PERK fusion enzyme that enhances the level of the phosphorylated eIF-2α (p-eIF-2α), while simultaneously expressing an inhibitor of the INF-γ cytokine signaling pathway e.g. SOCS1.

In yet another aspect, the present invention provides neural progenitor cells, neuronal cells and glial cells that express modulators of the PERK pathway and can be used for cell therapy and gene therapy. The route of delivery that is selected for the stem cells is crucial in that it helps to determine whether or not repair of the damaged organ will occur. A high stem cell concentration near the damaged area increases the chances that sufficient stem cell localization and differentiation occurs in order to repair the organ. In many cases this involves the targeted and regional administration of stem cells.

Gene therapy is an alternative approach for promoting remyelination by modulating ER stress of myelinating cells. When expression vectors are used for gene therapy in vivo or ex vivo, a pharmaceutically acceptable vector is preferred, such as a replication-incompetent retroviral or adenoviral vector. Pharmaceutically acceptable vectors containing an ER-stress suppressing genes of this invention can be further modified for transient or stable expression of the inserted polynucleotide. As used herein, the term "pharmaceutically acceptable vector" includes, but is not limited to, a vector or delivery vehicle having the ability to selectively target and introduce an ER-stress suppressing gene into cells located in the nerve systems, and preferably oligodendrocytes in the nerve systems. An example of a replication-incompetent retroviral vector is LNL6 (Miller, A. D. et al. (1989) *BioTechniques* 7:980-990). The methodology of using replication-incompetent retroviruses for retroviral-mediated gene transfer of gene markers is well established (Correll et al. (1989) *PNAS USA* 86:8912; Bordignon (1989) *PNAS USA* 86:8912-52; Culver, K. (1991) *PNAS USA* 88:3155; and Rill, D. R. (1991) *Blood* 79(10):2694-700. Clinical investigations have shown that there are few or no adverse effects associated with the viral vectors, see Anderson (1992) *Science* 256:808-13. Alternatively, introduction of ER-stress suppressing genes can be performed using the methodology described in Chernajovsky, et al. (2004) Nat. Rev. Immunol. 4(10): 800-11.

The expression of ER stress causing genes can be inhibited or prevented in myelinating cells, including oligodendrocytes and Scwhann cells, by using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example Hammond et al. (2001) *Science* 10; 293(5532):1146-50, Caplen et al. (2001) *Proc Natl Acad Sci USA*. 2001 Aug. 14; 98(17): 9742-7, all of which are herein incorporated by reference. Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using *E. coli* RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in for example Brummelkamp et al. (2002) *Science* April 19; 296 (5567):550-3. Epub 2002 Mar. 21; Brummelkamp et al. *Cancer Cell* (2002) September 2(3):243-7. Paddison et al. (2002) *Genes Dev.* 2002 Apr. 15; 16(8):948-58. Various methods for introducing such vectors into cells, either in vitro or in vivo (e.g. gene therapy) are known in the art.

Accordingly, in an embodiment the expression of one or more ER-stress causing genes may be inhibited by introducing into or generating within a cell an siRNA or siRNA-like molecule corresponding to a nucleic acid encoding the ER stress-causing gene or fragment thereof, or to an nucleic acid homologous thereto. "siRNA-like molecule" refers to a nucleic acid molecule similar to a siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially homologous to a nucleic acid encoding the ER stress-causing gene or a fragment or variant (or a fragment of a variant) thereof. Such a variant is capable of encoding a protein having ER stress-causing activity.

Such RNAi methods can be used to inhibit expression of IFN-γ in, for example, the central nervous system. ER stress-causing genes that may be inhibited by RNAi methods include, but are not limited to IFN-γ, GADD34, protein phosphatase 1 (PP1), and one or more genes that mediate apoptosis e.g. genes that encode caspases.

The invention may be better understood by reference to the following examples, which are intended to merely illustrate but not limit the mode now known for practicing the invention.

Example 1

IFN-γ Does not Affect the Initial Phase Demyelination, Oligodendrocyte Loss or Reduction of Myelin Gene Expression The effects of IFN-γ on demyelination were evaluated in a cuprizone animal model using transgenic mice that allow for temporally regulated delivery of IFN-γ using the tetracycline controllable system (Lin, et al. (2004) *J. Neurosci.* 24: 10074-10083). The transgenic mice were generated by mating line 110 GFAP/tTA mice on the C57BL/6 background with line 184 TRE/IFN-γ on the C57BL/6 background to produce GFAP/tTA; TRE/IFN-γ double transgenic mice (Lin, et al. (2004) *J. Neurosci.* 24: 10074-10083). Transcriptional activation of the TRE/IFN-γ transgene by tTA was repressed in the control (DOX+) mice by adding 0.05 mg/ml doxycycline to the drinking water which was provided ad libitum from the day of conception. The DOX+ double transgenic mice were GFAP/tTA; TRE/IFN-γdouble transgenic animals fed cuprizone chow and never released from the doxycycline solution. DOX− double transgenic mice were GFAP/tTA; TRE/IFN-γdouble transgenic animals fed cuprizone chow and released from doxycycline to induce expression of IFN-γ.

Demyelination was induced in 6-week-old DOX+ and DOX− male mice by feeding the mice a diet of milled mouse chow containing 0.2% cuprizone (Sigma-Aldrich, St. Louis, Mich.) for up to 6 weeks. Subsequently, both groups of mice were returned to a normal diet for up to 3 weeks to allow remyelination to occur. All animal procedures were conducted in complete compliance with the NIH *Guide for the Care and Use of Laboratory Animals* and were approved by the Institutional Animal Care and Use Committee of The University of Chicago.

The effects of INF-γ and MBP on demyelination were evaluated as the level of INF-γ and MHC-1, the loss of oligodendrocytes, and the expression of myelin genes.

The expression of IFN-γ in these animals was examined by Enzyme-Linked Immunosorbent Assay (ELISA) analysis as follows. Spinal cord and forebrains were removed, rinsed in ice cold PBS, and immediately homogenized in five volumes of PBS with complete protease cocktail (Roche, Indianapolis, Ind.) using a motorized homogenizer. After incubation on ice for 5 min the extracts were cleared by centrifugation at 14000 rpm for 10 min. The protein content of each extract was determined by the DC protein assay (Bio-Rad, Hercules, Calif.). ELISA assays were performed using Mouse IFN-γ Quantikine ELISA kit (R&D system, Minneapolis, Minn.) and MBP antibodies (1:1000; Sternberger Monoclonals) according to the manufacture's instructions.

Real time PCR was used to determine the effect of IFN-γ on the expression of MHC-1. RNA was isolated from the corpus callosum (Jurevics, et al., 2002) using Trizol reagent (Invitrogen, Carlsbad, Calif.) and treated with DNAseI (Invitrogen, Carlsbad, Calif.) to eliminate genomic DNA. Reverse transcription was performed using Superscript First Strand Synthesis System for RT-PCR kit (Invitrogen, Carlsbad, Calif.). Real-time PCR was performed with iQ supermix (Bio-Rad, Hercules Calif.) on a Bio-Rad iQ real-time PCR detection system (Bio-Rad, Hercules Calif.). The primers and probes (Integrated DNA Technologies Inc., Coralville, Iowa) for real-time PCR were as follows:

The sense and antisense primers that were used in the PCR reaction for MHC-1 were: ATTCCCCAAAGGCCCATGT (SEQ ID NO: 1) and GTCTCCACAAGCTCCATGTCC (SEQ ID NO: 2), respectively. The probe was MHC-I probe: TGCTGGGCCCTGGGCTTCTACC (SEQ ID NO: 3)

The effect of INF-γ on the population of oligodendrocytes was evaluated by immunohistochemical analysis of oligodendrocytes using an anti-CC1 antibody (APC7, 1:50; EMD Biosciences, Inc., La Jolla, Calif.) Immunohistochemistry was performed on brain sections obtained from mice that were first anesthetized mice and perfused through the left cardiac ventricle with 4% paraformaldehyde in 0.1 M PBS. The brains were removed, postfixed with paraformaldehyde, cryopreserved in 30% sucrose, embedded in OCT and frozen on dry ice. Frozen sections were cut in a cryostat at a thickness of 10 μm. Coronal sections at the fornix region of the corpus callosum corresponding to Sidman sections 241-251 were selected for use, and all comparative analyses were restricted to midline corpus callosum (Sidman, et al. (1971) *Atlas of the Mouse Brain and Spinal Cord* (Harvard Univ. Press, Cambridge, Mass.). For immunohistochemistry, frozen sections were treated with −20° C. acetone, blocked with PBS containing 10% NGS and 0.1% Triton X-100 and incubated overnight with the primary antibody diluted in blocking solution. Appropriate fluorochrome- or enzyme-labeled secondary antibodies (Vector Laboratories, Burlingame, Calif.) were used for detection. An antibody against CC1 (APC7, 1:50; EMD Biosciences, Inc., La Jolla, Calif.) was used as a marker for mature oligodendrocytes. Antibody against MBP (1:1000; Sternberger Monoclonals, Lutherville, Mass.) was used to verify the degree of myelination. Antibody against active-caspase-3 (1:50, Cell signaling Technology, Beverly, Mass.) was used as a marker for apoptotic cells. Fluorescent stained sections were mounted with Vectashield mounting medium with DAPI (Vector Laboratories) and visualized with a Zeiss Axioplan fluorescence microscope. Images were captured using a Photometrics PXL CCD camera connected to an Apple Macintosh computer using the Open Lab software suite. Immunopositive cells were quantified by counting positive cells within the median of the corpus callosum, confined to an area of 0.04 mm$^2$. Only those cells with nuclei observable by DAPI staining were counted. Each MBP immunostaining slide was scored on a scale of zero to four. A score of zero indicates complete demyelination, and a score of four indicates normal myelination in the corpus callosum of adult mice.

Real time PCR was used as described above to determine the expression of the MBP, PLP and CGT using the following primers and probes: MBP sense primer: GCTCCCTGC-CCCAGAAGT (SEQ ID NO: 4); MBP antisense primer: TGTCACAATGTTCTTGAAGAAATGG (SEQ ID NO: 5); MBP probe: AGCACGGCCGGACCCAAGATG (SEQ ID NO: 6);

PLP sense primer: CACTTACAACTTCGCCGTCCT (SEQ ID NO: 7); PLP antisense primer: GGGAGTTTC-TATGGGAGCTCAGA (SEQ ID NO: 8); PLP probe: AACT-CATGGGCCGAGGCACCAA (SEQ ID NO: 9);

CGT sense primer: TTATCGGAAATTCACAAGGAT-CAA (SEQ ID NO: 10); and CGT antisense primer: TGGC-GAAGAATGTAGTCTATCCAATA (SEQ ID NO: 11); CGT probe: CCGGCCACCCTGTCAATCGG (SEQ ID NO: 12). The degree of demyelination was determined as the level of MBP was also determined by immunohistochemical analysis as described above and using an antibody against MBP (1:1000; Sternberger Monoclonals, Lutherville, Mass.). Demyelination was also assessed by electron microscopy as follows. Mice were anesthetized and perfused with 0.1 M PBS containing 4% paraformaldehyde and 2.5% glutaraldehyde (PH 7.3). Brains were sliced into 1-mm sections, and the section corresponding to the region of the formix was trimmed and processed for analysis and oriented so that a cross-section of the corpus callosum was achieved. Thin sections were cut, stained with uranyl acetate and lead citrate and analyzed as previously described (Coetzee, et al. (1996) *Cell* 86: 209-219). The total percent of remyelinated axons was based on the analysis of a minimum of 300 fibers per mouse.

Figure 2:
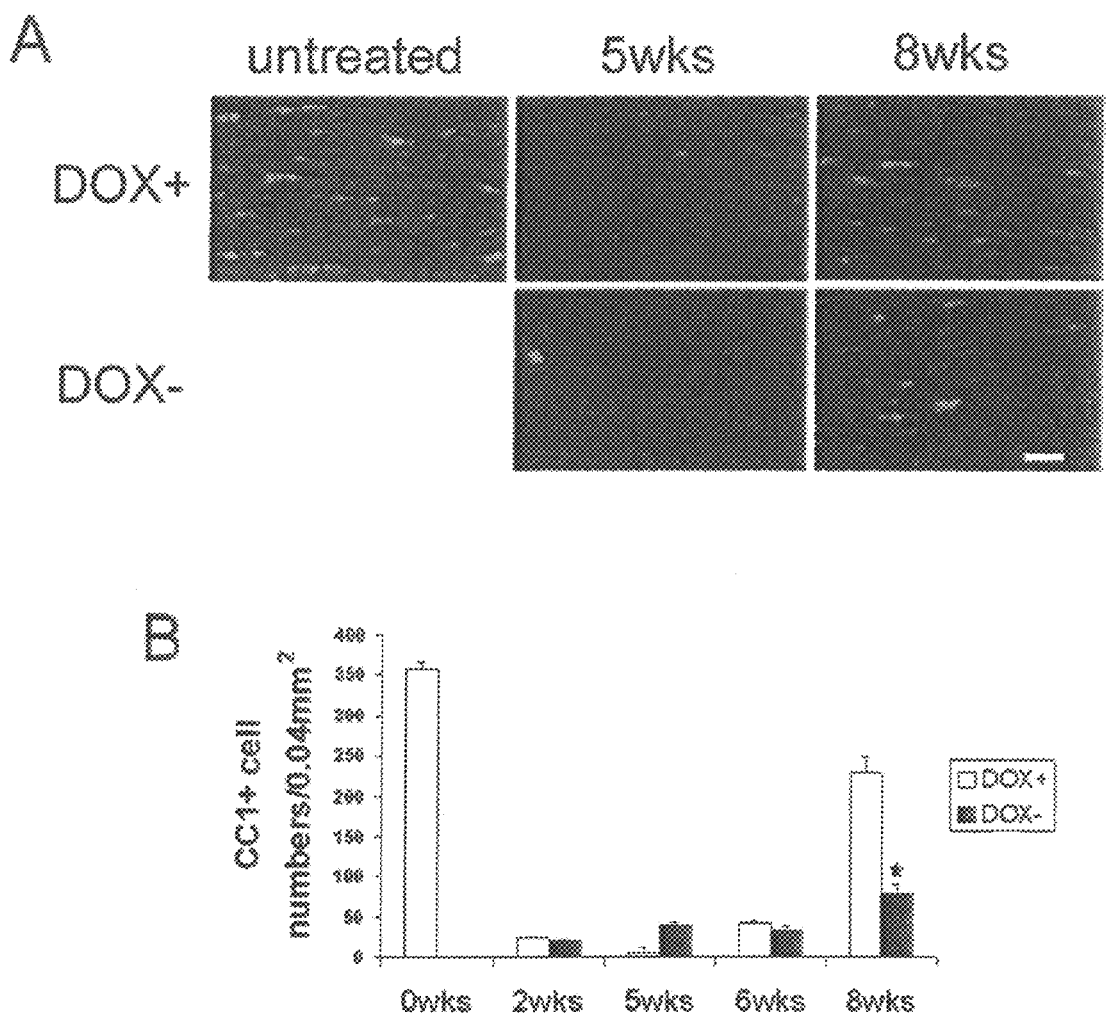
FIG. 2 depicts the comparative results of immunostaining mature oligodendrocytes with anti-CC1 antibodies in the corpus callosum of double transgenic mice treated with cuprizone. (A) Mature oligodendrocytes, detected by CC1 immunostaining (red fluorescence), became depleted in both DOX+ and DOX− double transgenic mice by 5 weeks. The regeneration of oligodendrocytes during recovery was markedly reduced in DOX− double transgenic mice at 8 weeks. Blue fluorescence shows DAPI countstain, n=3, scale bar=25 μM. (B) CC1 positive cell numbers in the corpus callosum of double transgenic mice treated with cuprizone, n=3, *p<0.01.
Figure 3:
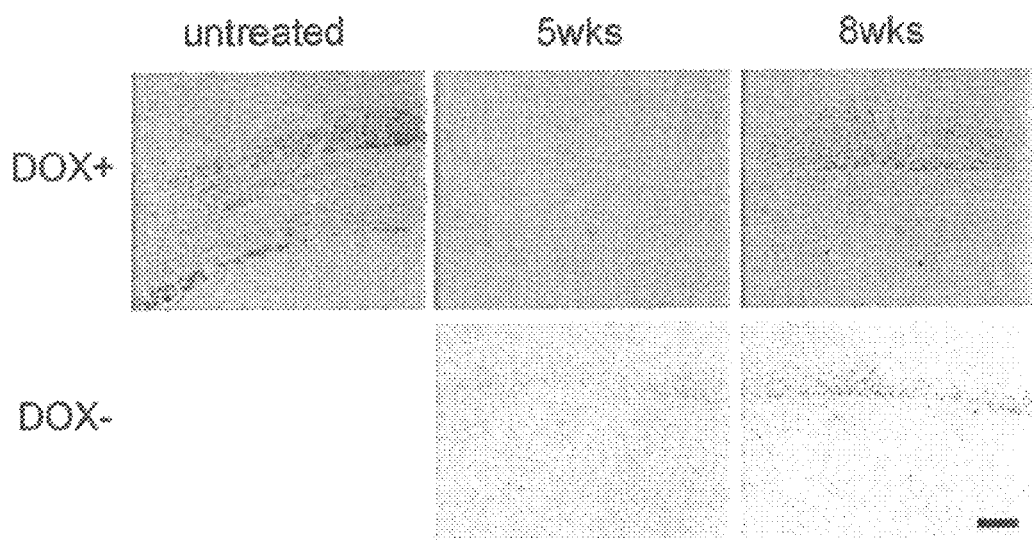
FIG. 3 depicts the results of immunohistochemical and electron microscopic analysis of the corpus callosum of both DOX+ and DOX-double transgenic mice. (A) MBP immunostaining showed that the presence of IFN-γ did not affect cuprizone-induced demyelination at 5 weeks, and suppressed remyelination at 8 weeks, n=4, scale bar=50 μm. (B) Myelination score for MBP immunostaining, with 0 for complete demyelination and 4 for normal myelination of adult male mice, n=4, *p<0.01.
Figure 3:
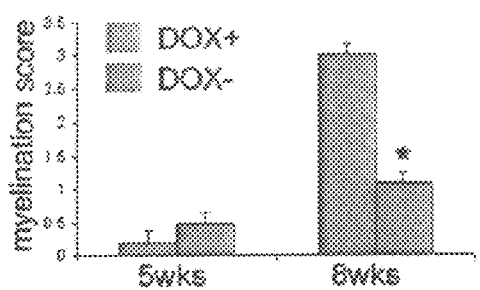
Figure 4:
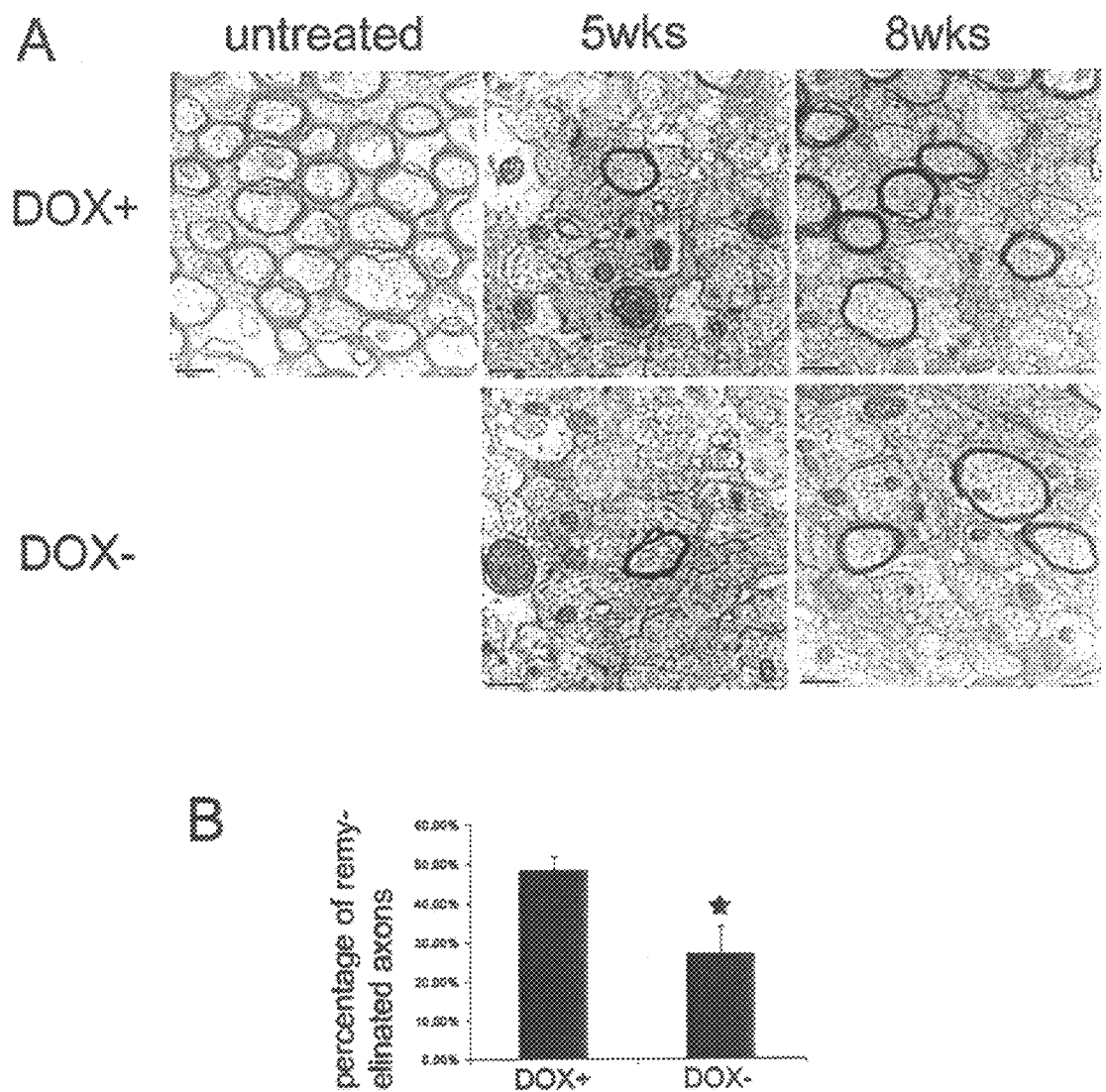
FIG. 4(A). Demyelination and remyelination were assessed by EM analysis (n=4), scale bar=0.5 μM. (B) Percentage of remyelinated axons was calculated from 4 mice at 8 weeks, *p<0.01
Figure 5:
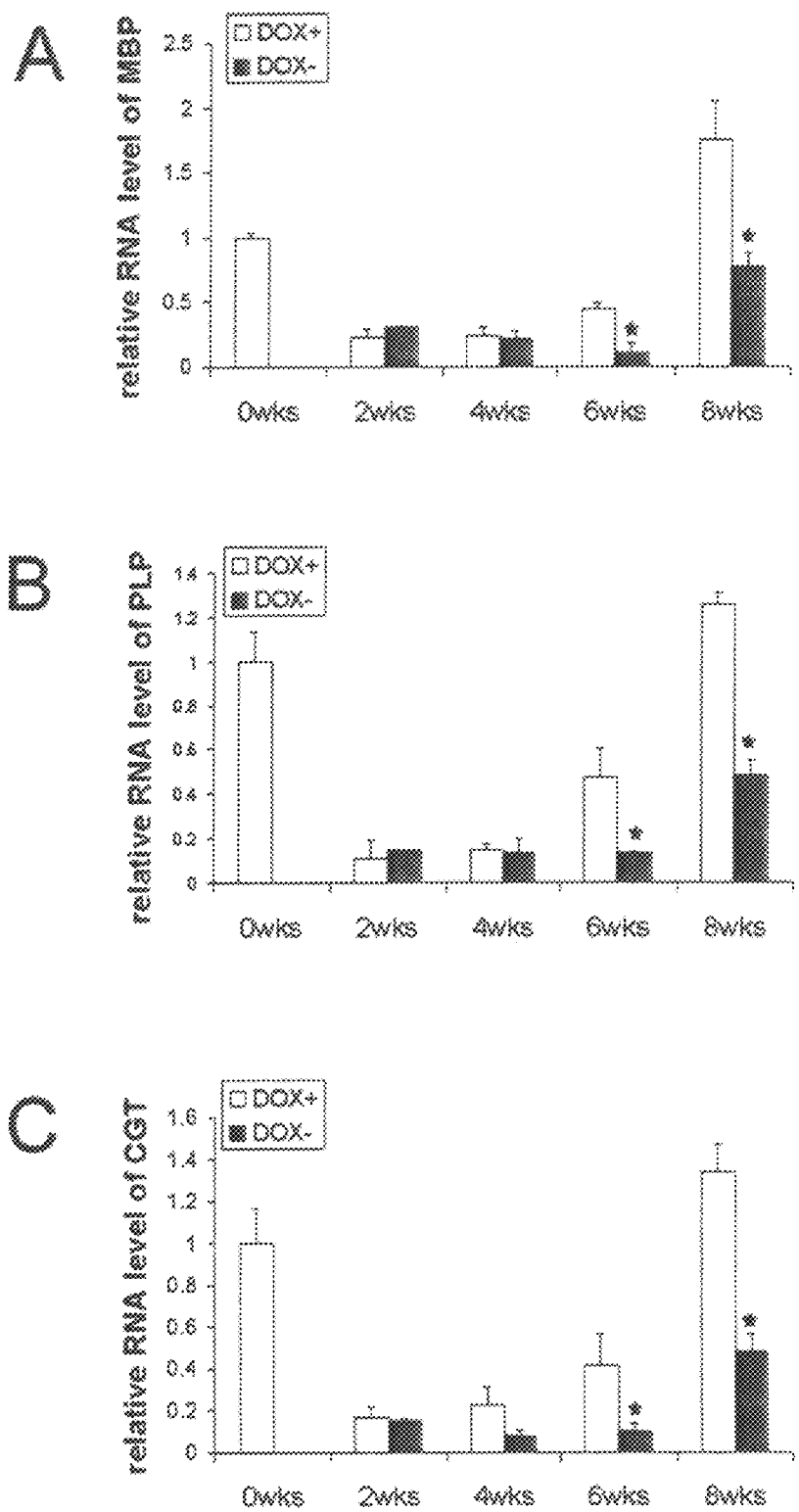
FIG. 5 depicts the results of real-time PCR detecting the relative RNA levels of MBP, PLP and CGT in DOX+ and DOX-double transgenic mice over a course of 8 weeks. The expression pattern of myelin genes in the corpus callosum of mice treated with cuprizone, n=3 was obtained. (A) Real-time PCR analysis of the relative mRNA level of MBP, *p<0.05. (B) Real-time PCR analysis of the relative mRNA level of PLP, *p<0.05. (C) Real-time PCR analysis of the relative mRNA level of CGT, *p<0.05.

The results show that DOX+ mice did not express IFN-γ in the forebrain for the duration of the study, while the DOX− mice began expressing approximately 20 pg/mg of IFN-γ in the forebrain after 2 weeks of cuprizone treatment and removal of doxycycline (FIG. 1A). Real-time PCR analysis showed that the increased level of IFN-γ led to a significant increase in the expression of major histocompatibility complex (MHC) class I (MHC-I), a downstream target of IFN-γ signaling, in the corpus callosum during remyelination (FIG. 1B). After 5 weeks of cuprizone treatment demyelination in the corpus callosum of both DOX+ and DOX− double transgenic mice reached maximum levels (FIG. 2), and axons were almost completely demyelinated (FIG. 3). Also, at this time, CC1 positive mature oligodendrocytes were lost within the lesion site in both DOX+ and DOX− double transgenic mice (FIG. 4). Furthermore, during the period of demyelination at 2 and 4 weeks of treatment with cuprizone there was a reduction in the expression of the myelin genes MBP, proteolipid protein (PLP) and ceramide galactosyltransferase (CGT) that was comparable between DOX+ and DOX− double transgenic mice (FIG. 5).

These data suggest that the presence of IFN-γ does not have a significant effect on the initial pathological processes induced by cuprizone exposure.

Statistics. Data are expressed as mean±standard deviation. Multiple comparisons were statistically evaluated by one way AVONA test using Sigmastat 3.1 software. Differences were considered statistically significant if $p<0.05$.

Example 2

IFN-γ Suppresses Remyelination in Demyelinated Lesions

The effect of IFN-γ on the remyelination in the cuprizone treated mice described in Example 1 was determined following withdrawal of cuprizone at week 5. The experimental methods used are the same as described in Example 1.

FIGS. 1A and B show that the increased level of INF-γ persisted in the DOX− mice even after withdrawal of cuprizone, and the increase in INF-γ was accompanied by a sustained increase in MCH-1. By week 8, a significant number of oligodendrocytes were seen in the corpus callosum of the DOX+ mice, while the regeneration of oligodendrocytes in the DOX− was suppressed (FIGS. 2A and B). Remyelination in the corpus callosum of DOX+ double transgenic mice began at week 6, and was evident 2 weeks after cuprizone was removed from the diet (week 8; FIG. 3). In control mice DOX+, a large number of axons showed substantial recovery at 8 weeks (48.4%±4%, FIG. 4), whereas remyelination remained markedly suppressed in the corpus callosum of the DOX− mice (week 8; FIG. 3), with fewer remyelinated axons (26.9%±7%, FIG. 4). Consistent with previous findings that have shown that myelin genes are upregulated during the process of remyelination, the myelin genes MBP, PLP and CGT were upregulated at week 6, and reached peak levels at week 8 in the corpus callosum of the control DOX+ mice (FIG. 5). However, the expression of the same myelin genes was significantly depressed at both week 6 and week 8 in the DOX− mice (FIG. 5).

These data indicate that the presence of IFN-γ in demyelinated lesions suppresses remyelination.

Example 3

IFN-γ Dramatically Reduces Repopulation of CC1 Positive Oligodendrocytes in Demyelinated Lesions Remyelination occurs by the repopulation of demyelinated lesions by oligodendrocyte precursors (OPCs) at the site of the lesion where they differentiate into oligodendrocytes (Matsushima, et al. (2001) Brain Pathol. 11: 107-116; Mason, et al. (2000) J. Neurosci. Res. 61: 251-262). CC1 positive oligodendrocytes are derived from NG2 positive OPCs (Watanabe et al 1998; Mason et al 2000)). Therefore, repopulation of a lesion may be evaluated by the presence of CC1 and/or NG2 positive cells.

The effect of INF-γ on the repopulation of demyelinated lesions by oligodendrocyte precursors (OPC) was evaluated in the mice of Example 2 as the number of CC1 positive mature oligodendrocytes and NG2 positive OPCs that were counted in sections from the corpus callosum of both DOX+ and DOX− mice. The methods used for analyzing the oligodendrocytes during remyelination is the same as that described in Example 2. Immunostaining of NG2 in OPCs was performed using NG2 antibodies (1:50; Chemicon).

Figure 6:
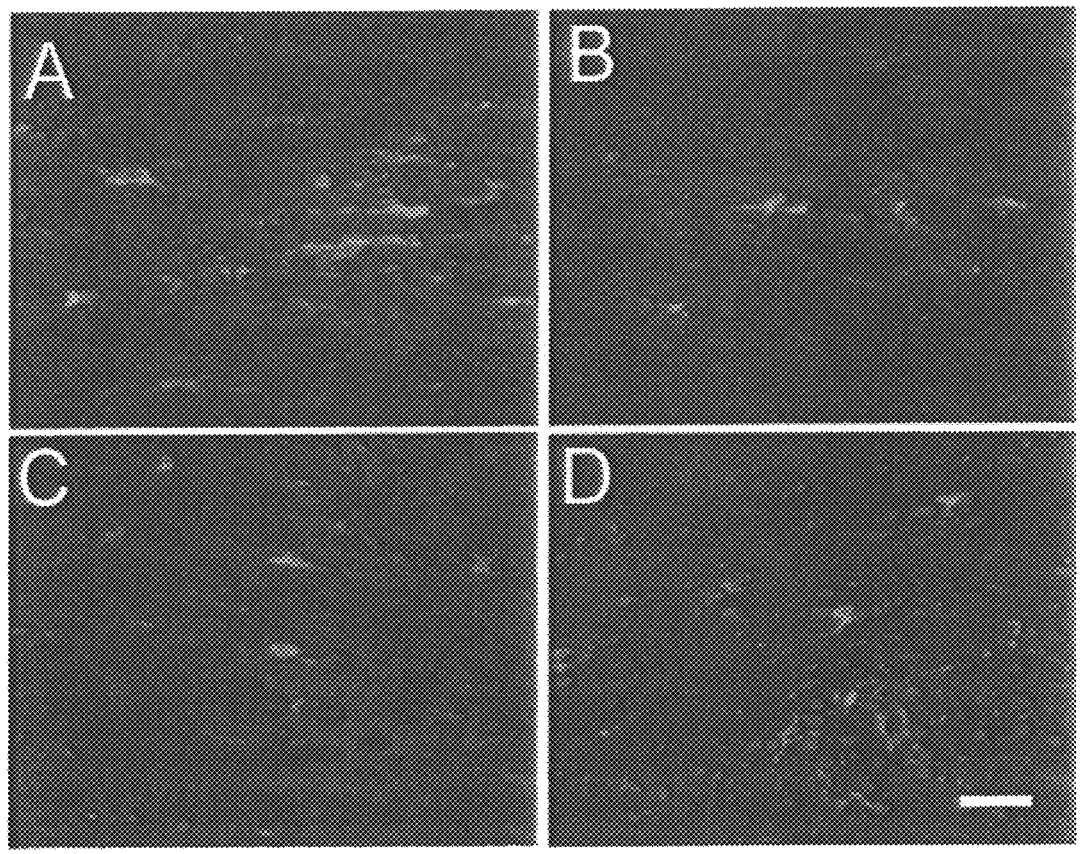
FIG. 6 depicts the immunostaining of NG2 positive OPCs in the corpus callosum of DOX+ and DOX− mice treated with curpizone. (A) NG2 immunostaining in the corpus callosum of DOX+ double transgenic mice at 6 weeks and (B) 8 weeks. (C) NG2 immunostaining in the corpus callosum of DOX− double transgenic mice at 6 weeks and (D) 8 weeks. Red fluorescence represents NG2 immunoreactivity. Blue fluorescence shows counterstaining with DAPI. Scale bar=24 μm. (E) NG2 positive cells in the corpus callosum of mice treated with cuprizone (n=3), *p<0.05.
Figure 6:
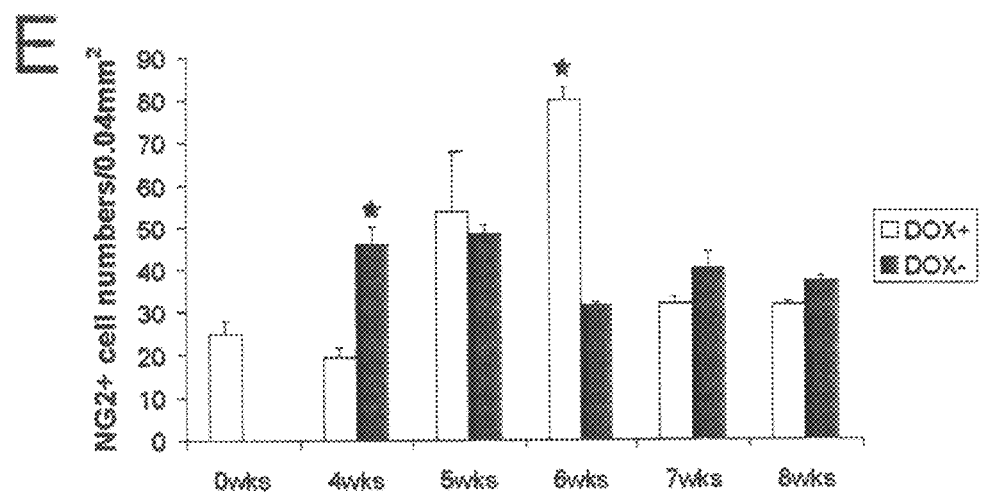

After 6 weeks of cuprizone exposure, the CC1 positive oligodendrocytes began to reappear (42.5±2.1/0.04 mm2) within the demyelinated corpus callosum of control DOX+ mice and reached 228.7±20.2/0.04 mm2 at 8 weeks. However, in the DOX− double transgenic animals there was a dramatic reduction in the number of CC1 positive oligodendrocytes within the corpus callosum at the same point in time (8 weeks) (78±12.7/0.04 mm2). At week 4 of cuprizone treatment, INF-γ increased significantly the number of NG2 positive OPCs in the corpus callosum of the DOX− mice when compared to the number counted in the DOX+ animals (DOX−:46±4.24 versus DOX+: 19±2.12/0.04 mm$^2$; p<0.05). However, at week 6 the DOX− mice had fewer NG2 positive OPCs than the DOX+ mice (DOX− 31.5±0.71 versus DOX+ 80±2.8/0.04 mm$^2$; p<0.05). By weeks 7 and 8, the number of NG2 positive OPCs in the DOX− mice became comparable to that of the DOX+ mice (FIG. 6).

The data indicate that the reduction in the number of CC1 positive oligodendrocytes contributes to the poor remyelination of demyelinated lesions in the presence of IFN-γ, and that IFN-γ delays the recruitment of OPCs to the site of lesion without significantly affecting the number of OPCs that are recruited.

Example 4

INF-γ Inhibits Remyelination in an Animal Model of MS

Double transgenic mice that allow for temporally regulated delivery of INF-γ to the CNS (Lin et al., J Neurosci 24:10074-10083 (2004)) were used to assess the role of INF-γ in the pathogenesis of EAE. GFAP/tTA; TRE/IFN-γ double transgenic mice, as described in Example 1 were used to determine the effect of INF-γ on the demyelination caused by EAE. All mice were fed doxycycline from the day of conception to repress the expression of INF-γ, and were immunized with myelin oligodendrocyte protein (MOG35-55) to induce EAE. At day 7 postimmunization (PID7), doxycycline was withdrawn from the experimental group (PID7 DOX−).

The level of INF-γ was determined in the control (DOX+) and the PID7 DOX− mice using an ELISA immunoassay as described in Example 1, and the severity of the disease was assessed as a function of a clinical score. Clinical severity scores were recorded daily according to a 0-5 point scale, where 0=healthy, 1=flaccid tail, 2=ataxia and/or paresis of hind limbs, 3=paralysis of hind limbs and/or paresis of forelimbs, 4=tetraparalysis, and 5=moribund or dead.

The spinal cord from DOX+ and DOX− animals with EAE was immunostained for MBP, and the remyelination of axons was evaluated. The number of oligodendrocytes was determined in the spine from DOX+ and DOX− mice as the number of CC1 positive cells. Axonal damage was evaluated by immunostaining of non-phosphorylated neurofilament-H. Antibodies to non-phosphorylated neurofilament-H were SMI32 diluted to 1:1000 and obtained from Stemberger Monoclonals.

The results from the ELISA assay showed that the level of INF-γ in both DOX+ and DOX− mice was similar (60 pg/mg) at the peak of the disease PID17. At PID50 the levels of INF-γ were significantly greater in the DOX− mice (40.24 pg/mg) than in the control DOX+ mice (6.22 pg/mg).

Figure 7:
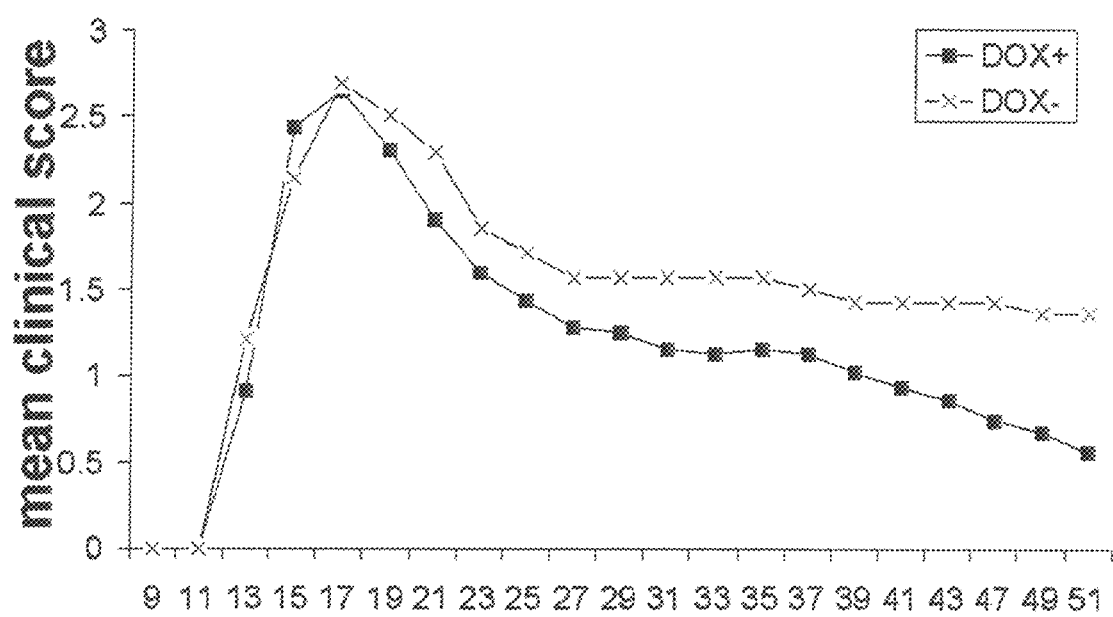
FIG. 7 depicts the clinical score for DOX− and DOX+ mice with EAE during the onset and recovery from the disorder. CNS delivery of INF-γ at the recovery stage of EAE delays disease recovery. Mean clinical score, n=25 for each genotype.

The mean maximum clinical score at PID17 was similar for the DOX+ and DOX− PID17 mice (DOX+: 2.66±0.80 and DOX−: 2.69±0.69, respectively). At this time, twenty of 25 control mice and 24 of 30 DOX− mice developed hind limb paralysis. The control mice began recovering from EAE by day 21, and by day 50 (PID50), the control DOX+ mice were indistinguishable from naive mice. However, at PID50 half of the DOX− mice (12/24) that had developed hind limb paralysis characteristic of EAE, continued to suffer from the paralysis at a time when recovery was seen in the control group (PID50). While the clinical score of control DOX+ mice had decreased to less than 1 at PID 50, the score for the DOX− mice remained at almost 2 (FIG. 7).

Figure 8:
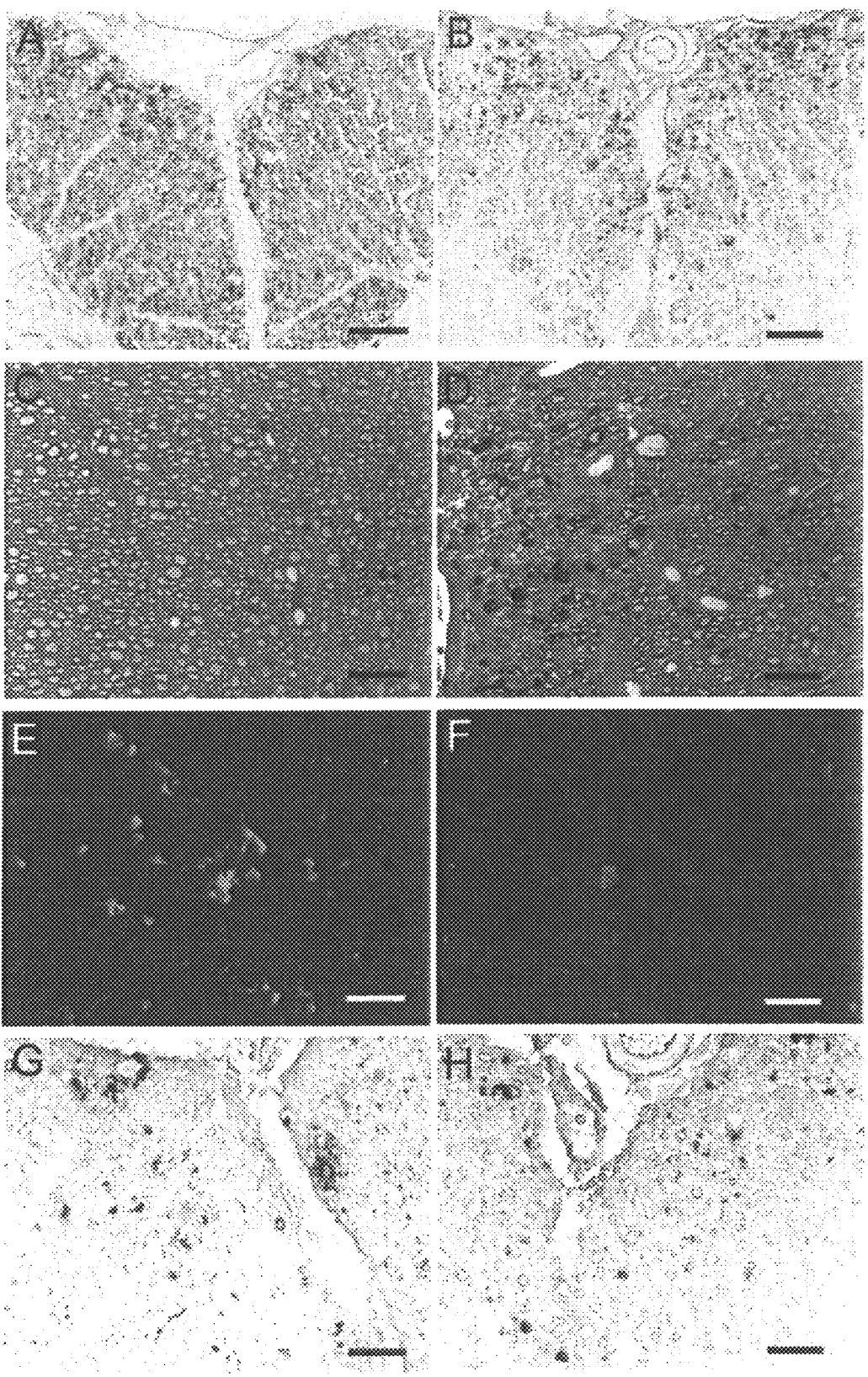
FIG. 8 shows the effect of INF-γ on the CNS during recovery from EAE at PID50. In particular, CNS delivery of INF-γ at the recovery stage of EAE inhibits remyelination at PID50. (A) MBP immunostaining in the lumbar spinal cord of DOX+ mice. (B) MBP immunostaining in the lumbar spinal cord of DOX− mice that had been released from doxycycline at PID7. (C) Toluidine blue staining in the lumbar spinal cord of DOX+ mice. (D) Toluidine blue staining in the lumbar spinal cord of DOX− mice that had been released from doxycycline at PID7. (E) CC1 immunostaining in the lumbar spinal cord of DOX+ mice. (F) CC1 immunostaining in the lumbar spinal cord of DOX− mice that had been released from doxycycline at PID7. (G) non-phosphorylated neurofilament-H immunostaining in the lumbar spinal cord of DOX+ mice. (H) non-phosphorylated neurofilament-H immunostaining in the lumbar spinal cord of DOX− mice that had been released from doxycycline at PID7. The scale bar for panels A and B equals 50 μm; the scale bar for panels C-H equals 25 μm. The red fluorescence shown in panels E and F reflects CC1 immunoreactivity; the blue fluorescence shows the DAPI counterstain. Experiments were done in triplicate.

At PID7, the level of MBP was notably reduced in the lumbar spinal cord of DOX− mice when compared to that of the DOX+ mice (FIGS. 8A and 8B). Toluidine blue staining showed that a large number of axons from the DOX− mice were unmyelinated, while the axons from the DOX+ mice had very few unmyelinated axons (FIGS. 8C and 8D). The number of CC1 positive oligodendrocytes was significantly decreased at PID50 in the DOX− animals (FIGS. 8E and 8F). Immunostaining of non-phosphorylated neurofilament-H was similar in DOX+ and DOX− mice, thus indicating that axonal damage was not affected by INF-γ (FIGS. 8G and 8H).

These data show that INF-γ delays the recovery from EAE, and that the failure to remyelinate caused by INF-γ contributed to the poor recovery of the DOX− mice.

Example 5

INF-γ Enhances the Inflammatory Response in EAE Demyelinating Lesions

INF-γ is known to induce MHC antigens and activate macrophages and T lymphocytes. The inflammatory effect of INF-γ was studied in the CNS during remyelination by determining the infiltration of T cells and macrophages, and measuring the expression of MHC-1, TNF-a, IL-2, IL-12 and IL-17. Immunohistochemistry was performed in tissues from the DOX+ and DOX− mice with EAE as described in Example 4. Experimental procedures were followed as described in the examples above.

Figure 9:
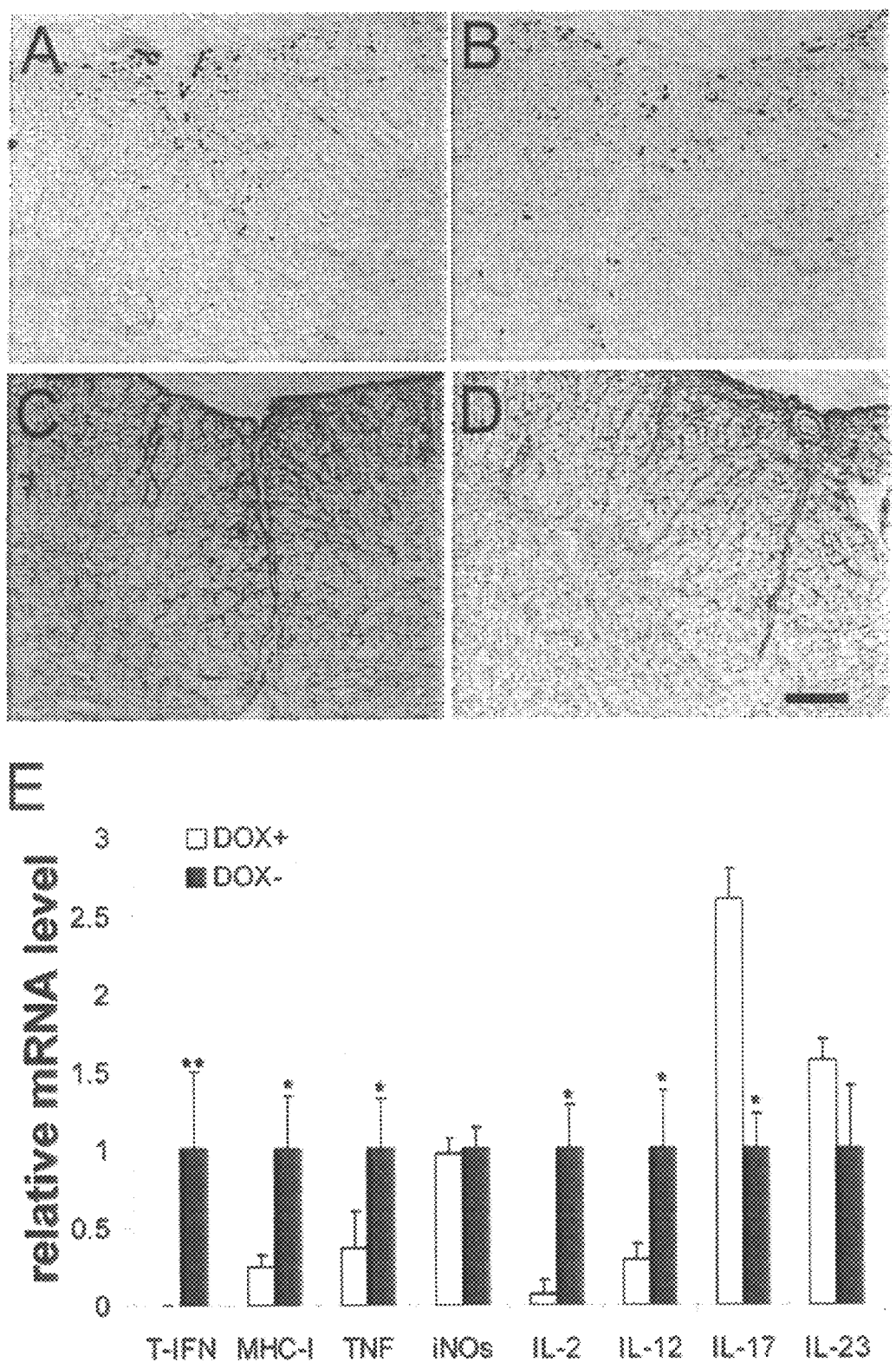
FIG. 9 shows the inflammatory infiltration in demyelinating lesions in the CNS of mice with EAE. CNS delivery of INF-γ at the recovery stage of EAE enhances inflammatory infiltration in demyelination lesions. (A) CD3 immunostaining in the lumbar spinal cord of DOX+ mice. (B) CD3 immunostaining in the lumbar spinal cord of DOX− mice that had been release from doxyxycline at PID7. (C) CD11b immunostaining in the lumbar spinal cord of DOX+ mice. (D) CD11b immunostaining in the lumbar spinal cord of DOX− mice that had been release from doxyxycline at PID7. (E) Real-time PCR analysis of the expression of inflammatory markers in the spinal cord of DOX+ and DOX− mice at PID50. Experiments were done in triplicate; *p<0.05, **p<0.01.

Immunostaining of CD3 (CD3 antibody 1:50; Santa Cruz, Santa Cruz, Calif.) and CD11b (CD11b antibodies 1:50, Chemicon, Tenecula, Calif.) showed that INF-γ did not increase significantly the number of infiltrating T cells and macrophages in the lumbar spinal cord of DOX+ and DOX− mice (FIGS. 9A and B). Real time PCR analysis, revealed that INF-γ increased the expression of MHC-1, TNF-a, IL2 and IL-12, and decrease the expression of IL-17, in DOX− mice when compared to the DOX+ animals. INF-γ did not alter the expression of iNOs and IL-23 (FIG. 9E). The probes and primers that were used are: MHC-I sense primer: ATTC-CCCAAAGGCCCATGT (SEQ ID NO: 1)

MHC-I antisense primer: GTCTCCACAAGCTCCAT-GTCC (SEQ ID NO: 2)

MHC-I probe: TGCTGGGCCCTGGGCTTCTACC (SEQ ID NO: 3); TNF-α sense primer GGCAGGTTCTGTC-CCTTTCA (SEQ ID NO: 13), TNF-α antisense primer ACCGCCTGGAGTTCTGGA (SEQ ID NO: 14), TNF-α probe CCCAAGGCGCCACATCTCCCT (SEQ ID NO: 15); IL-2 sense primer CTACAGCGGAAGCACAGCAG (SEQ ID NO: 16), IL-2 antisense primer ATTTGAAGGTGAG-CATCCTGGG (SEQ ID NO: 17), IL-2 probe AGCAGCAG-CAGCAGCAGCA (SEQ ID NO: 18); IL-12 sense primer CTCTATGGTCAGCGTTCCAACA (SEQ ID NO: 19), IL-12 antisense primer GGAGGTAGCGTGATTGACA-CAT (SEQ ID NO: 20), IL-12 probe CCTCACCCTCG-GCATCCAGCAGC (SEQ ID NO: 21); IL-17 sense primer ATGCTGTTGCTGCTGCTGAG (SEQ ID NO: 22), IL-17 antisense primer TTTGGACACGCTGAGCTTTGAG (SEQ ID NO: 23), IL-17 probe CGCTGCTGCCTTCACTGTAGC-CGC (SEQ ID NO: 24); IL-23 sense primer CTTCTCCGT-TCCAAGATCCTTCG (SEQ ID NO: 25), IL-23 antisense primer GGCACTAAGGGCTCAGTCAGA (SEQ ID NO: 26), IL-23 probe TGCTGCTCCGTGGGCAAAGACCC (SEQ ID NO: 27); inducible nitric oxide synthase (iNOs) sense primer GCTGGGCTGTACAAACCTTCC (SEQ ID NO: 28), iNOs sense primer TTGAGGTCTAAAGGCTC-CGG (SEQ ID NO: 29), iNOS probe TGTCCGAAGCAAA-CATCACATTCAGATCC (SEQ ID NO: 30).

These data indicate that INF-γ modestly enhances the immune response in demyelinated lesions at the recovery stage of EAE, and might thereby contribute to the remyelination failure elicited by this cytokine.

Example 6

Repression of remyelination by IFN-γ is associated with ER stress. Oligodendrocytes have been shown to be highly sensitive to disruption of protein synthesis and perturbation of the secretory pathway (Pfeiffer, et al. (1993) *Trends Cell Biol.* 3: 191-197; Southwood, et al. (2002) *Neuron* 36: 585-596; Leegwater, et al. (2001) *Nat. Genet.* 29: 383-388). To determine whether IFN-γ interferes with endoplasmic reticulum (ER) function in remyelinating oligodendrocytes, the expression of ER stress markers was monitored in the corpus callosum of mice expressing IFN-γ. The study was performed using the transgenic mice described in Example 1.

The level of mRNA encoding ER stress associated genes binding immunoglobulin protein/78 KDa glucose regulated protein (BIP/GRP78) and the CAATT enhancer-binding protein homologous protein/growth and DNA damage protein 153 (CHOP/GADD153), was determined using real time PCR, as described in Example 1 in the corpus callosum of the cuprizone treated mice of Example 1. The probes, sense and antisense primers that were used were:

BIP sense primer: ACTCCGGCGTGAGGTAGAAA (SEQ ID NO: 31);

BIP antisense primer: AGAGCGGAACAGGTCCATGT (SEQ ID NO: 32);

BIP probe TTCTCAGAGACCCTTACTCGGGC-CAAATT (SEQ ID NO: 33);

CHOP sense primer: CCACCACACCTGAAAGCAGAA (SEQ ID NO: 34);

CHOP antisense primer: AGGTGCCCCCAATTTCATCT (SEQ ID NO: 35); CHOP probe TGAGTCCCTGC-CTTTCACCTTGGAGA (SEQ ID NO: 36).

The level of phosphorylated eIF-2α, which inhibits nucleotide exchange on the eIF-2 complex and attenuates most protein synthesis, was analyzed by Western blot, and the expression was colocalized by immunostaining CC1 antibodies as described above. Western blot analysis was performed as follows. The corpus callosum from 3 mice was rinsed in ice cold phosphate-buffered saline (PBS) and pooled, and immediately homogenized in 5 volumes of Triton X-100 buffer (20 mM HEPES pH 7.5, 150 mM NaCl, 1% Triton X-100, 10% glycerol, 1 mM EDTA, 10 mM tetrasodium pyrophosphate, 100 mM NaF, 17.5 mM β-glycerophosphate, 10 mM phenylmethylsulfonyl fluoride, 15 μg/ml aprotinin, and 6 μg/ml pepstatin A) using a motorized homogenizer. After incubation on ice for 15 min, the extracts were cleared by centrifugation at 14,000 rpm twice for 30 min each. The protein content of each extract was determined by protein assay (Bio-Rad). The extracts (40 μg) were separated by sodium dodecyl sulfate-polyacrylamide gel electrophoresis and transferred to nitrocellulose. The blots were incubated with primary antibody (see below), and the signal was revealed by chemiluminescence after reacting with horseradish peroxidase-conjugated second antibody. The following primary antibodies were used: anti-eIF-2α (1:500; Santa Cruz, Santa Cruz, Calif.), anti-p-eIF-2α (1:1000, Cell signaling Technology), anti-CHOP (1:500; Santa Cruz) and anti-actin (1:1000; Sigma, St Louis, Mo.).

Figure 10:
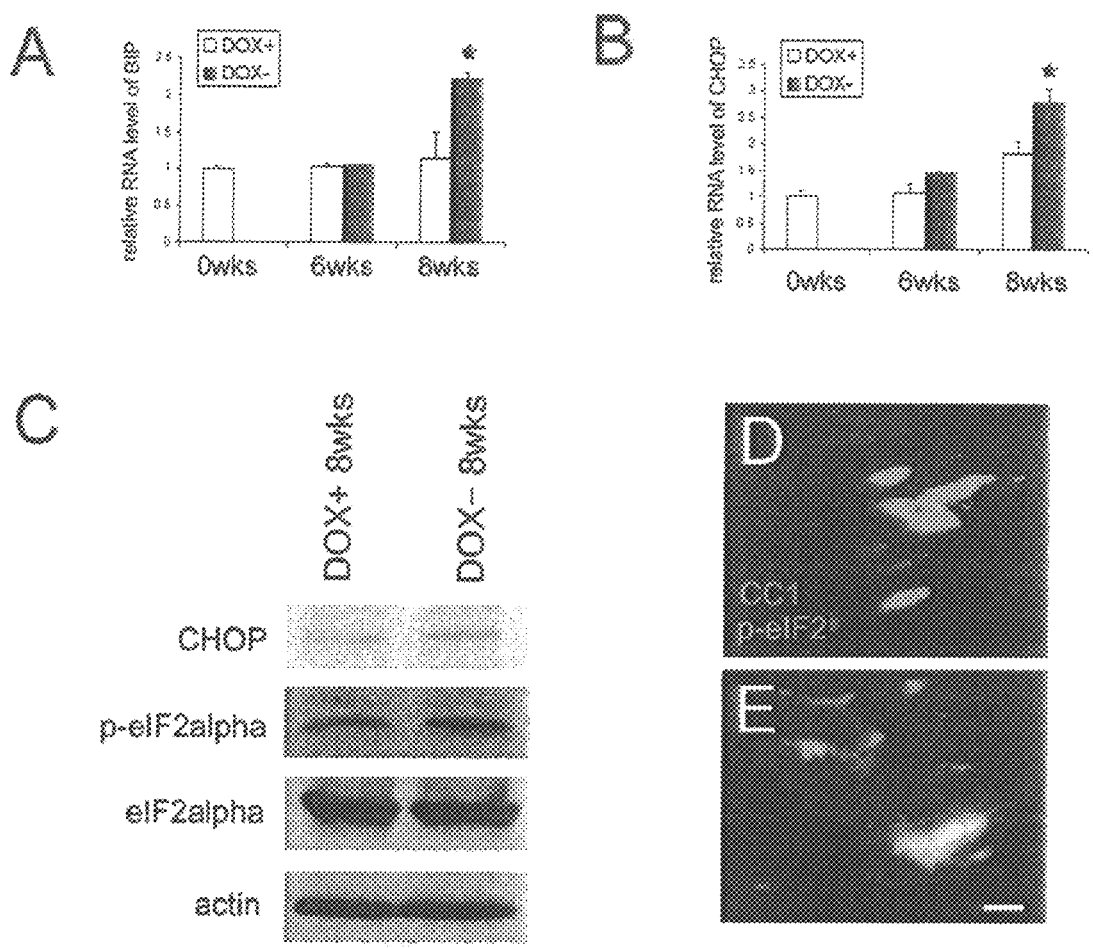
FIG. 10 depicts the effect of INF-γ on the expression ER stress markers during remyelination. Real time PCR analysis of BIP mRNA (A) and CHOP mRNA (B) in the corpus callosum of DOX+ and DOX− mice in which demyelination had been induced with cuprizone (n=3; *p<0.05). (C) Western blot analysis of the expression of CHOP, p-eIF-1α, eIF-2α relative to actin in the corpus callosum of the DOX+ and DOX− mice in (A). Double immunostaining of CC1 and p-eIF-2α in the corpus callosum of DOX+ (D) and DOX− (E) mice at week 8. Panels D and E: n=3, scale bar=10 μm; red fluorescence reflects CC1 immunoreactivity, green fluorescence reflects p-eIF-2α immunoreactivity. The detrimental effect of INF-γ on remyelination is associated with ER stress.

The level of mRNA for BIP and CHOP, which are associated with the ER stress response, were increased approximately 2 fold in the corpus callosum of DOX− double transgenic mice compared to control DOX+ animals (FIGS. 10A and 10B). Elevated levels of the CHOP protein, approximately 1.7 fold, were also observed in the corpus callosum of DOX− double transgenic mice by Western blot analysis (FIG. 10C). Western blot analysis also revealed that IFN-γ elevated the level of phosphorylated eIF-2α (p-eIF-2α) by approximately 1.8 fold in the corpus callosum (FIG. 10C) of the same DOX− animals. Furthermore, colocalization analysis using the CC1 antibody revealed that remyelinating oligodendrocytes displayed increased levels of p-eIF-2α (FIGS. 10D and 10E).

These results indicate that the detrimental effect of IFN-γ on remyelination is associated with the activation of the ER stress pathway.

Example 7

PERK Modulates the Severity of the Reduction in Remyelination Induced by IFN-γ

The involvement of the ER stress response in the reduction caused by IFN-γ to remyelinate lesions was examined in transgenic mice that were generated to be heterozygous for a loss of function mutation in pancreatic ER kinase (PERK) (Harding, et al., (2001) Mol Cell 7:1153-1163), and to be temporally regulated for expressing INF-γ in the CNS. TRE/IFN-γ mice were first crossed with PERK+/− mice (Harding, et al. (2001) *Mol. Cell* 7: 1153-1163) on the C57BL/6 background to generate mice the carry the PERK mutation, and the resulting progeny were crossed to GFAP/tTA mice to obtain transgenic mice that were heterozygous for the PERK mutation. The effect of PERK on remyelination in the presence or absence of INF-γ was evaluated as evaluated as a function of the level of myelination of oligodendrocytes in remyelinating lesions and the number of oligodendrocytes present in the remyelinating lesion.

The extent of remyelination was assessed as described in the previous examples in the corpus callosum of PERK+/+ and PERK+/− mice that were made to express INF-γ (DOX− PERK+/+ and DOX− PERK+/−), and in mice in which the expression of INF-γ was repressed (DOX+ PERK+/+ and DOX+ PERK+/−). Remyelination was determined by electron microscopy, and was related to the number of CC1 positive oligodendrocytes and the level of caspase-3 expression in the corpus callosum of all animals. The level of caspase-3 was determined by immunohistochemical methods using anti capsase antibody (active-casoase-3 antibody, 1:50; Cel Signaling Technology) and according to the method described in Example 1. Demyelination was induced in six-week-old GFAP/tTA; TRE/IFN-γ double transgenic mice on a PERK+/− background that had been maintained on doxycycline, by simultaneously treating the mice with 0.2% cuprizone and releasing them from doxycycline (DOX− PERK+/−). Remyelination was allowed to occur by withdrawing cuprizone at week 6.

Figure 11:
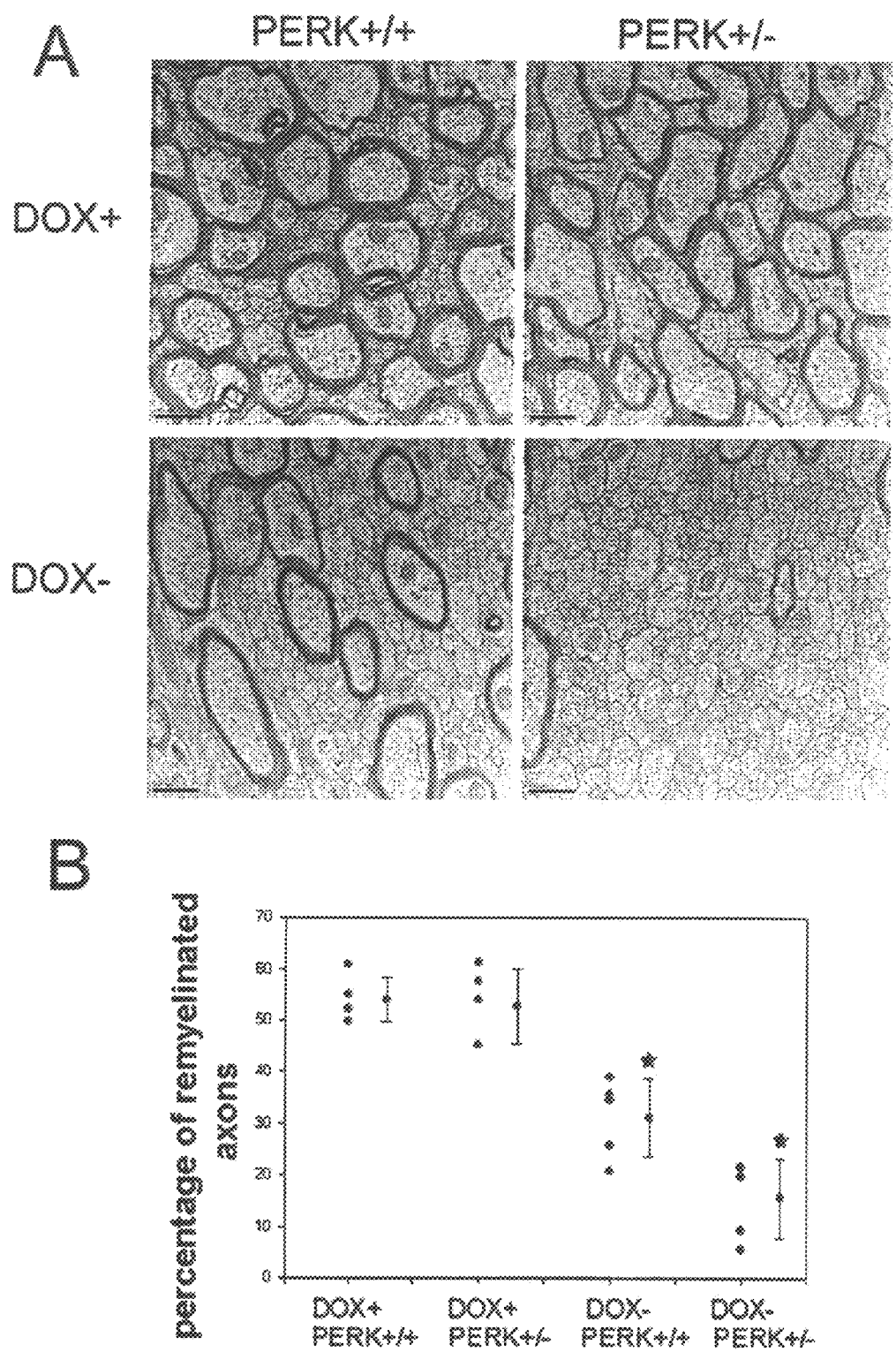
FIG. 11 shows comparisons of the state of remyelination in the corpus callosum of DOX+ and DOX− mice that are wild type or are heterozygous for a mutation in the PERK enzyme (PERK+/−). (A) Electron micrographs of the corpus callosum at week 9; n=5, scale bar=0.5 μm. (B) Graph showing the percent remyelinated axons in 5 mice at week 9, *p<0.01.

Immunohistochemistry and EM analysis of CC1 positive oligodndrocytes revealed that a loss of function in PERK did not affect the demyelination process during cuprizone treatment (data not shown). In contrast, GFAP/tTA; TRE/IFN-γ; PERK+/− mice that were released from doxycycline at the time of cuprizone exposure (DOX− PERK+/−) had significantly fewer remyelinated axons at 9 weeks (15.6%±7.6%, FIG. 11), 3 weeks after cuprizone was removed from the diet, than the double transgenic mice on a PERK+/+ background (DOX− PERK+/+) (54.0%±4.3% vs 31.1%±7.6%; p<0.01). Mice that had been continuously maintained on doxycycline (DOX+ PERK+/− and DOX+ PERK+/+) had significantly more (54%) remyelinated axons than the DOX− mice (FIG. 11).

Figure 12:
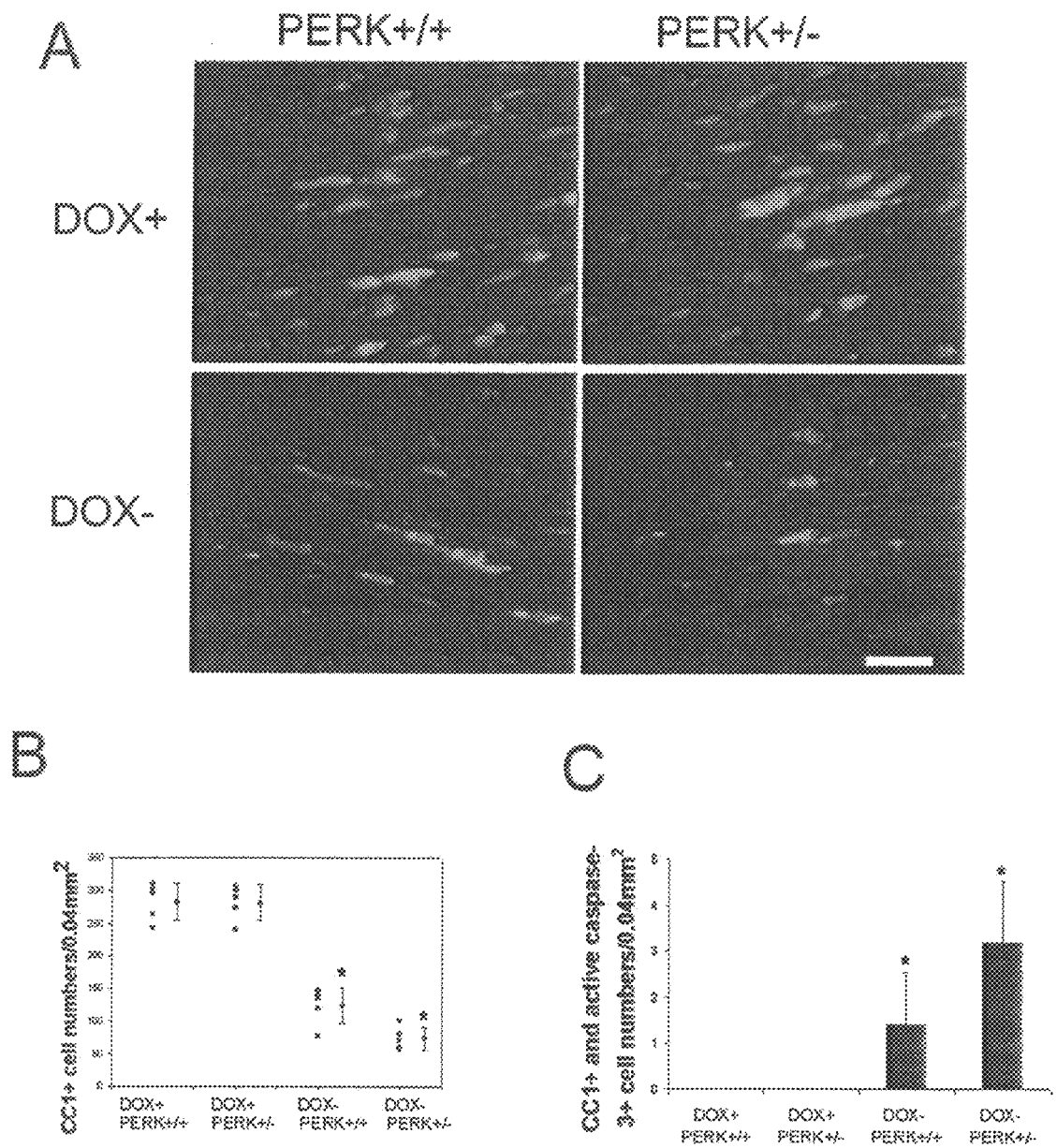
FIG. 12 shows a comparison of the number of oligodendrocytes in the corpus callosum of DOX+ and DOX− mice that are wild type or are heterozygous for a mutation in the PERK enzyme (PERK+/−). (A) Immunostaining of CC1 oligodendrocytes in mice at week 9; the red fluorescence reflects the CC1 cells, and the blue stain is the DAPI counterstain; n=5, scale bar=25 μm. (B) Graph showing the number of CC1 positive oligodendrocytes in mice at week 9, n+5, *p<0.01. (C) Graph showing the number of CC1 and caspase-3 positive oligodendrocytes in mice at week 9, n=5, p<0.05.

The number of CC1 positive oligodendrocytes that was significantly lower (123.2±27.5/0.04 mm$^2$) in the DOX− PERK+/+ mice than in the DOX+ PERK+/+ animals (283.2±27.7/0.04 mm$^2$; p<0.01; FIGS. 12A and B), and only a few oligodendrocytes were detected in the corpus callosum of the DOX− PERK+/− mice (FIGS. 12A and B). In addition, the number of oligodendrocytes that stained positive for caspase-3 was 2.3 times greater in the DOX− PERK+/− than in the DOX− PERK+/+ mice (FIG. 12C).

These data indicate that ER stress response is associated with the failure to remyelinate and the reduction of oligodendrocyte numbers elicited by IFN-γ, and that PERK is essential for remyelination during ER stress.

Example 8

Apoptosis of Oligodendrocytes that is Induced by INF-γ is Associated with ER Stress In Vitro To test whether apoptosis of oligodendrocytes that is induced by INF-γ affects ER stress, the effect on the morphology, the degree of apoptosis and the expression of ER markers was studied in a culture of oligodendrocyte precursor cells (OPC). Oligodendrocyte progenitors were cultured from neonatal rat brains (Baerwald, et al. (1998) *J. Neurosci. Res.* 52: 230-239). A mixed glial culture was grown in flasks in medium containing 10% fetal bovine serum (FBS), and when the astrocyte layer became confluent (10-14 days), oligodendrocyte progenitors were separated from astrocytes and microglia using an orbital shaker. Cells, greater than 95% of which were A2B5 positive, GFAP negative and CD11b negative, were cultured in 0.5% FBS containing medium, which also contained PDGF (10 ng/ml) and FGF (5 ng/ml) (both from R&D Systems, Minneapolis, Minn.). Then cells were switched to 0.5% FBS medium without PDGF and FGF for differentiation. After 5 days in the differentiating medium, approximately 40% of cells were positive for myelin protein 2'3'-cyclic nucleotide 3'-phosphodiestaerase (CNP). 70 U/ml recombinant rat IFN-γ (Calbiochem, La Jolla, Calif.) was added to the cells that had been allowed to differentiate for 5 days. After 5 d in the differentiating medium, about 40% of the cells were CNP positive. 70 U/ml of recombinant rat INF-γ (Calbiochem) was added to the cells that had been allowed to differentiate for 5d. To examine the oligodendroglial response to general ER stress-inducing agents, progenitor cells that had been cultured in differentiation medium for 5 or 7 days were treated with 2 μg/ml of tunicamycin (Sigma Aldrich) for 6 hours.

The level of apoptosis of the OPC cells was determined by double staining CNP (1:200; Stemberger Monoclonals, Lutherville, Md.) and TUNEL using the ApopTag Kit (Serologicals Corp., Norcross, Calif.) and following the manufacturer's instructions. Apoptosis was also evaluated by measuring the activity of caspase-3 in oligodendrocyte lysates using the Fluorimetric Caspase 3 Assay Kit (Sigma, St. Louis, Mo.), according to the manufacturer's instructions.

To determine whether INF-γ affects ER function, the RNA expression of ER markers binding immunoglobulin protein (BIP), CAAT enhancer binding protein homologous protein (CHOP), and caspase 12 was determined using real time PCR. RNA was isolated from cultured cells and mice brain using Trizol reagent (Invitrogen, Carlsbad, Calif.) and treated with DNAaseI (Invitrogen) to eliminate genomic DNA. Reverse transcription was performed using Superscript First Strand Synthesis System for RT-PCR kit (Invitrogen). Real-time PCR was performed with iQ Supermix (Bio-Rad, Hercules, Calif.) on a Bio-Rad iQ real-time PCR detection system (Bio-Rad). The following primers and probes (Integrated DNA Technologies Inc., Coralville, Iowa) for real-time PCR were used: mouse CHOP sense primer CCACCACACCT-GAAAGCAGAA (SEQ ID NO: 34); mouse CHOP antisense primer AGGTGCCCCCAATTTCATCT (SEQ ID NO: 35); CHOP probe TGAGTCCCTGCCTTTCACCTTGGAGA (SEQ ID NO: 36); mouse BIP sense primer ACTCCGGCGT-GAGGTAGAAA (SEQ ID NO: 31); mouse BIP antisense primer AGAGCGGAACAGGTCCATGT (SEQ ID NO: 32); BIP probe TTCTCAGAGACCCTTACTCGGGCCAAATT (SEQ ID NO: 33); mouse caspase 12 sense primer ATGCT-GACAGCTCCTCATGGA (SEQ ID NO: 37); and mouse caspase antisense primer TGAGAGCCAGACGTGTTCGT (SEQ ID NO: 38).

To determine the effect of INF-γ on the level of phosphorylated eIF-2α and caspase 12 proteins, western blot analysis was performed using the following antibodies anti-eIF-2α (1:500; Santa Cruz), anti-p-eIF-2α (1:1000, Cell signaling Technology), anti-caspase-12 (1:500; Santa Cruz) and anti-actin (1:1000; Sigma, St Louis, Mo.), and according to the following protocol. Tissues or cultured cells were rinsed in ice cold phosphate-buffered saline (PBS) and then immediately homogenized in 5 volumes of Triton X-100 buffer (20 mM HEPES pH 7.5, 150 mM NaCl, 1% Triton X-100, 10% glycerol, 1 mM EDTA, 10 mM tetrasodium pyrophosphate, 100 mM NaF, 17.5 mM β-glycerophosphate, 10 mM phenylmethylsulfonyl fluoride, 15 μg/ml aprotonin, and 6 μg/ml pepstatin A) using a motorized homogenizer. After incubation on ice for 15 min, the extracts were cleared by centrifugation at 14,000 rpm twice for 30 min each. The protein content of each extract was determined by protein assay (Bio-Rad). The extracts (40 μg) were separated by sodium dodecyl sulfate-polyacrylamide gel electrophoresis and transferred to nitrocellulose. The blots were incubated with primary antibody (see below), and the signal was revealed by chemiluminescence after reacting with horseradish peroxidase-conjugated second antibody.

Figure 13:
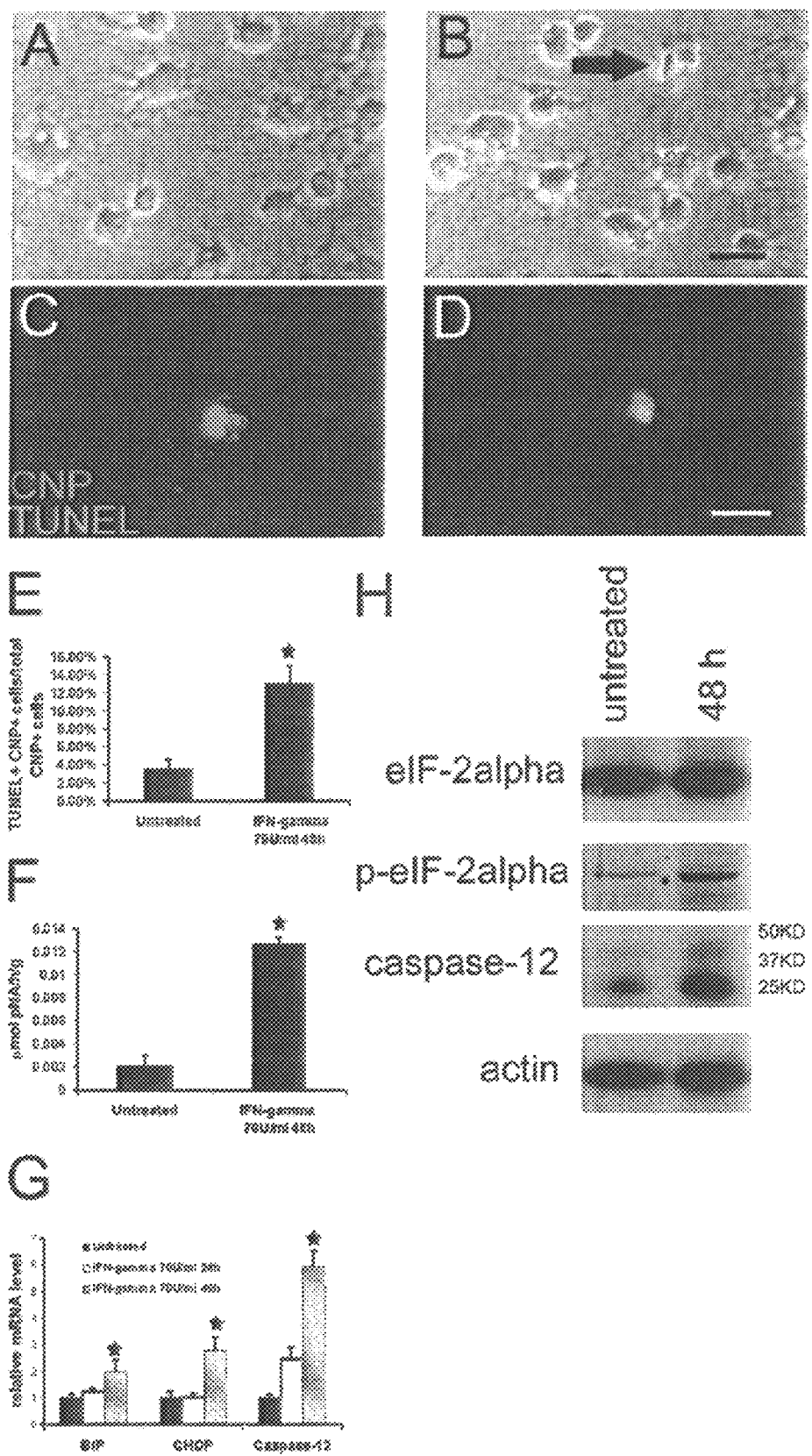
FIG. 13 shows that IFN-γ-induced apoptosis in cultured rat oligodendrocytes is associated with ER stress. (A) Untreated oligodendrocytes that underwent differentiation for 7 days. (B) Oligodendrocytes that underwent differentiation for 5 days and treatment with 70 U/ml IFN-γ for 48 h, revealing cell shrinkage and aggregation of cell bodies (arrow). (C) TUNEL and CNP double labeling for untreated oligodendrocytes that underwent differentiation for 7 days. (D) TUNEL and CNP double labeling for oligodendrocytes that underwent differentiation for 5 days and treatment with 70 U/ml IFN-γ for 48 h. (E) Quantitation of TUNEL and CNPase double positive cells, *p<0.05. (F) Caspase-3 activity assay in the oligodendrocyte lysates, *p<0.01. (G) Real-time PCR analyses of the expression of BIP, CHOP and caspase-12 in oligodendrocytes treated with 70 U/ml IFN-γ, *p<0.05. (H) Western blot analyses of total eIF-2α, p-eIF-2α and caspase-12 in oligodendrocytes treated with 70 U/ml IFN-γ. All experiments were repeated at least 3 times. Scale bars=30 μM in panels A and B, Scale bars=20 μM in panels C and D.

Purified oligodendrocyte progenitor cells (OPCs) were allowed to differentiate for five days in defined media, at which point approximately 40% of the cells expressed the myelin protein 2'3'-cyclic nucleotide 3'-phosphodiesterase (CNP) and extended branched processes (FIGS. 13A and 13C). These cells did not extend the flat membrane sheets that are characteristic of more mature oligodendrocyte cultures. When treated with 70 U/ml IFN-γ for 48 h these cells showed abnormal morphological changes; including cell shrinkage and aggregation of cell bodies, followed by detachment from the culture plate (FIGS. 13A and 13B). Terminal deoxynucleotidyl transferase (TdT) dUTP nick-end labeling (TUNEL) and CNP double labeling revealed that IFN-γ induced apoptosis in a significant number of oligodendrocytes (FIGS. 13C, 13D and 13E). Furthermore, the caspase-3 activity in the cell lysates of IFN-γ-treated oligodendrocytes was markedly increased (FIG. 13F). Thus, 70 U/ml of IFN-γ is able to induce apoptosis in oligodendrocytes that are actively synthesizing myelin components.

To determine whether IFN-γ interferes with ER function, the expression of markers of ER stress were monitored in cytokine treated oligodendrocyte cultures. The levels of mRNA encoding the binding immunoglobulin protein/78 KDa glucose regulated protein (BIP/GRP78) and the CAATT enhancer-binding protein homologous protein/growth and DNA damage protein 153 (CHOP/GADD153), both of which are associated with the ER stress response, were increased approximately 2 to 3 times in oligodendrocytes after exposure to IFN-γ (FIG. 13G). The phosphorylation of eIF-2α, which inhibits nucleotides exchange on the eIF-2 complex and attenuates most protein synthesis, occurs within minutes following the development of ER stress (Ron, 2002). Western blot analysis revealed that IFN-γ significantly elevated the level of phosphorylated eIF-2α (p-eIF-2α) in oligodendroglial cultures (FIG. 13H). Caspase-12, an ER-localized caspase, is activated by ER stress and can lead to cleavage of caspase-3 (Nakagawa, et al. (2000) Nature 403: 98-103; Lamkanfi, et al. (2004) Cell Death Differ. 11: 365-368). The induction of caspase-12 was observed after treatment of oligodendrocytes with IFN-γ (FIG. 13G). Moreover, the level of the active fragment of caspase-12 was strongly elevated after 48 h of IFN-γ treatment (FIG. 13H). These results indicate that IFN-γ-induced apoptosis in cultured oligodendrocytes is associated with the activation of the ER stress pathway.

Forty percent of the purified oligodendrocyte progenitor cells (OPCs) that had been allowed to differentiate for five days in defined media expressed the myelin protein 2'3'-cyclic nucleotide 3'-phosphodiesterase (CNP) and extended branched processes (FIGS. 13A and 13C). These cells did not extend the flat membrane sheets that are characteristic of more mature oligodendrocyte cultures. When treated with 70 U/ml IFN-γ for 48 h these cells showed abnormal morphological changes; including cell shrinkage and aggregation of cell bodies, followed by detachment from the culture plate (FIGS. 13A and 13B). Terminal deoxynucleotidyl transferase (TdT) dUTP nick-end labeling (TUNEL) and CNP double labeling revealed that IFN-γ induced apoptosis in a significant number of oligodendrocytes (FIGS. 13C, 13D and 13E). Furthermore, the caspase-3 activity in the cell lysates of IFN-γ-treated oligodendrocytes was markedly increased (FIG. 13F).

These data indicate that IFN-γ is able to induce apoptosis in oligodendrocytes that are actively synthesizing myelin components.

To determine whether IFN-γ interferes with ER function, the expression of markers of ER stress were monitored in cytokine treated oligodendrocyte cultures. The levels of mRNA encoding the binding immunoglobulin protein/78 KDa glucose regulated protein (BIP/GRP78) and the CAATT enhancer-binding protein homologous protein/growth and DNA damage protein 153 (CHOP/GADD 153), both of which are associated with the ER stress response, were increased approximately 2 to 3 times in oligodendrocytes after exposure to IFN-γ (FIG. 13G). The phosphorylation of eIF-2α, which inhibits nucleotides exchange on the eIF-2 complex and attenuates most protein synthesis, occurs within minutes following the development of ER stress (Ron, 2002). Western blot analysis revealed that IFN-γ significantly elevated the level of phosphorylated eIF-2α (p-eIF-2α) in oligodendroglial cultures (FIG. 13H). Caspase-12, an ER-localized caspase, is activated by ER stress and can lead to cleavage of caspase-3 (Nakagawa, et al. (2000) Nature 403: 98-103; Lamkanfi, et al. (2004) Cell Death Differ. 11: 365-368). The induction of caspase-12 was observed after treatment of oligodendrocytes with IFN-γ (FIG. 13G). Moreover, the level of the active fragment of caspase-12 was strongly elevated after 48 h of IFN-γ treatment (FIG. 13H).

These results indicate that IFN-γ-induced apoptosis in cultured oligodendrocytes is associated with the activation of the ER stress pathway.

Example 9

Hypomyelination Induced by Ectopic Expression of IFN-γ is Associated with ER Stress To study the effect of INF-γ on the myelination of oligodendrocytes during mouse development, transgenic mice that allow for temporally regulated delivery of IFN-γ to the CNS using the tetracycline (tet) controllable system (Lin, et al. (2004) J. Neurosci. 24: 10074-10083) were generated. To drive tTA expression in astrocytes, the transcriptional regulatory region of the glial fibrillary acidic protein (GFAP) gene was chosen (Brenner, et al. (1994) J. Neurosci. 14: 1030-1037). GFAP/tTA mice were mated with TRE/IFN-γ mice to produce animals hemizygous for both transgenes. When these mice are maintained on doxycycline (DOX+), expression of the IFN-γ transgene is repressed (FIG. 10A); when the double transgenic mice are released from doxycycline (DOX−) INF-γ is expressed. For the purpose of these experiments, mice received doxycycline up to day 14 of development (E14), at which time the experimental animals (DOX−) stopped receiving doxycycline, while the control animals (DOX+) were continuosly fed the dug. The mRNA for IFN-γ could be detected in the DOX− mice as early as 10 days after birth (data not shown).

Real time PCR analysis was performed to determine the levels of expression of INF-γ, MHC-1, BIP, CHOP, and caspase 12. The primers for the PCR reactions for BIP, CHP and caspase 12 are given in example 1. The sense and antisense primers for INF-γ were GATATCTCGAGGAACTG-GCAAAA (SEQ ID NO: 39) and CTTCAAAGAGTCT-GAGGTAGAAAGAGATAAT (SEQ ID NO: 40), respectively; and the sense and antisense primers for MHC-1 were MHC-I sense primer: ATTCCCCAAAGGCCCATGT (SEQ ID NO: 1); and MHC-I antisense primer: GTCTCCA-CAAGCTCCATGCC (SEQ ID NO: 2).

Western blot analysis was performed on the CNS of 14 day old mice to determine the expression of caspase-12 as described in Example 6.

Brain and spinal cord tissue were analyzed using immunohistochemical methods as follows. Anesthetized mice were perfused through the left cardiac ventricle with 4% paraformaldehyde in 0.1M PBS. The half-saggital brains and transcervical spinal cord were removed, postfixed with paraformaldehyde, cryopreserved in 30% sucrose, embedded in OCT and frozen on dry ice. Frozen sections were cut in a cryostat at a thickness of 10 μm. Coronal sections at the fornix region of the corpus callosum corresponding to Sidman sections 241-251 were selected for use, and all comparative analyses were restricted to midline corpus callosum (Sidman, et al. (1971) *Atlas of the Mouse Brain and Spinal Cord* (Harvard Univ. Press, Cambridge, Mass.). For immunohistochemistry, frozen sections were treated with −20° C. acetone, blocked with PBS containing 10% NGS and 0.1% Triton X-100 and incubated overnight with the primary antibody diluted in blocking solution. Appropriate fluorochrome- or enzyme-labeled secondary antibodies (Vector Laboratories, Burlingame, Calif.) were used for detection. An antibody against CC1 (APC7, 1:50; EMD Biosciences, Inc., La Jolla, Calif.) was used as a marker for mature oligodendrocytes. Antibody against MBP (1:1000; Sternberger Monoclonals, Lutherville, Mass.) was used to verify the degree of myelination. Antibody against active-caspase-3 (1:50, Cell signaling Technology, Beverly, Mass.) was used as a marker for apoptotic cells. Fluorescent stained sections were mounted with Vectashield mounting medium with DAPI (Vector Laboratories) and visualized with a Zeiss Axioplan fluorescence microscope. Images were captured using a Photometrics PXL CCD camera connected to an Apple Macintosh computer using the Open Lab software suite. Immunopositive cells were quantified by counting positive cells within the median of the corpus callosum, confined to an area of 0.04 mm$^2$. Only those cells with nuclei observable by DAPI staining were counted. Each MBP immunostaining slide was scored on a scale of zero to four. A score of zero indicates complete demyelination, and a score of four indicates normal myelination in the corpus callosum of adult mice.

Figure 14:
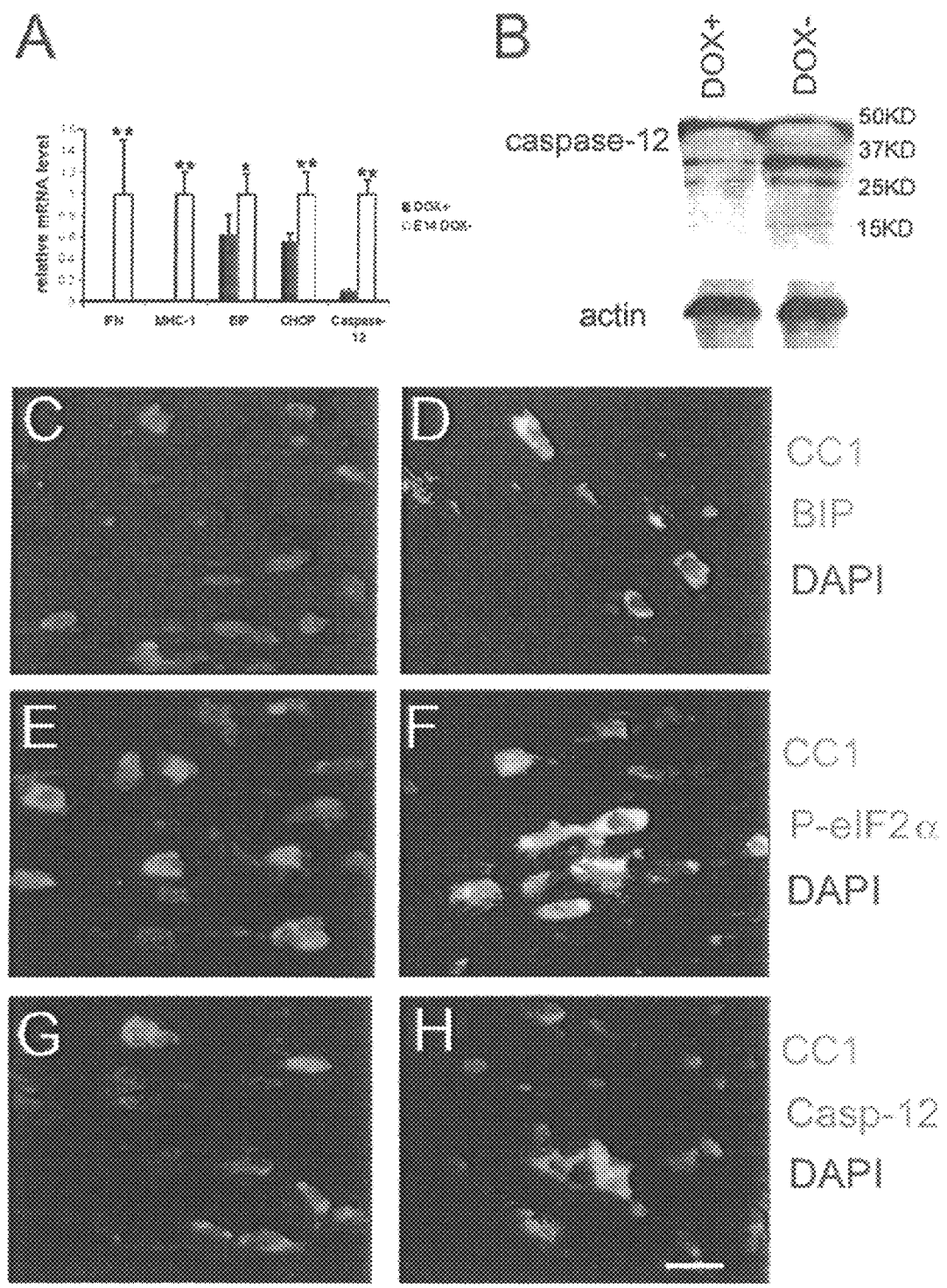
FIG. 14 shows that hypomyelination induced by ectopically expressed IFN-γ is associated with ER stress. (A) Real-time PCR analyses for detection of mRNA in the brain of 14-day-old mice ectopically expressing IFN-γ (n=3), *p<0.05, **p<0.01. (B) Western blot analyses for caspase-12 in the CNS of 14-day-old double transgenic mice released from doxyclycline at E 14. (C) BIP and CC1 double immunostaining in the spinal cord of 14-day-old double transgenic mice that received doxycycline. (D) BIP and CC1 double immunostaining in the spinal cord of 14-day-old double transgenic mice released from doxycycline at E 14. (E) p-eIF-2α and CC1 double immunostaining in the spinal cord of 14-day-old double transgenic mice that received doxycycline. (F) p-eIF-2α and CC1 double immunostaining in the spinal cord of 14-day-old double transgenic mice released from doxycycline at E 14. (G) Caspase-12 and CC1 double immunostaining in the spinal cord of 14-day-old double transgenic mice that received doxycycline. (H) Caspase-12 and CC1 double immunostaining in the spinal cord of 14-day-old double transgenic mice released from doxycycline at E 14. Panels C, D, E, F, G and H: n=3, scale bar=30 μM.

Real-time PCR analysis showed that the DOX− mice expressed robust levels of IFN-γ and major histocompatibility complex (MHC) class I, a downstream target of IFN-γ activity, in the CNS at postnatal day (PND) 14 (FIG. 14A). The double transgenic mice that ectopically expressed IFN-γ (DOX−) in the CNS during development were mildly hypomyelinated (see FIGS. 16 and 17), which is consistent with observations made on transgenic mice that were previously generated to express IFN-γ constitutively in oligodendrocytes (Corbin, et al. (1996) *Mol. Cell. Neurosci.* 7: 354-370). The diminished myelination observed in these mice is correlated with IFN-γ-induced oligodendrocyte apoptosis (see FIGS. 19A and 19F). IFN-γ upregulated BIP and CHOP expression approximately 1.6 and 2 times the control levels and strongly enhanced caspase-12 expression in the CNS of these animals (FIG. 14A). More notably, the level of the active fragment of caspase-12 was also increased in the CNS of these animals (FIG. 14B). Furthermore, colocalization analysis with the CC1 antibody revealed that oligodendrocytes increased expression of BIP (FIGS. 14C and 14D), p-eIF-2α (FIGS. 14E and 14F) and caspase-12 (FIGS. 14G and 14H).

These data support the link between ER stress and IFN-γ-induced oligodendrocyte apoptosis and hypomyelination during development.

Example 10

Hypersensitivity of PERK+/− Mice to Conditional Mis-Expression of IFN-γ

To examine the involvement of the ER stress response induced by INF-γ, the involvement of the PERK enzyme was evaluated using transgenic mice that are heterozygous for a loss of function of mutation in pancreatic ER kinase (PERK) (Harding, et al. (2001) *Mol. Cell* 7: 1153-1163). The phenotype of the transgenic animals was analyzed as a function of the level of p-eIF-2α was evaluated in the PERK+/− mice.

Figure 15:
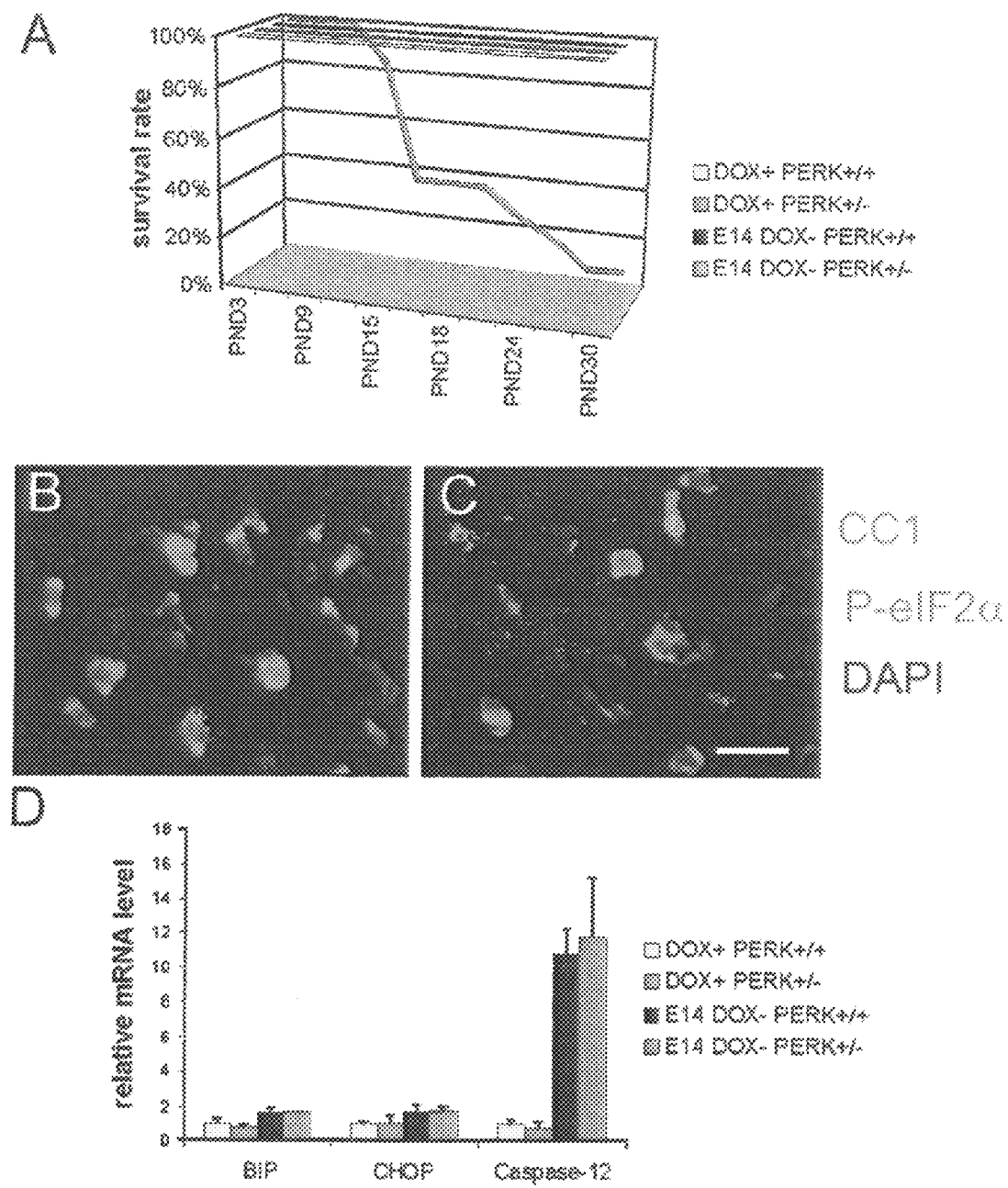
FIG. 15 shows hypersensitivity of PERK+/− mice to conditional mis-expression of IFN-γ. (A) Mouse survival curve (n=40 for each group). (B and C) p-eIF-2α and CC1 double labeling in the spinal cord of 14-d-old GFAP/tTA; TRE/IFN-γ; PERK+/− mice that received doxycycline (B) or were released from doxycycline at E 14 (C). (B and C) n=3; bar, 30 μM. (D) Real-time PCR analyses of mRNA levels in the brain of 14-d-old mice (n=3). Error bars represent standard deviation.

GFAP/tTA and TRE/IFN-γ double transgenic mice described in Example 1 were crossed with PERK+/− mice, and the resulting progeny were intercrossed to obtain double transgenic mice that were homozygous or heterozygous for the PERK mutation The majority of the double transgenic mice with a PERK−/− background died within 12 days after birth, regardless of whether they received doxycycline during the entire period or if doxycycline was interchanged with water at embryonic day 14 (E14). Double transgenic GFAP/tTA; TRE/IFN-γ mice on a PERK+/+ background, released from doxycycline at E14 (E14 DOX− PERK+/+) showed the expected minor tremor and ataxia but good survival. In contrast, the double transgenic mice on a PERK+/− background (E14 DOX− PERK+/−) had a much more severe phenotype. These animals were considerably smaller than IFN-γ expressing PERK+/+ littermates or PERK+/− animals that did not inherit the combination of GFAP/tTA and TRE/IFN-γ alleles, and showed severe tremor and ataxia, and approximately two-thirds of these mice experienced tonic seizures. Strikingly, more than 90% of the double transgenic mice that were released from doxycycline at E14 on a PERK+/− background died by post natal day (PND) 27; whereas, double transgenic mice on a wild-type background displayed normal survival (FIG. 15).

The level of phosphorylted eIF-2α (p-eIF-2α) was determined severity of the phenotype of the mice was evaluated. The level of p-eIF-2α was significantly greater in the oligodendrocytes from PERK+/+ mice when compared to that measured in the PERK+/− mice (FIGS. 14E and F), whereas a modest increase in p-eIF-2α was seen in the CNS of the PERK+/− mice (FIGS. 15B and C). The loss of function mutation in pERK did not significantly affect the RNA level of BIP, CHOP and Caspase-12 (FIG. 15D).

These results suggest that the reduced capacity to elevate p-eIF-2α levels in response to IFN-γ contributes to the severe phenotype in mice misexpressing IFN-γ on a PERK+/− background.

Example 11

Figure 16:
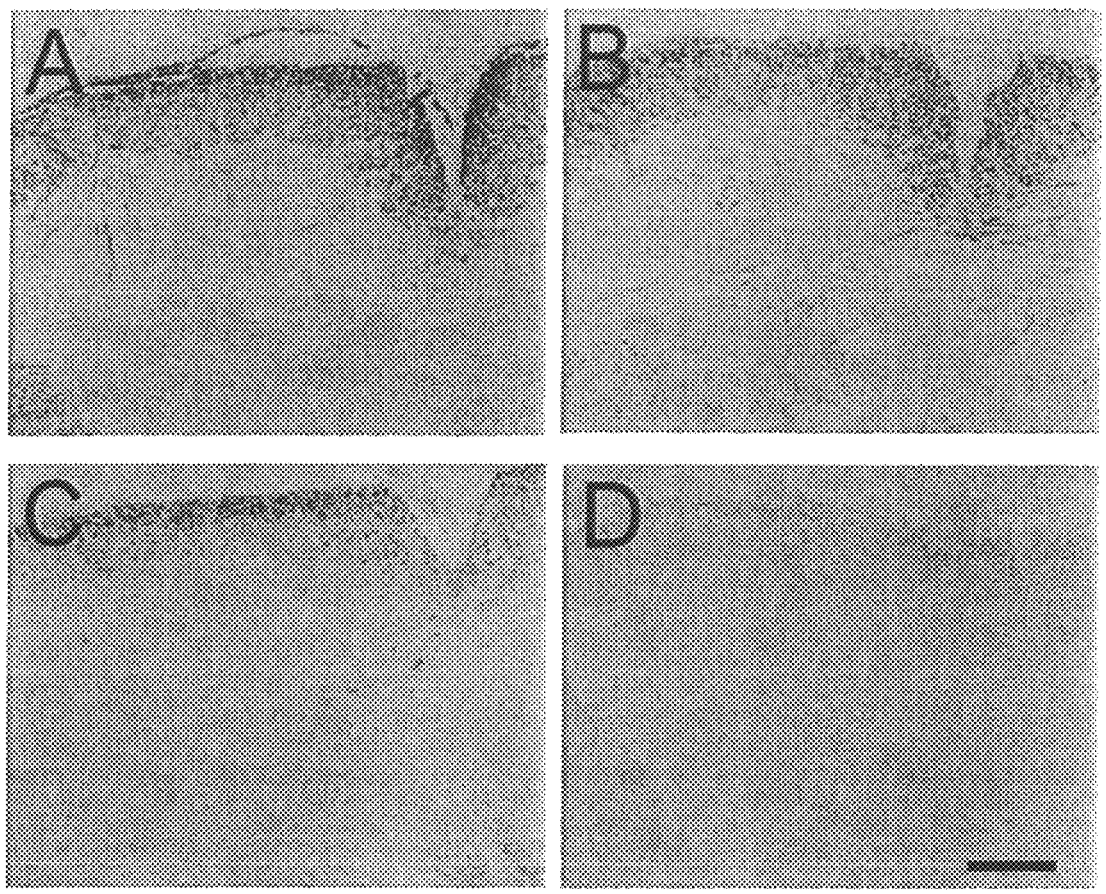
FIG. 16 shows that double transgenic mice with a PERK+/− background develop severe hypomyelination. (A) MBP immunostaining in the spinal cord of 14-day-old double transgenic mice that received doxycycline. (B) MBP immunostaining in the spinal cord of 14-day-old GFAP/tTA; TRE/IFN-γ; PERK+/− mice that received doxycycline. (C) MBP immunostaining in the spinal cord of 14-day-old double transgenic mice released from doxycycline at E 14. (D) MBP immunostaining in the spinal cord of 14-day-old GFAP/tTA; TRE/IFN-α; PERK+/− mice released from doxycycline at E 14. Panels A, B, C and D: n=3, scale bar=150 μM.
Figure 17:
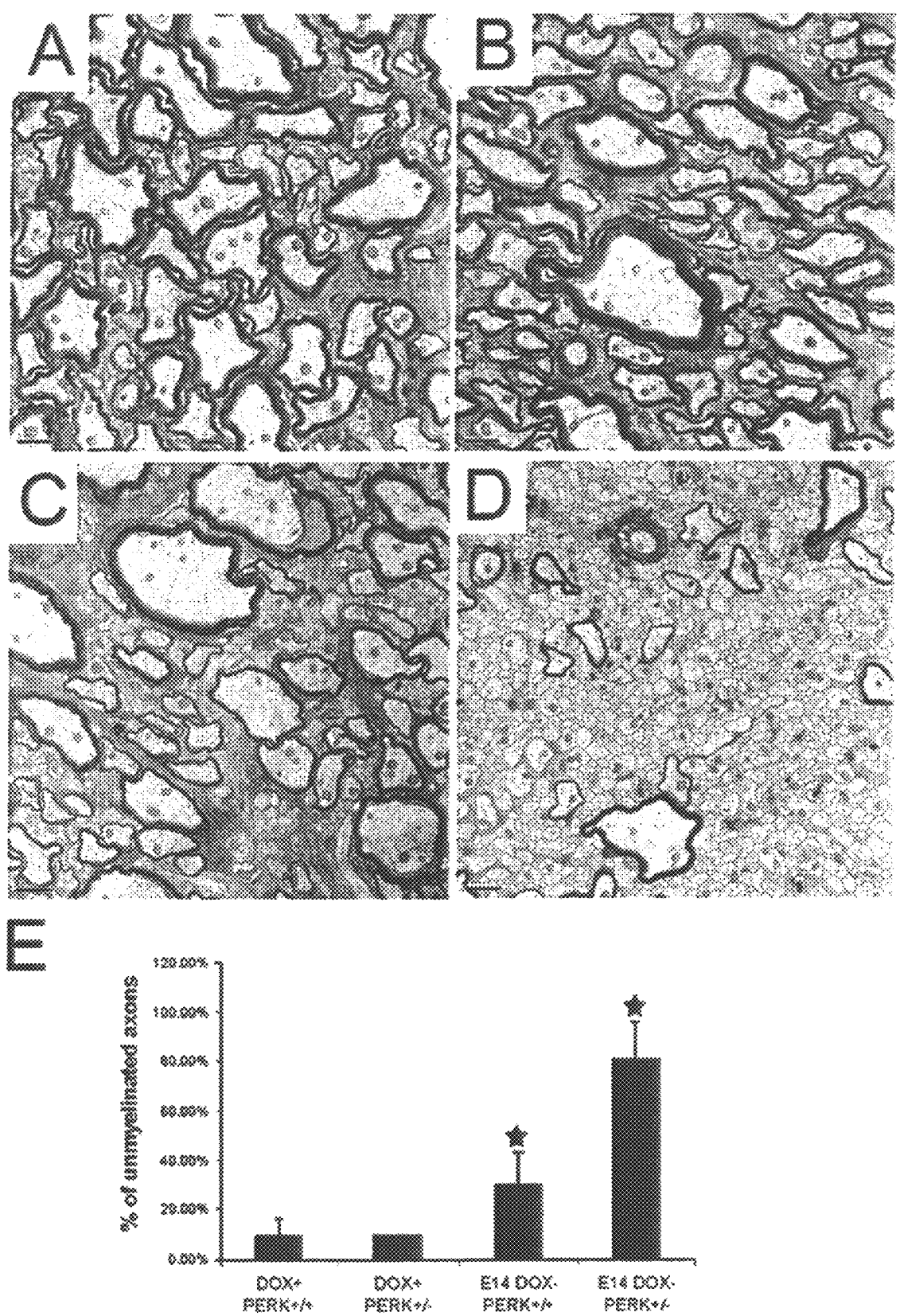
FIG. 17 shows that double transgenic mice with a PERK+/− background develop severe hypomyelination. (A) Ultrastructural examination showing normal myelination in the spinal cord of 14-day-old double transgenic mice that received doxycycline. (B) Ultrastructural examination showing normal myelination in spinal cord of 14-day-old GFAP/tTA; TRE/IFN-γ; PERK+/− mice that received doxycycline. (C) Ultrastructural examination showing minor hypomyelination in the spinal cord of 14-day-old double transgenic mice released from doxycycline at E 14. (D) Ultrastructural examination showing severe hypomyelination in the spinal cord of 14-day-old GFAP/tTA; TRE/IFN-γ; PERK+/− mice released from doxycycline at E 14. Panels A, B, C, and D: n=3, scale bar=1 μM. (E) The percentage of unmyelinated axons in the white matter of cervical spinal cord was calculated from three mice per time point, *p<0.01.

IFN-γ Mis-Expression Leads to Severe Hypomyelination in a PERK+/− Background The tremoring phenotype with tonic seizures displayed by the PERK+/− mice that express IFN-γ in the CNS (as described in Example 3) is suggestive of myelin perturbations. To evaluate the level of myelination in the PERK+/− mice, the state of myelination was evaluated by immunostaining for MBP was performed in the CNS of 14-day-old GFAP/tTA; TRE/IFN-γ; PERK+/− mice released from doxycycline at E 14, and compared to that of double transgenic mice on a wild-type background (FIG. 16). Immunostaining for myelin basic protein (MBP) was notably reduced in the CNS of 14-day-old GFAP/tTA; TRE/IFN-γ; PERK+/− mice released from doxycycline at E 14, compared with double transgenic mice on a wild-type background (FIG. 16). Moreover, ultrastructural examination revealed that the majority (81%±14.9%) of axons in the spinal cord of PERK+/− mice that express IFN-γ in the CNS were unmyelinated (FIG. 17). In contrast, double transgenic animals on a wild-type background released from doxycycline at E14 displayed considerably fewer unmyelinated axons (30%±12.9%), whereas animals maintained continuously on doxycycline to repress IFN-γ expression had even fewer unmyelinated axons (9.8%±6.1%).

These data establish a correlation between the severe tremoring phenotype induced by IFN-γ on the PERK+/− background and hypomyelination.

Example 12

Loss of Oligodendrocytes Following IFN-γ Mis-Expression in PERK+/− Mice

Figure 18:
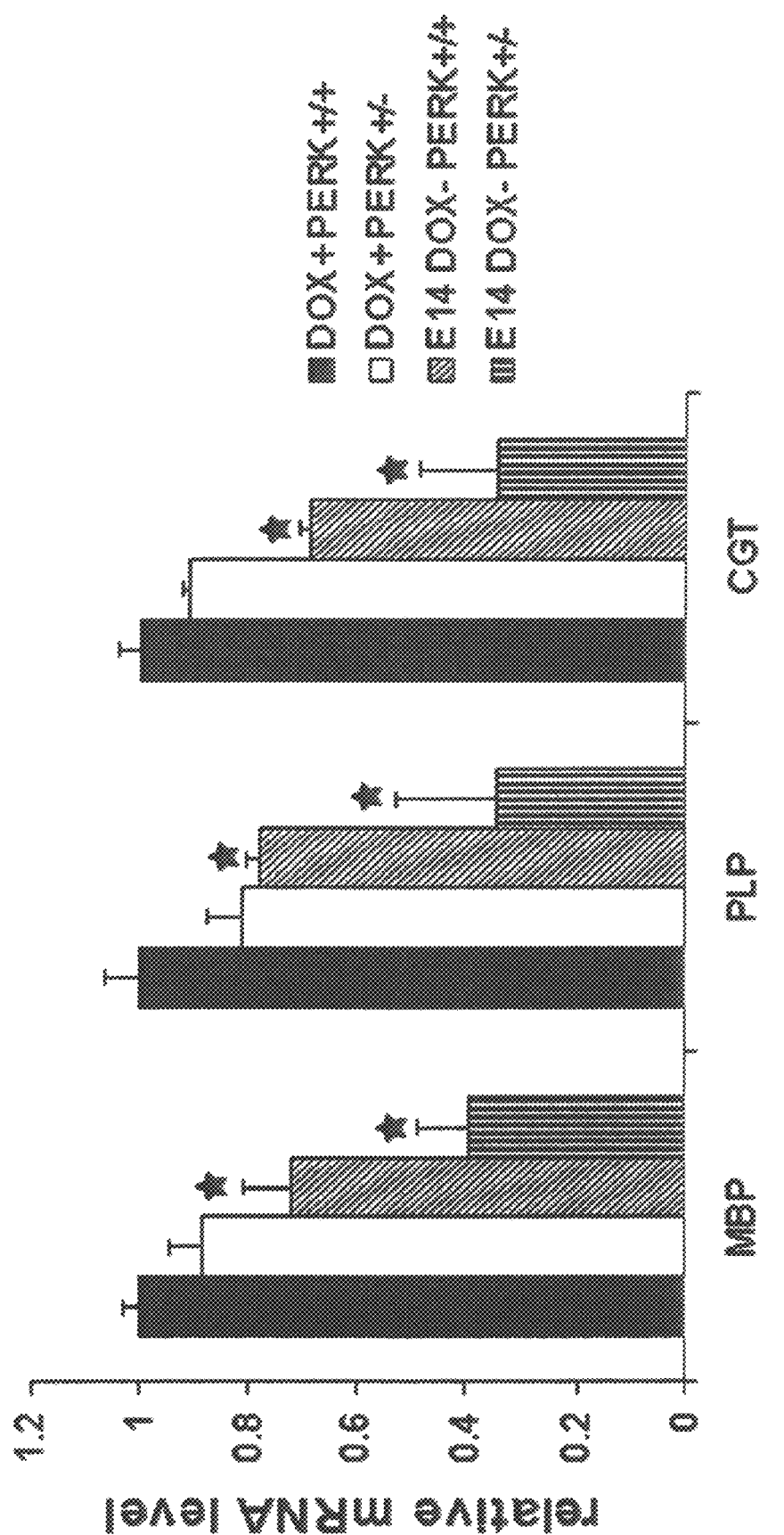
FIG. 18 shows that the levels of MBP, PLP and CGT mRNA were significantly decreased in the CNS of double transgenic mice with a PERK+/− background. Real-time PCR analyses for myelin gene expression in the brain of 14-day-old mice (n=3), *p<0.05.
Figure 19:
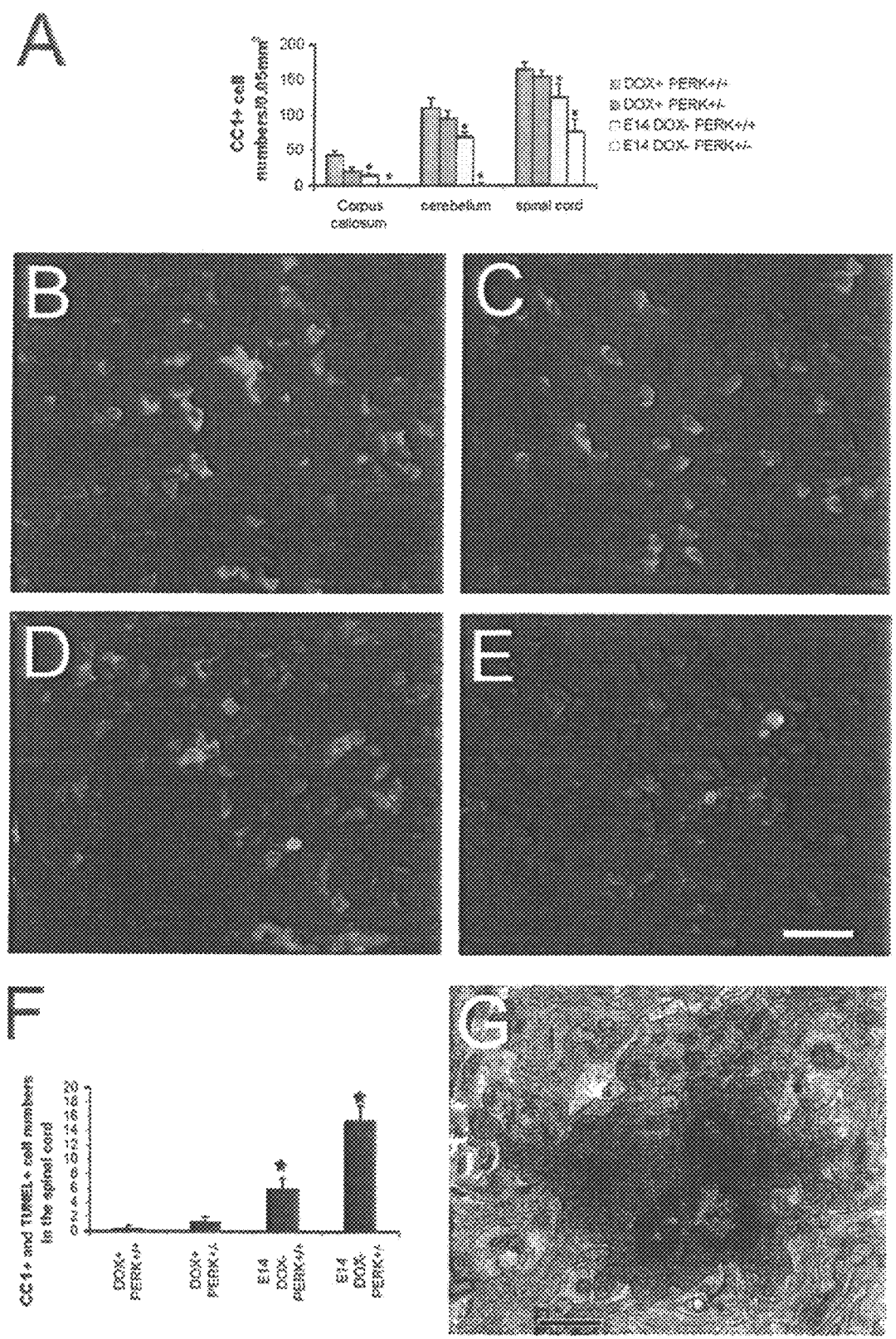
FIG. 19 shows that double transgenic mice with a PERK+/− background lose the majority of the oligodendrocytes in the CNS. (A) Quantitation of CC1 positive cells in the CNS of 14-day-old mice (n=3), *p<0.05. (B) TUNEL and CC1 double labeling in spinal cord of 14-day-old double transgenic mice that received doxycycline. (C) TUNEL and CC1 double labeling in the spinal cord of 14-day-old GFAP/tTA; TRE/IFN-γ; PERK+/− mice that received doxycycline. (D) TUNEL and CC1 double labeling in the spinal cord of 14-day-old double transgenic mice released from doxycycline at E 14. (E) TUNEL and CC1 double labeling in the spinal cord of 14-day-old GFAP/tTA; TRE/IFN-γ; PERK+/− mice released from doxycycline at E 14. Panels B, C, D and E: n=3; scale bar=60 μM; red fluorescence showing CC1 immunoreactivity, green fluorescence showing TUNEL stain and blue fluorescence showing DAPI counter stain. (F) Quantitation of TUNEL of CC1 double positive cells in the spinal cord of 14-day-old mice (n=3), *p<0.01. (G) Ultrastructural examination showing apoptotic oligodendrocytes contained highly condensed chromatin mass, intact membrane, shrunken cytoplasm and apoptosis body, scale bar=2 μM.

To gain insight into the cellular mechanisms that account for the hypomyelination displayed by the PERK+/− mice that express IFN-γ in the CNS, the status of oligodendrocyte function in these animals was examined We determined the steady state levels of mRNAs encoding the myelin markers MBP, PLP and ceramide galactosyltransferase (CGT). Real-time PCR analysis showed that the MBP, PLP and CGT mRNA levels in the brains of 14-day-old double transgenic mice on a wild-type background released from doxycycline at E 14 were slightly lower than normal. These mRNA levels were even lower in the CNS of GFAP/tTA; TRE/IFN-γ; PERK+/− mice released from doxycycline at E 14 (FIG. 18). To determine if the decreased steady-state levels of myelin protein encoding mRNAs was due to reduced numbers of myelinating cells we determined oligodendroglial numbers in these mice. Compared with control mice, there were slightly fewer oligodendrocytes identified by CC1 immunostaining in the CNS of 14-day-old GFAP/tTA; TRE/IFN-γ transgenic mice on a wild-type background released from doxycycline at E 14 (FIG. 19A). In contrast, very few oligodendrocytes could be detected in the corpus callosum and cerebellum of IFN-γ expressing transgenic mice on a PERK+/− background, and oligodendrocyte numbers in the spinal cord of these mice were decreased by more than 50% (FIG. 19A).

In addition, the number of oligodendrocytes that were TUNEL positive in the cervical spinal cord of these mice was 2.5 times higher than the number of such cells in double transgenic mice on a wild-type background, following release from doxycycline at E 14 (FIGS. 19B, 19C, 19D, 19E and 19F). Moreover, ultrastructural examination showed that apoptotic oligodendrocytes contained highly condensed chromatin mass, intact membrane, shrunken cytoplasm and apoptotic body (FIG. 19G). These data reinforce the hypothesis that IFN-γ damages oligodendrocytes by means of the ER stress pathway and indicate that PERK plays a critical role in protecting oligodendrocytes from the detrimental consequences of IFN-γ-induced ER stress.

Example 13

Figure 20:
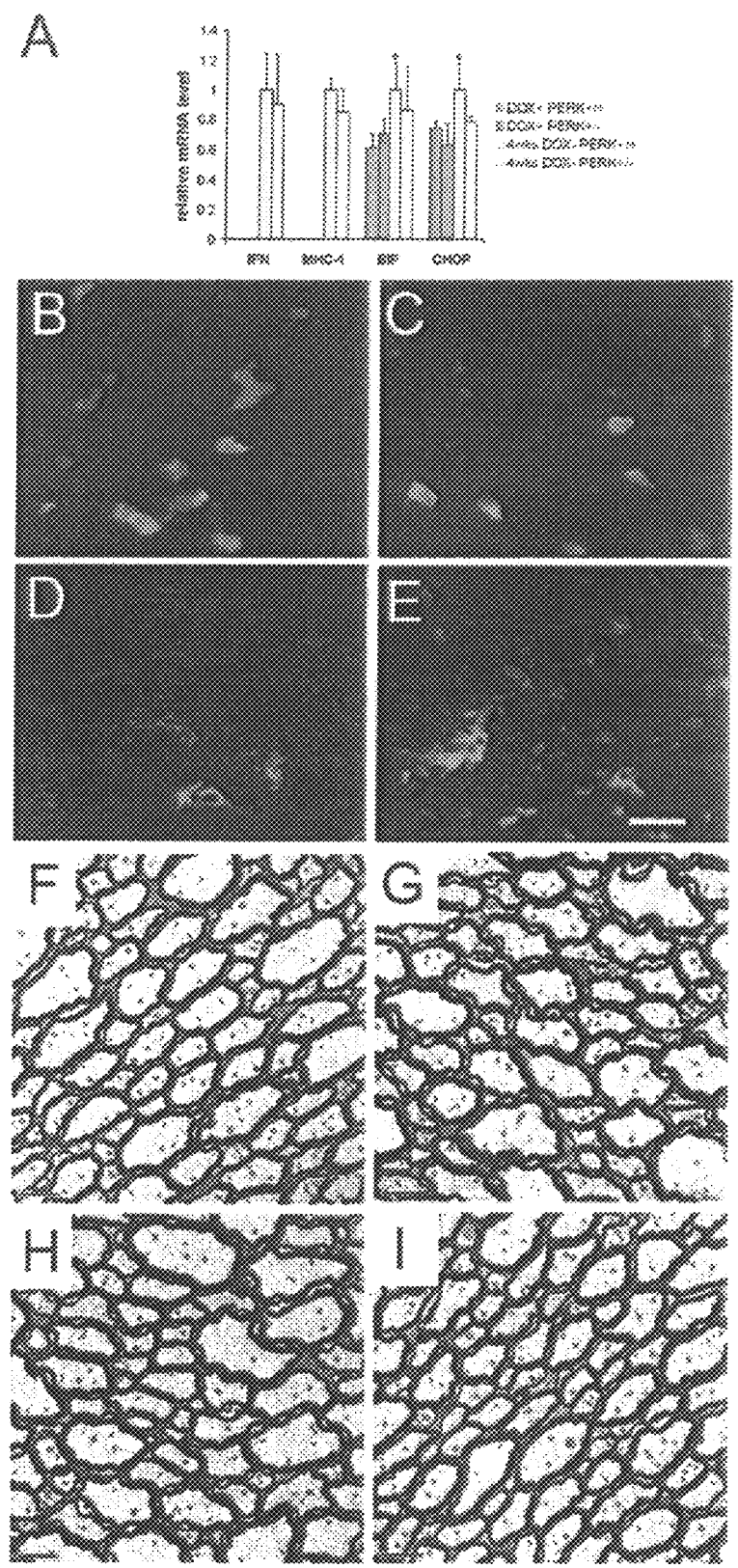
FIG. 20 shows that oligodendrocytes in adult mice are less sensitive to IFN-γ than actively myelinating oligodendrocytes from younger mice. (A) Real-time PCR analyses of mRNA levels in the brain of 10-week-old mice (n=3), *p<0.05. (B) BIP and CC1 double immunostaining in the cerebellum of 10-week-old double transgenic mice that received doxycycline. (C) BIP and CC1 double immunostaining in the cerebellum of 10-week-old GFAP/tTA; TRE/IFN-γ; PERK+/− mice that received doxycycline. (D) BIP and CC1 double immunostaining in the cerebellum of 10-week-old double transgenic mice released from doxycycline at 4 weeks of age. (E) BIP and CC1 double immunostaining in the cerebellum of 10-week-old GFAP/tTA; TRE/IFN-γ; PERK+/− mice released from doxycycline at 4 weeks of age. Panels B, C, D and E: n=3, scale bar=60 μM; red fluorescence showing CC1 immunoreactivity, green fluorescence showing BIP stain and blue fluorescence showing DAPI countstain. (F) Ultrastructural examination showing normal myelination in the cerebellum of 10-week-old double transgenic mice that received doxycycline. (G) Ultrastructural examination showing normal myelination in the cerebellum of 10-week-old GFAP/tTA; TRE/IFN-γ; PERK+/− mice that received doxycycline. (H) Ultrastructural examination showing normal myelination in the cerebellum of 10-week-old double transgenic mice released from doxycycline at 4 weeks of age. (I) Ultrastructural examination showing normal myelination in the spinal cord of 10-week-old GFAP/tTA; TRE/IFN-γ; PERK+/− mice released from doxycycline at 4 weeks of age. Panels F, G, H and I: n=3, scale bar=2 μM.

Oligodendrocytes in Adult Animals are Less Sensitive to IFN-γ than Actively Myelinating Oligodendrocytes from Younger Animals Compared with the actively myelinating oligodendrocytes of young growing animals, oligodendrocytes in adult mice produce lower levels of membrane proteins and lipids, just enough to maintain homeostasis in the myelin structure (Morell, et al. (1999) *Basic Neurochemistry: Molecular, Cellular, and Medical Aspects* (Philadelphia, Pa.: Lippincott-Raven Publishers): 69-93). The ER of oligodendrocytes in adult animals may thus have more spare capacity to process increased protein load and as such may be less sensitive to disruptions of the protein secretory pathway. To examine this possibility, double transgenic mice were allowed to develop to maturity, at which time IFN-γ expression in the CNS was initiated. Real-time PCR analysis showed that double transgenic animals released from doxycycline at 4 weeks of age started expressing IFN-γ at approximately 6 weeks of age, and the levels of IFN-γ mRNA and protein in the CNS were comparable with those in developing mice released from doxycycline at E 14 (data not shown). IFN-γ did not affect oligodendrocyte survival in adult mice, even in mice on a PERK+/− background (FIGS. 20B, 20C, 20D and 20E). Moreover, ultrastructural examination revealed normal myelin in the CNS of 10-week-old double transgenic mice with a wild-type or a PERK+/− background that were released from doxycycline at 4 weeks of age (FIGS. 20F, 20G, 20H and 20I). A modest induction of BIP and CHOP by IFN-γ was observed in the cerebellum of 10-week-old double transgenic mice released from doxycycline at 4 weeks of age (FIG. 20A). Nevertheless, colocalization analysis showed that mature oligodendrocytes did not significantly increase BIP expression (FIGS. 20B, 20C, 20D and 20E).

Thus, the data indicate that oligodendrocytes from adult animals are less sensitive to the presence of IFN-γ than are actively myelinating oligodendrocytes of growing juvenile mice.

Example 14

Administration of INF-γ at the Onset of EAE Attenuates the Severity of the Disease Double transgenic mice that allow for temporally regulated delivery of INF-γ to the CNS (Lin et al., J Neurosci 24:10074-10083 (2004)) were used to assess the role of INF-γ in the pathogenesis of EAE. GFAP/iTA; TRE/IFN-γ double transgenic mice, as described in the Examples above, were used to determine the effect of INF-γ on the demyelination caused by EAE. All mice were fed doxycycline from the day of conception to repress the expression of INF-γ, and the experimental group were later immunized with MOG 35-55 peptide to induce the development to EAE. For induction of EAE, mice received subcutaneous injections at flanks and tail base of 200 μg MOG 35-55 peptide emulsified in complete Freund's adjuvant (Difco) supplemented with 600 μg of *Mycobacterium tuberculosis* (strain H37Ra; Difco). 2 intraperitoneal injections of 400 ng pertussis toxin (List Biological Laboratories) were given 24 and 72 h later. Clinical score (0=healthy, 1=flaccid tail, 2=ataxia and/or paresis of hindlimbs, 3=paralysis of hindlimbs and/or paresis of forelimbs, 4=tetraparalysis, 5=moribund or death) were recorded daily. The control animals were continuously fed doxycycline (DOX+ double mice), while the experimental animals (DOX− double mice) were deprived of the antibiotic to allow for the expression of INF-γ. The effect of INF-γ was monitored as follows.

Figure 21A:
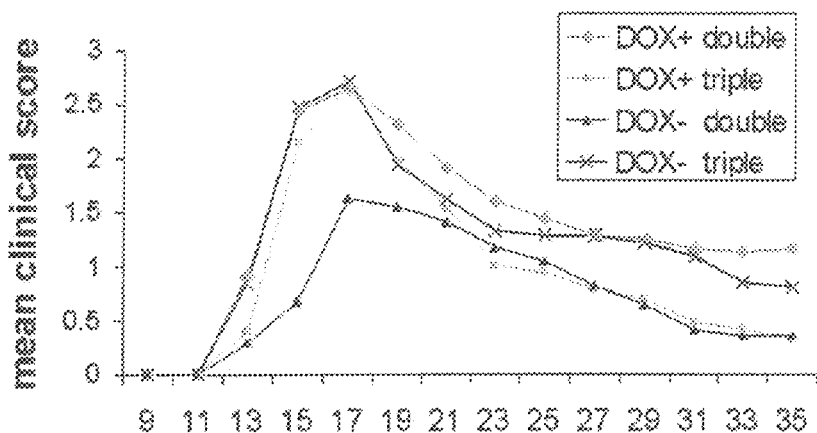
FIG. 21 shows a comparison of the onset and progression of EAE in DOX+ and DOX− mice that are wild type (DOX triple; PERK+/+) or are heterozygous for a mutation (DOX triple; PERK+/−) in the PERK enzyme. (A) Changes in the mean clinical score for mice with and without EAE. (B and C) Real time PCR analysis for the expression of INF-γ and T-INF in mice at post-immunization days (PID) 14, 17 and 22. Asterisk p<0.01-0.05, student t test; n=2. Error bars represent standard deviation.

The onset of disease was evident at day 14 in both DOX− and DOX+ double animals, and no significant differences in clinical score were seen at that time (PID14; post-immunization day 14). However, DOX− double mice developed significantly milder disease than the DOX+ double mice, and only 2 of 25 animals in the DOX− group, showed hind limb paralysis, while a significantly greater portion (20/25) of the DOX+ double mice had limb paralysis (FIG. 21(*a*) and Table 1)

TABLE 1

Delivery of INF-γ to the CNS at the onset of EAE attenuates the severity of the disease

| | Day of onset of disease (PID: postimmunization day) | Mean of maximum clinical score (mean ± S.D.) | Incidence of hind limb paralysis | Incidence of death |
|---|---|---|---|---|
| DOX+ double mice | 13.6 ± 1.2 | 2.66 ± 0.80 | 20/25 | 0/25 |
| DOX+ triple mice | 14.0 ± 0.9 | 2.67 ± 0.94 | 19/25 | 2/25 |
| DOX− double mice | 14.7 ± 1.4 | 1.63 ± 0.51* | 2/25 | 0/25 |
| DOX− triple mice | 13.6 ± 0.8 | 2.71 ± 1.11 | 18/25 | 3/25 |

*p, 0.001, n = 25. Clinical severity scores were recorded daily according to a 0-5 point scale, where 0 = healthy, 1 = flaccid tail, 2 = ataxia and/or paresis of hind limbs, 3 = paralysis of hind limbs and/or paresis of forelimbs, 4 = tetraparalysis, and 5 = moribund or dead.

Figure 21B:
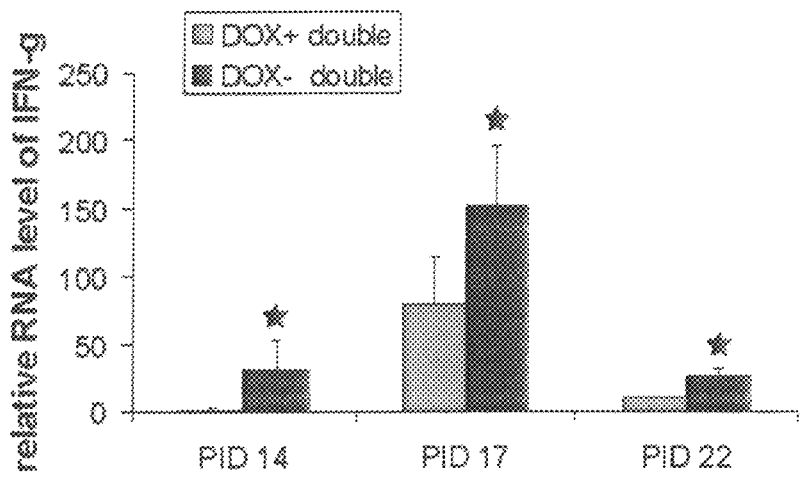

Real-time PCR analysis was performed to assess the level of expression of INF-γ in the spinal cord of DOX− and DOX+ animals. Anesthetized mice were perfused with PBS. RNA was isolated from the spinal cord using Trizol reagent (Invitrogen) and treated with DNAseI (Invitrogen,) to eliminate genomic DNA. Reverse transcription was performed using Superscript First Strand Synthesis System for RT-PCR kit (Invitrogen). Taqman real-time PCR was performed with iQ supermix (Bio-Rad) on a Bio-Rad iQ real-time PCR detection system as previously described[12]. FIG. 21(b) shows that the levels of IFN-γ in the spinal cord of the DOX− animals became detectable at EAE onset (PID 14), reached peak at the peak of disease (PID 17), then decreased at the recovery stage of disease (PID 22).

Figure 21C:
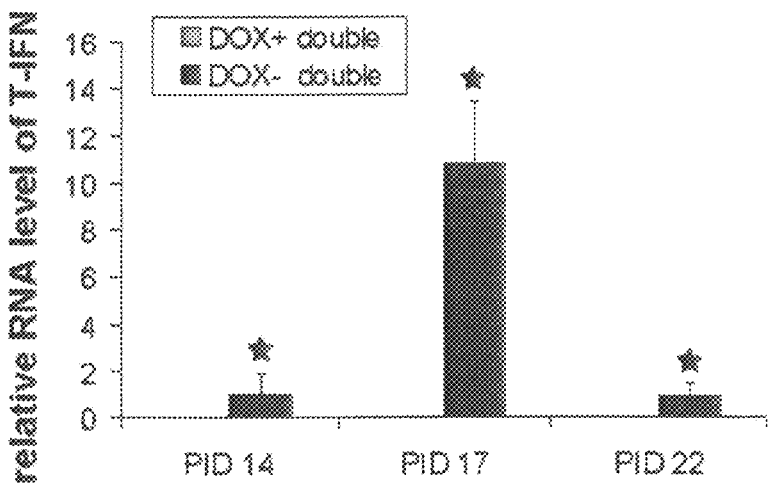

The level of IFN-γ mRNA in the spinal cord of DOX− animals was significantly higher than that of the DOX+ mice at all times PID 14, PID 17 and PID 22 (FIG. 21b). In addition, for transgenic IFN-γ could be detected in the spinal cord of DOX− double mice as early as PID 14 (FIG. 21c). Thus, these data show that delivery of IFN-γ to the CNS at the time of onset of EAE significantly attenuates the development of the severity of the disease.

Figure 22:
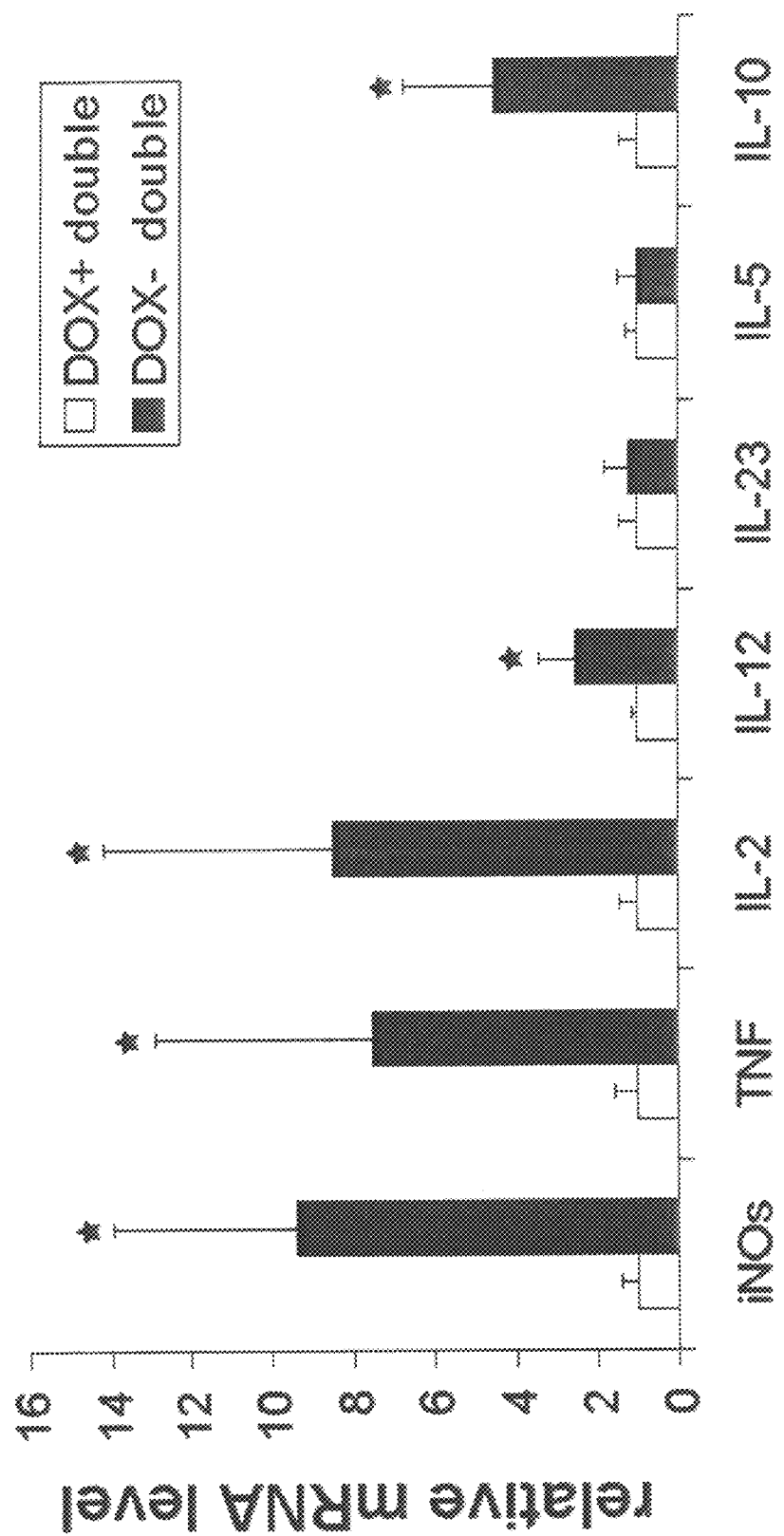
FIG. 22 shows the results of real time PCR analysis for the expression of iNOs, TNF-α, IL-2, IL-12, IL-10, IL-23 and IL-5 at PID 14 in the spinal cord of DOX+ and DOX− mice with EAE. *p<0.05, student t test; n=4.

Real time PCR analysis of the expression of various cytokines in the spinal cord of DOX− and DOX+ animals at PID 14 showed that INF-γ increased the expression of iNOs, TNF-a, IL-2, IL-12 and IL-10, but did not affect the expression of IL-2 and IL-5 (FIG. 22).

Histopathological evaluation of the effect of INF-γ on demylination caused by EAE was performed on the spinal cord of the DOX+ and DOX− animals at the peak of the disease (PID17). The spinal cord of the DOX− animals showed destruction of myelin sheaths, axon damage, oligodendrocyte loss (FIGS. 23A, 23B and 23C) and perivascular inflammation (FIGS. 24A and 24B), which are characteristic of the histopathology that is typical of EAE. In contrast, myelin, axons and oligodendrocytes from the lumbar spinal cord of DOX− animals remained almost intact (FIGS. 23A, 23B and 23C), and CD3 positive T cell infiltration was lower than that seen i the DOX+ animals (FIG. 24A). Moreover, the mRNA level of myelin basic protein (MBP) in the spinal cord of DOX− double mice, as assessed by real-time PCR, revealed that MBP mRNA was not significantly decreased by EAE when compared to MBP mRNA levels in age-matched naïve mice. However, the level of MBP mRNA was decreased by 30% in the DOX+ double mice, (FIG. 23D).

Thus, these data show that delivery of IFN-γ to the CNS protects against EAE-induced demyelination.

Example 15

Administration of INF-γ at the Onset of EAE Protects Oligodendrocytes from Demyelination Through a Cytoprotective Mechanism and Independently of its Anti-Inflammatory Properties During EAE pathogenesis, T cells are primed in peripheral immune system and enter the CNS well before the onset of clinical disease Hickey et al., (1991) J Neurosci Res 28:254-260. To determine whether the effect of INF-γ in protecting the CNS from the demyelinating effect of EAE results from the anti-inflammatory activity of INF-γ, the level of T-cell and monocyte infiltration was assessed and the expression of known inflammatory cytokines evaluated.

Figure 24:
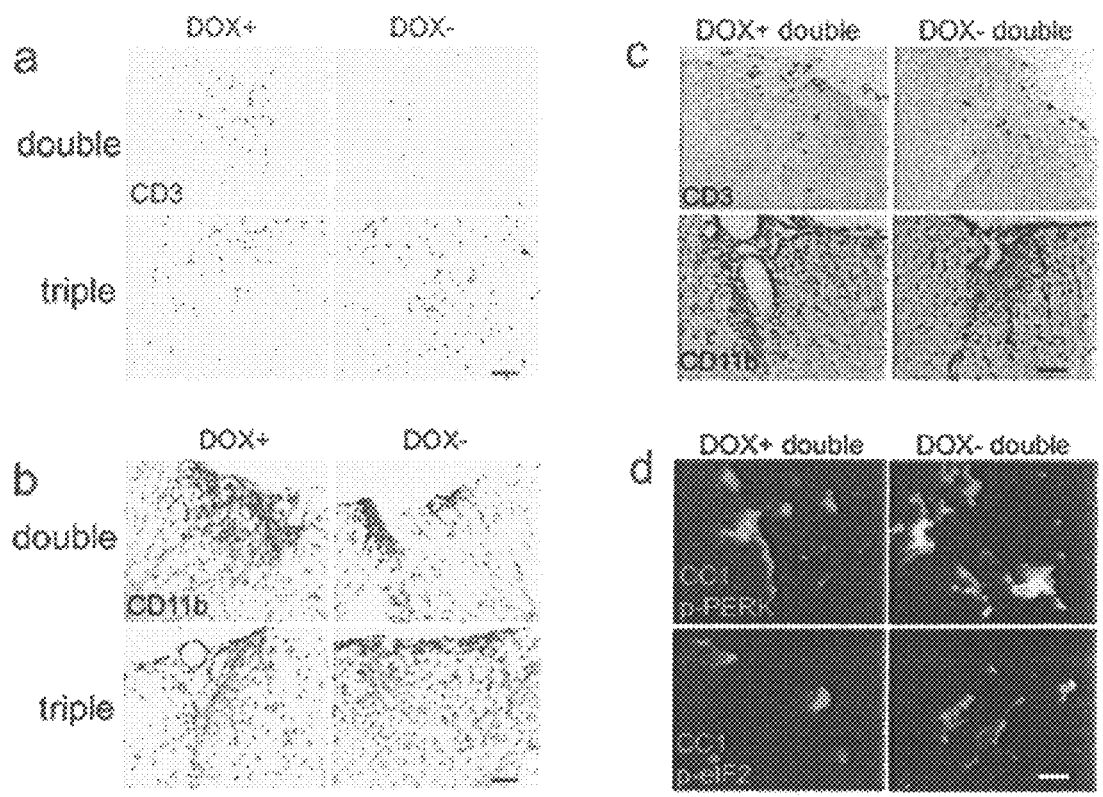
FIG. 24 shows that IFN-γ protected against EAE-induced demyelination through its cytoprotecive effects on oligodendrocyte. A. CD3 immunostaining showed CNS delivery of IFN-γ reduced T cell infiltration in the lumbar spinal cord of mice on a PERK+/+ background at PID17, but did not significantly affect T cell infiltration in mice on a PERK+/− background. N=3 scale bar=50 μm. B. CD11b immunostaining revealed that CNS delivery of IFN-γ did not significantly change the infiltration pattern of CD11b positive monocytes in the lumbar spinal cord of mice on a PERK+/+ and PERK+/− background at PID 17. N=3, scale bar=50 μm. C. and D. CD 3 immunostaining showed that CNS delivery of IFN-γ did not affect T cell infiltration in lumbar spinal cord at PID 14.
Figure 25:
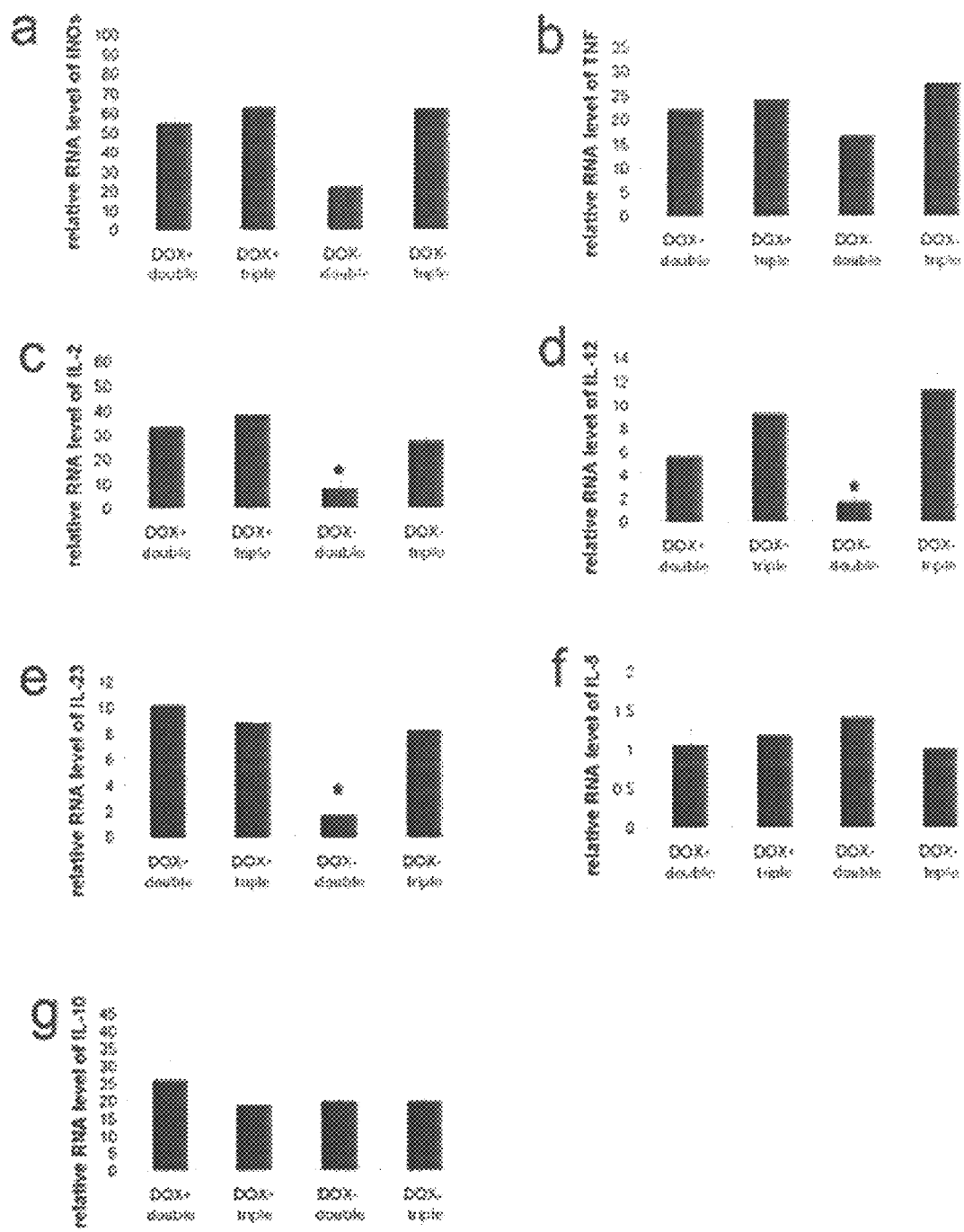
FIG. 25 depicts real-time PCR analysis for the expression pattern of cytokines in the spinal cord at the peak of disease. (A) CNS delivery of IFN-γ did not significantly affect the expression of iNOs. (B) CNS delivery of IFN-γ did not significantly affect the expression of TNF-γ. (C) CNS delivery of IFN-γ decreased the expression of IL-2 in spinal cord of mice on a PERK+/+ background, but did not change IL-12 expression in mice on a PERK+/− background. (D) CNS delivery of IFN-γ decreased the expression of IL-12 in spinal cord of mice on a PERK+/+ background, but did not change IL-12 expression in mice on a PERK+/− background. (E) CNS delivery of IFN-γ decreased the expression of IL-23 in spinal cord of mice on a PERK+/+ background, but did not change IL-12 expression in mice on a PERK+/− background. (F) CNS delivery of IFN-γ did not significantly affect the expression of IL-5. CNS delivery of IFN-γ did not significantly affect the expression of IL-10. All panels: n=3, error bars represent standard derivation; asterisk p<0.05. CNS delivery of IFN-γ did not significantly affect the expression of IL-10. All panels: n=3, error bars represent standard derivation; asterisk p<0.05.

The results shown in FIGS. 24C and 24D show that IFN-γ did not significantly affect CD3 positive T cell infiltration, but increased CD11b positive monocyte infiltration in the spinal cord at EAE onset (FIGS. 24E and 24F). Importantly, real-time PCR analyses showed that delivery of IFN-γ to the CNS strongly enhanced the expression of inducible nitric oxide synthase (iNOs), tumor necrosis factor-γ (TNF-γ), interleukin-2 (IL-2), IL-12 and IL-10 in the spinal cord at EAE onset (FIG. 22), but did not significantly affect the expression of iNOs or TNF-γ at the peak of disease (FIG. 25). In addition, CNS delivery of IFN-γ did not change CD11b positive monocyte infiltration at the peak of disease (FIG. 24B).

These data suggest that it is unlikely that IFN-γ protects EAE-induced demyelination due to its anti-inflammatory properties; a hypothesis that has been proposed by some investigators (Muhl et al., Int. Immunopharmacol 3:1247-1255 (2005)).

Oligodendrocyte death has been shown to modulate inflammatory infiltration in EAE lesions (Hisahara et al., EMBO J 19:341-348 (2000); Hisahara et al., (2001) J Exp Med 193:111-122). It is possible that while INF-γ promotes an inflammatory response at the onset of EAE, the inhibitory effect of INF-γ on the death of oligodendrocytes at a later stage of disease may explain the decrease in T cell infiltration. Our previous findings have shown that transgenic mice that express INF-γ under the control of the MBP gene are resistant to oligodendrocyte apoptosis and demyelination induced by cuprizone (Gao et al., (2000) Mol Cell Neurosci 16:338-349). It is thought that the oligodendrocytes that are injured by cuprizone go though apoptosis (Matsushima and Morell (2001) Brain Pathol 11:107-116), which is closely followed by the recruitment of microglia and phagocytosis of myelin. In the cuprizone animal model, it is known that the demylination oligodendrocyte apoptosis do not involve T cells or a breakdown of the blood brain barrier.

Therefore, these data suggest that IFN-γ protects oligodendrocytes from demyelination through a cytoprotective effect.

Example 16

Administration of INF-γ at the Onset of EAE Protects Oligodendrocytes from Demyelination by Activating the PERK Pathway Demyelination and oligodendrocyte loss are the hallmarks of multiple sclerosis (MS) and its animal model, experimental autoimmune encephalomyelitis (EAE). It has long been known that low levels of stress that activate downstream signaling pathways without causing severe cell injury can protect against subsequent exposure to more-severe stressful events. Pancreatic endoplasmic reticulum kinase (PERK) encodes an ER stress-inducible kinase that phosphorylates eukaryotic translation initiation factor 2α (eIF2α) and enhances the stress-induced expression of numerous cytoprotective genes (Harding et al., (1999) Nature 397:271-274; Lu et al., (2004) EMBO J 23:169-179; Harding et al., (2003) Mol Cell 11:619-633).

To determine whether the PERK pathway mediates the protective effects of IFN-γ from demyelination induced by EAE, the level of phosphorylated-PERK (p-PERK) and phosphorylated-eIF2α (p-eIF2α) was monitored in oligodendrocytes during the course of EAE.

Colocalization analysis with the CC1 antibody revealed that a few oligodendrocytes were p-PERK positive and p-eIF2α positive in the spinal cord of control mice at EAE onset, consistent with a previous report (Chakrabarty et al., 2004). In contrast, CNS delivery of IFN-γ markedly activated the PERK-eIF2α pathway in oligodendrocytes (FIG. 24).

These data support a link between the activation of the PERK pathway in oligodendrocytes and a protective role of IFN-γ in EAE-induced demyelination.

Figure 23:
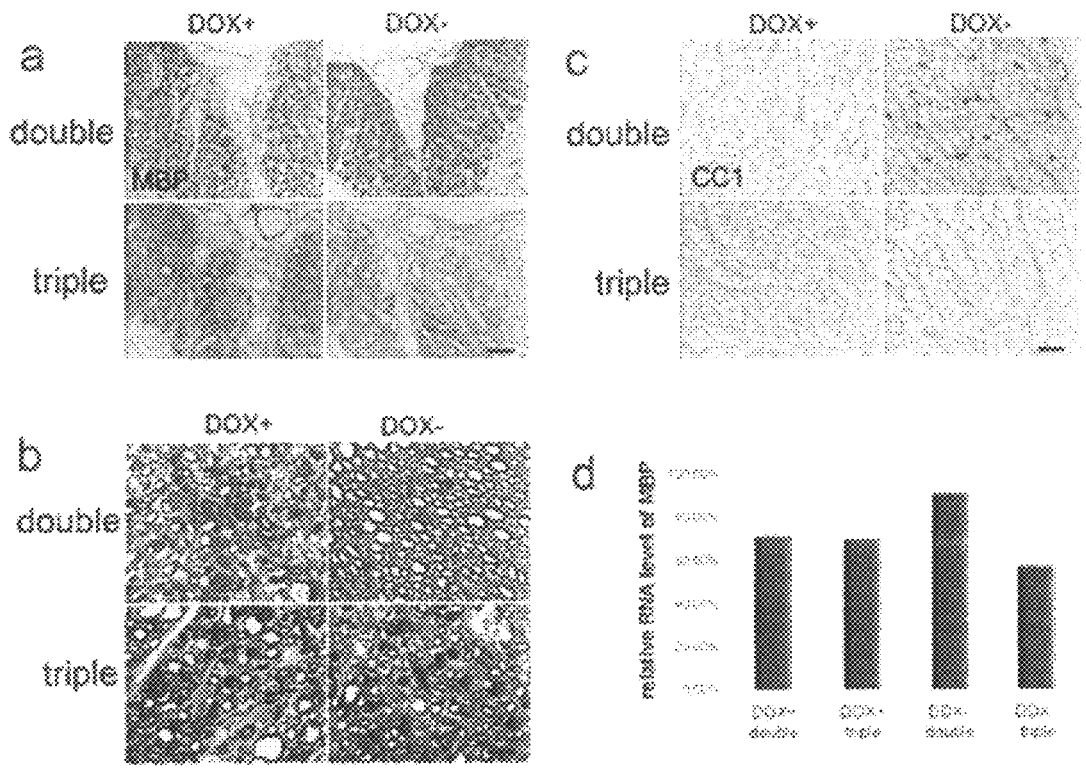
FIG. 23 shows that CNS delivery of IFN-γ at EAE onset protects against EAE-induced demyelination which is dependent on the PERK pathway. (A) MBP immunostaining of lumbar spinal cord tissue showed that CNS delivery of IFN-γ protected against EAE-induced demyelination in mice with a PERK+/+ background at day 17 postimmunization (PID 17). In contrast, more-severe demyelination was detected in the lumbar spinal cord of DOX− triple mice at PID 17, compared with control mice. N=3, scale bar=50 μm. (B) Toluidine blue staining revealed that the myelin and axons in the spinal cord of DOX− double mice remained almost intact at PID 17. In contrast, CNS delivery of IFN-γ did not prevent demyelination and axon damage in the lumbar spinal cord of mice with a PERK+/− background by PID 17. N=3, scale bar=10 μm. (C) CC1 immunostaining showed that oligodendrocytes in the lumbar spinal cord of DOX− double mice remained almost intact at PID 17. In contrast, similar to control mice, DOX− triple mice lost the majority of oligodendrocytes in the lumbar spinal cord at PID 17. N=3, scale bar=25 μm. (D) Real-time PCR analysis of the relative MBP mRNA level in the spinal cord at PID 17. A value of 100% represents the MBP mRNA level in the spinal cord of age-matched naive mice; n=3. Error bars indicate standard deviations.

A genetics-based approach was used to examine the involvement of the PERK pathway in the protective effects of IFN-γ on EAE. Mice that are heterozygous for a loss of function mutation in PERK are phenotypically healthy but display evidence of haploid insufficiency (Harding et al., 2000; Lin et al., 2005). TRE/IFN-γ mice were crossed with PERK+/− mice, and their progeny was crossed with GFAP/tTA mice to obtain triple transgenic mice that were heterozygous for the PERK mutation. Six-week-old GFAP/tTA; TRE/IFN-γ triple-transgenic mice with a PERK+/− background that had received doxycycline since conception were immunized with the MOG35-55 peptide and were either simultaneously withdrawn from doxycycline (DOX− triple mice) or continued to receive doxycycline (DOX+ triple mice). The control DOX+ triple mice showed an EAE disease course similar to that of control DOX+ double mice Strikingly, CNS delivery of IFN-γ did not ameliorate EAE in mice heterozygous for the PERK mutation. Morbidity rates, EAE severity, and mortality rates for DOX− triple mice were comparable with those for control DOX+ triple mice (Table 1). Neuropathologic analyses revealed that CNS delivery of IFN-γ at EAE onset did not prevent demyelination, axon damage, or oligodendrocyte loss in the lumbar spinal cord of mice with a PERK+/− background at the peak of disease. In fact, MBP immunostaining, toluidine blue staining, and real-time PCR analysis for MBP consistently showed comparable demyelination in the spinal cord of DOX− triple mice and control DOX+ triple mice at the peak of disease severity (FIG. 23). In addition, we found that the loss of function mutation in PERK did not significantly affect inflammatory infiltration and the expression profile of cytokines in the course of EAE. Therefore, these data show that the activation of the PERK pathway by IFN-γ in oligodendrocytes is essential for protecting neurons against demyelination caused by EAE. This suggests that IFN-γ activates an "integrated stress response" which is dependent on PERK pathway that provides protection against subsequent exposure to harmful agents to the neuronal system.

Example 17

The Role of GADD34 in Demyelination: Effects of the Loss of Function of GADD34 In Vivo The role of GADD-34 in demyelination was studied in mice lacking GADD-34 and in which EAE was induced.

Activation of eIF2α has been observed in oligodendrocytes during EAE (Chakrabarty et al, 2004; Chakrabarty et al., 2005). As described in the examples above, CNS delivery of IFN-γ at EAE onset has been shown to protect against EAE-induced demyelination and to attenuate the severity of the disease by activating the PERK-dependent integrated stress response pathway. GADD34 is a stress-inducible gene that encodes a regulatory subunit that engages protein phosphatase-1 (PP1) and targets dephosphorylation of the eukaryotic translation elongation factor eIF2α (Connor et al., 2001; Novoa, 2001; Novoa et al., 2003). GADD34-null mice are healthy, but a loss of GADD34 increases the level of phosphorylated eIF2α (p-eIF2α) in stressed cells. Furthermore, it has been shown that GADD34-null animals are markedly protected from cell death caused by ER stress (Jousse et al., 2003; Marciniak et al., 2005). Therefore, role of eIF2α in the pathogenesis of EAE was tested using GADD34-null mice.

GADD34-null mice were generated. The mice have been backcrossed 6 times with C57BL/6 mice. EAE is induced as follows. Mice were given a subcutaneous injection in the flank and tail base of 200 μg MOG 35-55 peptide which was emulsified in complete Freund's adjuvant and supplemented with 600 μg of Mycobacterium tuberculosis. Two injections each of 400-ng of pertussis toxin were given intraperitoneally at 24 and 72 h following the immunization with the MOG 35-55 peptide. Clinical severity scores were recorded daily according to a 0-5 point scale, where 0=healthy, 1=flaccid tail, 2=ataxia and/or paresis of hind limbs, 3=paralysis of hind limbs and/or paresis of forelimbs, 4=tetraparalysis, and 5=moribund or dead.

Figure 26:
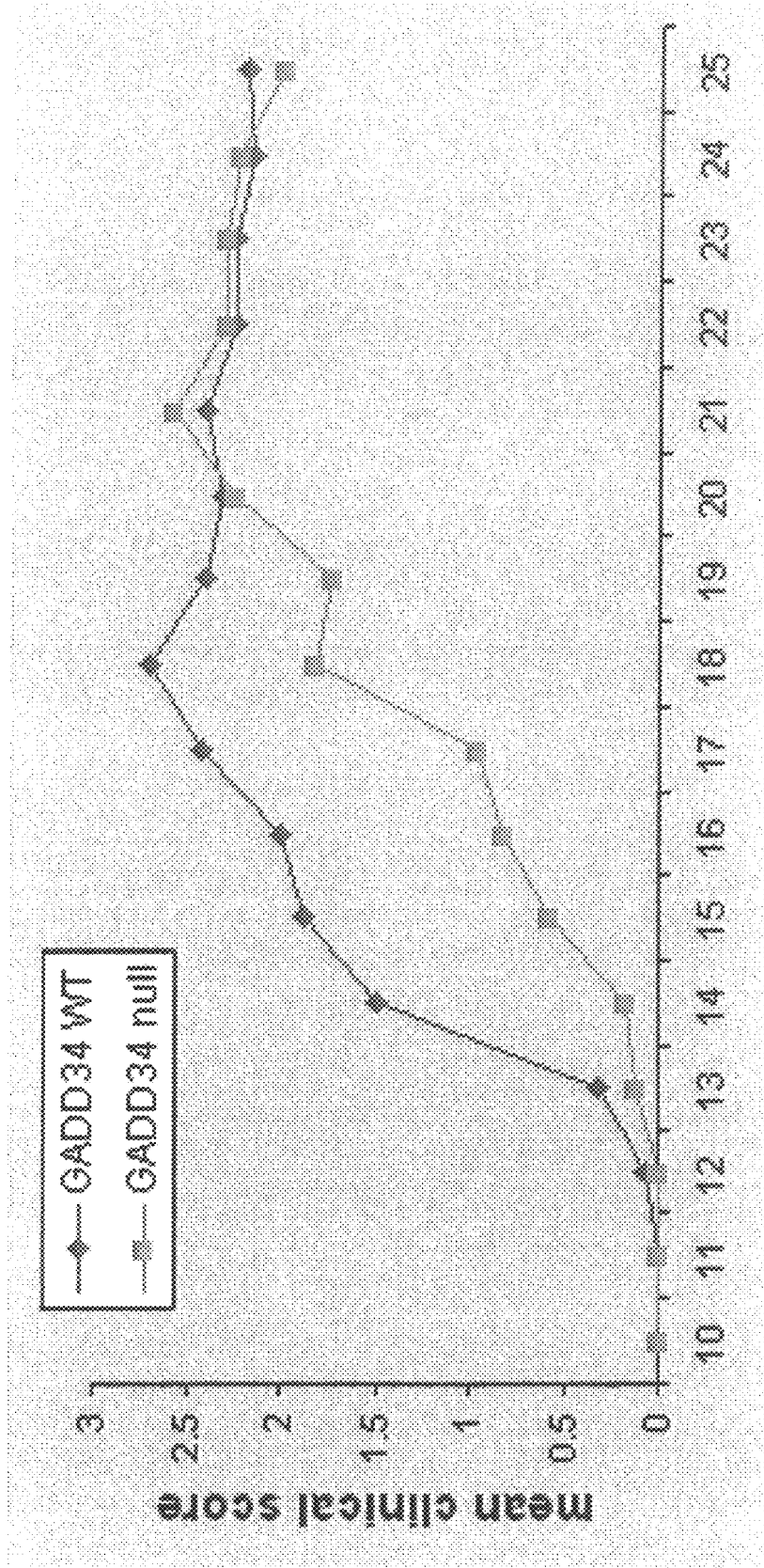
FIG. 26 shows that the clinical disease onset in the GADD34-null mice is delayed when compared with the onset in littermate control mice. Mean clinical disease severity score, n=6.

The results in FIG. 26 show that the onset of the disease is significantly delayed in the GADD34-null mice when compared to the control animals. Therefore, inhibition of GADD34 delays the onset of EAE.

Tissue damage in the CNS is determined by immunohistochemistry analysis and toluidine blue staining as described by Lin et al. (submitted). Spinal cord tissue is analyzed for tissue damage at the peak of disease severity. An antibody against CC1 (APC7) is used as a marker to identify mature oligodendrocytes; an antibody against MBP is used to determine the degree of demyelination; and an antibody against nonphosphorylated neurofilament-H (SMI32) is used to detect axonal damage. In addition, the severity of demyelination and axonal injury is examined by staining the tissue with toluidine blue. As myelin gene expression is highly correlated with oligodendrocyte function, real-time PCR is perfomed to determine the steady-state levels of mRNAs that encode for MBP, PLP, and ceramide galactosyltransferase (CGT) in the spinal cord. The Taqman real-time PCR allows for quantifying the degree of demyelination in the lesions.

The results show that progression of EAE is accompanied by a decrease in mRNAs encoding MBP, PLP and CGT in both GADD34-null mice and the wild type controls. However, the decrease in the GADD34-null mice precedes that seen in the wild type animals.

It is expected that the histological results will be consistent with the time course of the disease as assessed by the phenotypic changes that were quantified using clinical scores, and it is likely that loss of function of GADD34 protects from demyelination and from the loss of oligodendrocytes that is characteristic of EAE.

Example 18

Loss of GADD34 Protects Oligodendrocytes from Aginst Demyelination During EAE

Diverse stressful conditions are associated with phosphorylation of eIF2α. Four mammalian eIF2α kinases have been identified: PERK, GCN2, RNA-activated protein kinase (PKR), and HRI (Proud, 2005). As described in the Examples above the PERK-eIF2α pathway is activated in oligodendricytes during EAE by the immune cytokine IFN-γ. Chakrabarty et al. (2004) have shown that activation of the PKR-eIF2α pathway occurs in inflammatory cells in the CNS of animals with active EAE.

To confirm that the effect seen in the mice having EAE but lacking GADD34 reflects the protection of oligodendrocytes, double immunostaining of CC1 and p-eIF2α is performed in the GADD34-null mice and compared to that performed in the wild type control animals.

In addition, double immunostaining of CD3 and p-eIF2α is performed to determine whether the level of p-eIF2α is increased in T cells in the CNS of the GADD34-null mice when compared to the wild type animals. The immune responses in the CNS and peripheral immune system in GADD34-null and littermate control mice are analyzed as described in Lin et al. (submitted).

It is expected that the results will indicate that the level of p-eIF2α is greater in the oligodendrocytes of the GADD34-null mice than in the wild type mice. Without being bound by any particular theory, enhancing the phosphorylation of eIF2α is expected to prolong the integrated stress response and thus oligodendrocytes from the damage caused by EAE.

Example 19

The Role of GADD34 in Demyelination: Effects of the Loss of Function of GADD34 In Vitro To evaluate the protective effects seen in oligodendrocytes and gained by the loss of GADD34 deletion, experiments that use siRNA to block the expression of GADD34 are performed on purified rat oligodendrocytes in culture. The experimental protocol is described by Lin et al. (submitted). Oligodendrocyte progenitors (OPCs) are cultured from neonatal rat brain as follows. A mixed glial culture is grown in flasks in medium containing 10% FBS, and when the astrocyte layer becomes confluent (after 10-14 days), OPCs are separated from astrocytes and microglia using an orbital shaker. More than 95% of the cells are A2B5 positive, GFAP negative, and CD11b negative, and are first cultured in medium containing 0.5% FBS, PDGF (10 ng/mL), and FGF (5 ng/mL), then transferred to 0.5% FBS medium without PDGF and FGF to induce differentiation.

Small interfering RNA (siRNA) is designed using siRNA Target Finder software (Ambion). and used to inhibit the expression of the rat GADD34. The target sequence of the siRNA is used in conjunction with the pSilencer Expression Vectors Insert Design Tool (Ambion) to generate hairpin siRNA that encodes DNA oligonucleotide inserts that are derived from the siRNA target sequence. The program adds the loop sequence and overhangs that are used for cloning. The hairpin siRNA-encoding DNA oligonucleotide inserts are cloned into the pSilencer 4.1-CMV vector (Ambion) according to the manufacturer's instructions, and the pSilencer 4.1-CMV vectors encoding hairpin siRNAs that are specific for GADD34 will be transfected into OPCs using the Nucleofector kit (Amaxa) according to the protocol of the manufacturer. Control oligodendrocytes are transfected with control vectors that are pSilencer 4.1-CMV vectors that lack GADD34 siRNA. After transfection, the cells are selected with 2.5 μg/mL puromycin over a period of 10-14 days. The transfected OPCs are analyzed for the presence GADD34 mRNA using Taqman real-time PCR and for the presence of GADD34 protein using Western blot analysis.

It is expected that the results suggest that siRNA specific for the GADD34 gene successfully inhibits the transcription of GADD34 and the expression of the GADD34 protein.

In addition, the protective effect of salubrinol (Sal) is tested to determine whether Sal protects oligodendrocytes from cytokines, oxidants, peroxynitrite donors, and glutamate. Salubrinol has been shown to specifically inhibit the PP1-GADD34 phosphatase activity, which results in sustained eIF2α phosphorylation in stressed cells (Boyce et al., 2005). Sal is combined with TNF-γ, $H_2O_2$, the peroxynitrite donor SIN-1, and glutamate is added to the cells that have been allowed to differentiate for 7 days. Western blot analysis is used to examine whether Sal elevates the level of p-eIF2α in cultured oligodendrocytes. Also, the viability of oligodendrocytes is determined by the MTT assay (Roche), the TUNEL assay (ApopTag kit; Serologicals), and the caspase-3 activity assay (Sigma, St. Luis, Mo.) as described by Lin et al., 2001 and 2005.

The results indicate that inhibiting the function of GADD34 by blocking its expression using siRNA technology or by directly inhibiting its enzymic activity protects oligodendrocytes from reactive oxidative/nitrative stress and glutamate cytotoxicity. Histologic analyses at the peak of disease will reveal that GADD34 deletion elevates the level of p-eIF2α in oligodendrocytes and protects against EAE-induced demyelination and oligodendrocyte loss. It is expected that GADD34 siRNA transfection and Sal will protect oligodendrocytes from cytokine exposure, reactive oxidative/nitrative stress, and glutamate excitoxicity. Various aspects of the cytoprotective effects of Sal with those of GADD34 siRNA transfection are compared. The protective effects of Sal in mice with EAE and persons with MS are tested.

Example 20

Activation of the PERK-Dependent Integrated Stress Response Pathway in Oligodendrocytes Protects Against Demyelination The activation of the PERK pathway is initiated by dimerization of PERK, which leads to trans-autophosphorylation and increased ability to phosphorylate its substrate, eIF2α. Normally, this dimerization event is driven by the stress-sensing ER lumenal domain of PERK (Harding 1999). Other researchers have fused the eIF2α kinase effector domain of PERK to a polypeptide containing 2 modified FK506 binding domains (Fv2E) to generate a fusion protein, Fv2E-PERK, and have demonstrated that the activity of this artificial eIF2α kinase, Fv2E-PERK, is subordinate to the dimerizer AP20187 and is uncoupled from upstream signaling of ER stress (Lu et al., 2004).

To examine the protective effects of PERK activation on oligodendrocytes in vitro oligodendrocyte precursor cells (OPCs) are transfected with a construct encoding Fv2E-PERK, The Fv2E-PERK construct is subcloned into the mammalian vector pcDNA3.1 to generate a mammalian expression plasmid that expresses a fusion protein Fv2E-PERK protein (pcDNA3.1-Fv2E-PERK). Purified rat OPCs as described above are transfected with pcDNA3.1-Fv2E-PERK using the Nucleofactor kit (Amaxa), and selected with G418 (400 ug/ml) for 10-14 days.

The OPCs are induced to differentiate for 7 days, and the activation of the PERK-eIF2α pathway is evaluated in the presence of the dimerizer AP20187 alone, or in combination with one of TNF-γ, $H_2O_2$, peroxynitrite donor SIN-1, or glutamate.

The expression of mRNA encoding Fv2-PERK is verified using real time PCR, and the expression of Fv2-PERK protein is verified by Western blot analysis. The effect of the activation of the PERK-eIF2α pathway is assessed by Western blot analysis for p-eIF2α following addition of AP20187 to the transfected OPCs. Further, the viability of transfected oligodendrocytes is determined using the MTT assay, TUNEL assay, and caspase-3 activity assay, as described above following differentiation of OPCs for 7 days. The same analyses are made following administration of AP20187 to the OPCs in the presence of TNF-a, H202, peroxynitrite donor SIN-1, or glutamate. Oligodendrocyte viability is determined by MTT and TUNEL assays, and caspase activity.

It is expected that AP20187 will protect the Fv2-PERK-expressing oligodendrocytes from effector(s) of the ER stress pathway.

Example 21

Identification of Genes that are Upregulated by Activation of the PERK Pathway

To determine the mechanisms accounting for the protective effects of activation of the PERK pathway on oligodendrocytes, mRNA microarray analysis is used to identify the cytoprotective genes that are upregulated.

OPCs that have been transfected with pcDNA3.1-Fv2E-PERK are differentiated for 7 days and treated with AP20187. RNA is isolated from AP20187-treated transfected cells and control transfected cells by using Trizol reagent (Invitrogen), and DNAseI (Invitrogen) is added to eliminate genomic DNA. Fluorescent-labeled RNA probes are prepared and hybridized to Affimetrix rat high-density oligonucleotide arrays. Primary image analysis of the arrays is performed using the Genechip software package (Affymetrix). The raw data is also be analyzed by means of GeneSpring software. Only genes whose raw hybridization signal is significantly stronger than that of the chip background is evaluated. The raw signal strength for each gene is normalized to the mean signal strength of all genes from the same chip to obtain the normalized signal strength. To allow visualization of all data on the same scale for subsequent analysis, the normalized signal strength of each gene is divided by the median signal strength for that gene among all samples to obtain the expression level.

The results show that cytoprotective genes that are involved in the protective effects of the PERK pathway in EAE are identified. The role of the newly-identified genes in the in the pathogenesis of EAE is evaluated.

Example 22

Activation of the PERK-eIF2α Pathway Provides Cytopoprotection to Oligodendrocytes During EAE To provide direct evidence that activation of the PERK-eIF2α pathway protects against EAE-induced tissue damage through its cytoprotective effects on oligodendrocytes, the activity of PERK is modulated in mice that allow for controllable activation of the PERK pathway in oligodendrocytes.

Based on methods previously used to generate transgenic mice that express proteins specifically in oligodendrocytes under the transcriptional control of the regulatory sequences of the myelin proteolipid protein (PLP) gene (Fuss et al., 2000, 2001; Doerflinger et al., 2003), an expression construct that expresses the fusion Fv2E-PERK (PLP/Fv2E-PERK) is engineered, and transgene fragments are injected into fertilized C57BL/6 mouse oocytes.

Several lines of PLP/Fv2E-PERK transgenic mice that express various levels of the transgene are obtained, and transgene expression is found not to be deleterious to the animals. Quantitative real-time PCR is used to determine copy numbers of the transgene that integrates into the genome of heterozygous animals, and the level of Fv2E-PERK mRNA and protein in the CNS is determined using real-time PCR and Western blot analysis; The transgenic mice are given intraperitoneal injections of AP20187, and the activity of Fv2E-PERK in the CNS is determined by Western blot analysis for p-Fv2E-PERK and p-eIF2α. Finally, CC1 and p-eIF2α double immunostaining is perfomed to confirm that the eIF2α pathway is specifically activated in oligodendrocytes in the transgenic mice that received AP20187.

The transgenic mice that allow for modest activation of the PERK pathway in oligodendrocytes after administration of AP20187 are selected for EAE experiments. The mice are immunized with MOG33-35 peptide as described in Example and Fv2E-PERK in oligodendrocytes is activated by administering AP20187 before the onset of EAE onset. The activation of eIF2α in oligodendrocytes is verified by CC1 and p-eEF2α double immunostaining, and the clinical phenotype, the histopathologic findings in the CNS, and the immune response in the CNS are characterized as described-in the Examples above.

Example 23

Activation of PERK Pathway in Remyelinating Oligodendrocytes Promotes Remyelination in EAE-Induced Demyelinated Lesions To determine that the activation of the PERK pathway promotes remyelination of oligodendrocyte in EAE-induced demyelinated lesions, EAE is induced in PLP/Fv2E-PER mice, and the role of PERK is evaluated in the presence and absence of AP201187.

The PLP/Fv2E-PERK mice are immunized with MOG33-35 peptide as described in Example, and Fv2E-PERK is activated in oligodendrocytes by administering AP20187 to the mice during the recovery stage of EAE. Clinical severity scores were recorded daily according to a 0-5 point scale, where 0=healthy, 1=flaccid tail, 2=ataxia and/or paresis of hind limbs, 3=paralysis of hind limbs and/or paresis of forelimbs, 4=tetraparalysis, and 5=moribund or dead.

The activation of eIF2α in oligodendrocytes is verified by CC1 and p-eIF2α double immunostaining. Once the severity of disease between AP20187-treated mice and control mice appears to be significantly different, spinal cord tissue is prepared and analyzed for remyelination. As described elsewhere (Lin et al., submitted), CC1 immunostaining is used to determine the mature oligodendrocyte numbers in the demyelinated lesion, and immunostaining for MBP and toluidine blue staining is used to verify the degree of demyelination. The immune response in the CNS is assessed by immunostaining for CD11b and CD3 immunostaining, and by real-time PCR analyses for IFN-γ, TNF-γ, iNOs, IL-2, IL-4, IL-5, IL-10, IL-12, IL-17, and IL-23.

Example 24

The PERK-eIF-2α Pathway is Activated in Oligodendrocytes from Lesions in Patients with MS CNS tissue of patients with MS is obtained from the Human Brain and Spinal Fluid Resource Center (Los Angeles, Calif.) and The Rocky Mountain MS Center (Englewood, Colo.). The tissue may include brain and spinal cord tissues, spinal fluid, and other tissue specimens that are derived from persons who have had MS in their lifetime. The samples are frozen or otherwise preserved very soon after the death of the donors, and the banked tissues are carefully catalogued along with information about the donor's medical history and are available to qualified investigators.

Total RNA is isolated from the frozen samples using Trizol reagent (Invitrogen) and treated with DNAseI (Invitrogen) to eliminate genomic DNA. Reverse transcription is performed using the Superscript First Strand Synthesis System for RT-PCR kit (Invitrogen). Using Taqman real-time PCR, the expression of IFN-γ and the ER stress markers BIP and CHOP is quantified. The protein levels of PERK, eIF2α, p-PERK, and p-eIF2α are determined using Western blot analysis.

The remaining frozen tissue will be embedded in optimal cutting temperature compound. Frozen sections (10 μm thick) of the tissue samples are prepared, and CC1 immunostaining is used to determine the number of oligodendrocytes in the demyelinated lesions. MBP immunostaining is used to verify the degree of demyelination. The immune response in the CNS is assessed by CD11b immunostaining and CD3 immunostaining. Furthermore, CC1 and p-PERK double immunostaining, or CC1 and p-eIF2α double immunostaining is performed to demonstrate the activation of the PERK-eIF2α pathway in MS lesions.

On the basis of the distribution and density of inflammatory cells and activated microglia, demyelinated MS-induced lesions can be divided into the following 3 categories: active (acute), chronic active, and chronic inactive (Lassmann, 1998; Trapp et al., 1999). The relationship between the levels of IFN-γ and the activity of the PERK pathway in the samples, and the relationship between the degree of demyelination and the activity of the PERK pathway in the lesions, is determined.

It is expected that the PERK-eIF2α pathway is activated in the oligodendrocytes of MS lesions. Because of the heterogenous patterns of demyelination in MS, the activation of the PERK-eIF2α pathway is expected to be detected in only some of the tissue samples.

Example 25

Deletion of GADD34 Increases the Level of p-eIF2α in Oligodendrocytes and Protects Against EAE-Induced Demyelination 1. Studies In Vivo Phosphorylation of eIF2α is a highly conserved point of convergence among signaling pathways that adapt eukaryotic cells to diverse stressful conditions (Jousse et al (2003) *J. Cell. Biol.* 163:767-775; Proud CG (2005) *Semin. Cell. Dev. Biol.* 16:3-12). Four protein kinases are known to couple the otherwise unrelated stresses of protein malfolding in the ER (PERK), amino acid deprivation (GCN2), viral infection (PKR) and heme deficiency (HRI) to the phosphorylation of eIF2α (Proud CG (2005) *Semin. Cell. Dev. Biol.* 16:3-12). This eIF2α phosphorylation-dependent, stress-inducible pathway has been referred to as an integrated stress response (ISR) (Harding, et al (2003) *Mol. Cell* 11:619-633; Proud CG (2005) *Semin. Cell. Dev. Biol.* 16:3-12). To recover from stress, eIF2α is quickly dephosphorylated by a complex containing the enzyme phosphatase (PP1) and its essential non-enzymatic cofactor, growth arrest and DNA damage 34 (GADD34) (Connor, et al. (2001) *Mol. Cell. Biol.* 21: 6841-6850; Novoa et al (2001) *J. Cell Biol.* 153:1011-1022; Novoa et al (2003) *EMBO J.* 22:1180-1187). The expression of GADD34 is regulated by induction of the cytosolic transcription factor ATF4, the translation of which is upregulated in the presence of eIF2α phosphorylation, thus creating a tight autofeedback loop (Novoa et al (2003) *EMBO J.* 22:1180-1187; Jiang et al (2004) *Mol. Cell. Biol.* 24:1365-1377). GADD34 deletion increases the level of p-eIF2α in stressed cells and protects cells from stress (Jousse et al (2003) *J. Cell. Biol.* 163:767-775; Marciniak et al (2004) *Genes Dev.* 18:3066-3077).

As shown in the examples above, early induction of IFN-γ in the CNS has a protective effect in animals induced to develop EAE, and that this protection is dependent on PERK. To test whether the early presence IFN-γ activates the integrated stress response (ISR) through the activation of PERK in oligodendrocytes, and protects them from inflammatory demyelination, the effect of EAE was examined in GADD34 mutant mice. It was expected that in the absence of GADD34, the prolonged stress response would be beneficial.

a. The Onset of EAE is Significantly Delayed in GADD34-Null Mice

EAE was induced in GADD34-null mice and control animals as described in Example 17. Briefly, GADD34-null mice were backcrossed with C57BL/6 mice at least 6 times. EAE was induced in mice by administering to the mice a subcutaneous injection of 200 μg MOG 35-55 peptide emulsified in complete Freund's adjuvant supplemented with 600 μg of *Mycobacterium tuberculosis* in the flank and tail base. Two 400-ng intraperitoneal injections of pertussis toxin were given 24 and 72 h later. Clinical severity scores were recorded daily using a 0-5 point scale (0=healthy, 1=flaccid tail, 2=ataxia and/or paresis of hind limbs, 3=paralysis of hind limbs and/or paresis of forelimbs, 4=tetraparalysis, and 5=moribund or dead).

Figure 27:
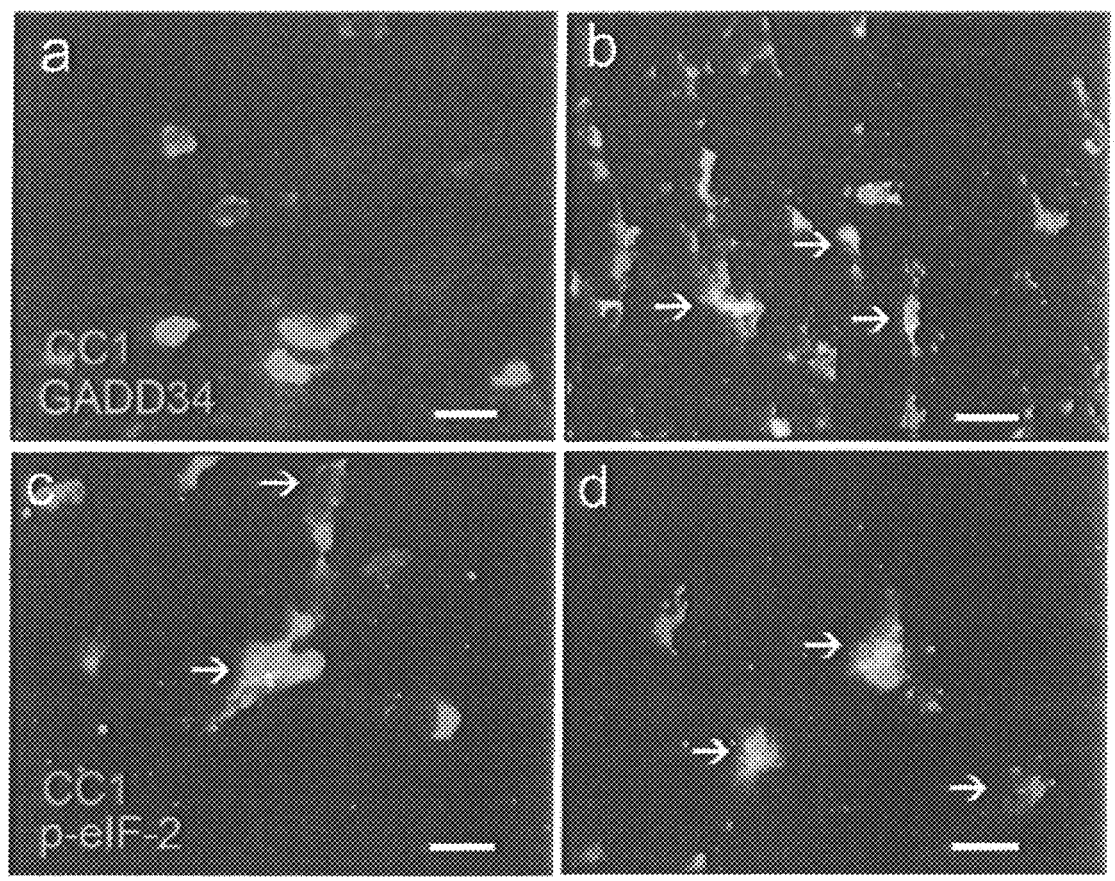
FIG. 27 shows dual label immunohistochemical analysis of the effect of the loss of function of GADD34. (a) GADD34 was undetectable in oligodendrocytes from the spinal cord of 8-week old naive mice. (b) The arrow points to GADD34 that was upregulated in oligodendrocytes of control mice with EAE at PID 17 (scale bar=15 μm, n=3 mice per study group). (c) The arrow points to double labeling of CC1 and p-eIF2α, which showed modest activation of eIF2α in a few oligodendrocytes of the lumbar spinal cord of control mice with EAE at PID17. (d) CC1 and p-eIF2α double labeling showed the level of p-eIF2α was increased in oligodendrocytes (arrow) in GADD34 null mice at PID17. N=3, Scale bar=10 μm.
Figure 28:
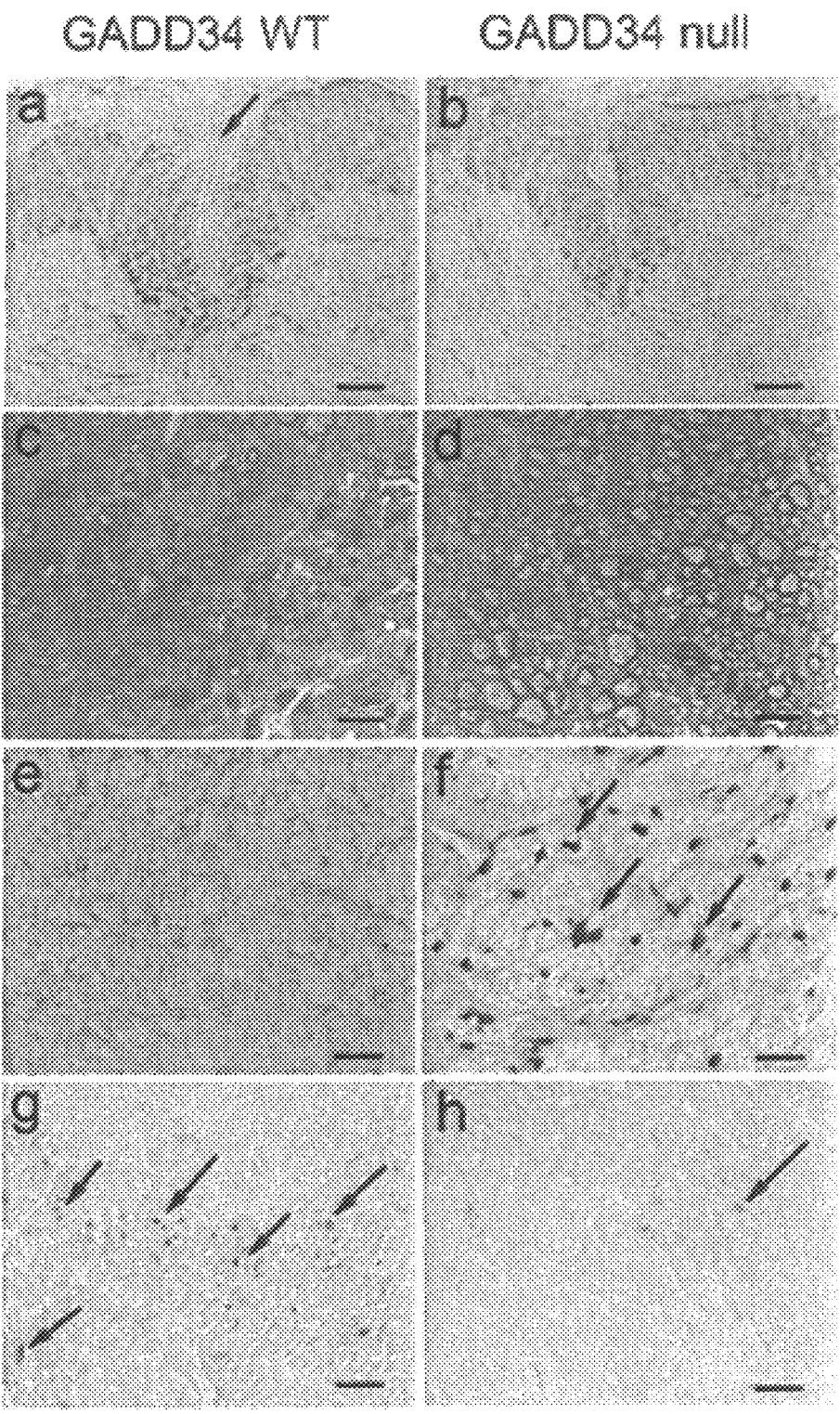
FIG. 28 shows immunostaining of MBP in sections of the lumbar spinal cord from GADD34-null mice and control mice. (a) and (b) show MBP immunostaining of the lumbar spinal cord tissue from GADD34 wild-type and GADD34-null mice, respectively. The arrow points to a demyelinating lesion seen in control mice with EAE at PID17 (a), while no obvious demyelinating lesion was observed in GADD34 null mice with EAE at PID17 (b) (n=3, scale bar=50 µm.). (c) and (d) show that toluidine blue staining of sections of the lumbar spinal cord of GADD34 wild-type and GADD34-null mice, respectively. Severe demyelination in the lesions in the lumbar spinal cord of control mice at PID17 (c), whereas GADD34 deletion protected against EAE-induced demyelination in the lumbar spinal cord of GADD34 null mice at PID 17 (d) (n=3, scale bar=10 µm). (e) and (f) CC1 immunostaining of the lumbar spinal cord tissue from GADD34 wild-type and GADD34-null mice, respectively. (e) shows that the majority of oligodendrocytes in the demyelinating lesions in the lumbar spinal cord of control mice were lost at PID17, whereas the oligodendrocytes (arrow) in the lumbar spinal cord of GADD34 null mice remained almost intact. (f) (n=3, scale bar=25 µm). (g) and (h) show immunostaining of non-phosphorylated neurofilament-H immunostaining of lumbar spinal cord tissue from control and GADD34-null mice, respectively. Severe axonal damage is shown by the arrow in the demyelinating lesions in control mice at PID17 (g), whereas mice with the GADD34 deletion had markedly reduced axonal damage (arrow) in the lumbar spinal cord of GADD34 null mice (h) (n=3, scale bar=25 µm).

The clinical disease onset in GADD34-null mice is significantly delayed when compared with the onset in littermate control mice (FIG. 26). In addition, the severity of disease in the GADD34-null mice was milder than control mice. Therefore, loss of GADD34 function delays the onset of EAE and diminishes the severity of the disease.

b. Loss of GADD34 Increases the Level of p-eIF2α in Oligodendrocytes and Protects Against EAE-Induced Demyelination Spinal cord tissue was prepared and analyzed at the time point when control mice were at the peak of disease severity. As expected, the expression of GADD34 was upregulated in oligodendrocytes in the lumbar spinal cord of mice with EAE, which was undetectable in oligodendrocytes in the age-matched naïve mice (FIGS. 27a and 27b). Moreover, CC1 and p-eIF2α double labeling revealed that GADD34 deletion markedly increased the level of p-eIF2α in oligodendrocytes in the lumbar spinal cord of GADD34 null mice with EAE, compared with control mice (FIGS. 27c and 27b). Histological analysis revealed typical EAE demyelinating lesions in the lumbar spinal cord of control mice: destruction of myelin sheaths (FIGS. 28a and 28c), oligodendrocyte loss (FIG. 28e) axonal damage (FIG. 28g). In contrast, no obvious demyelinating lesion was observed in the lumbar spinal cord of GADD34 null mice by MBP immunostaining and toluidine blue staining at this time point (FIGS. 28b and 28d). Importantly, oligodendrocytes in the lumbar spinal cord of GADD34 null mice remained almost intact (FIG. 28f). Moreover, GADD34 deletion dramatically reduced the axonal damage in the lumbar spinal cord of GADD34 null mice, compared with control mice (FIGS. 28g and 28h). Taken together, these data indicate GADD34 deletion increases the level of p-eIF2α in oligodendrocytes, thus prolongs in the integrated-stress response and protects against EAE-induced demyelination.

2. Studies In Vitro

The importance of the phosphorylation of eIF2α in protecting the cell from stress has lead to the search for small-molecule modulators of the phosphorylation of eIF2α that could potentially be useful for the treatment of several human diseases. Boyce et al. (Boyce, et al. (2005) Science 307:935-939) used a drug screen that would identify small molecules that confer cytoprotection against ER-stress-induced apoptosis. They identified a small-molecule inhibitor of eIF2α dephosphorylation, salubrinal (SAL), which specifically inhibits the PP1-GADD34 phosphatase activity, resulting in sustained eIF2α phosphorylation. Treatment with Sal protects cells from ER stress and viral infection (Boyce, et al. (2005) Science 307:935-939).

Our hypothesis is that the integrated stress response has the potential to protect oligodendrocytes from the harmful effects of the inflammatory response in patients with multiple sclerosis (MS). As shown above mice with a null mutation in GADD34 demonstrate increased eIFα phosphorylation and a delayed response to EAE induction, including less severe demyelinaiton at the peak of disease. To test whether agents that prolong eIF2α phosphorylation might provide protection to oligodendrocytes against detrimental inflammatory factors, the effect of Salubrinol (Sal) in the presence of the immune cytokine IFN-γ was tested in an in vitro model of myelination.

Figure 29A:
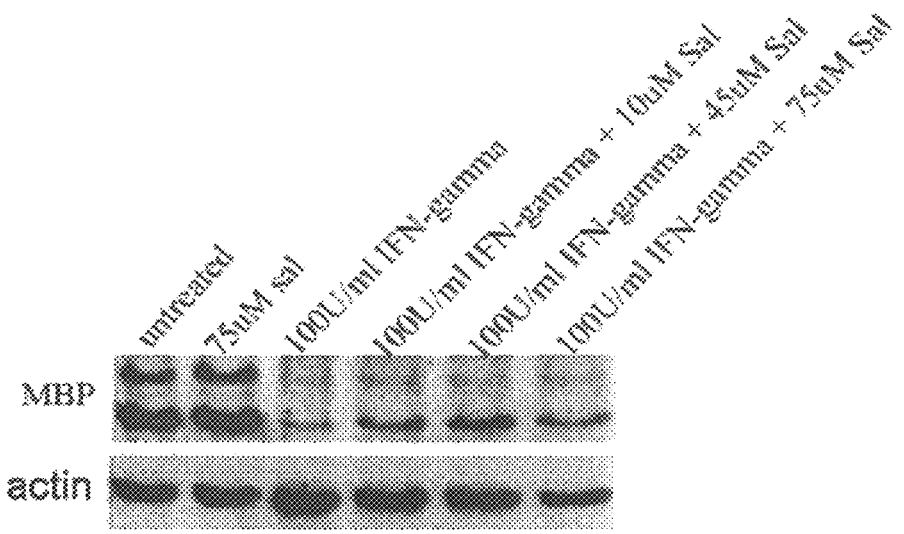
FIG. 29 shows the attenuating effect of Sal on the reduction of MBP levels mediated by INFγ by Western blot analysis (A), and densitometric analysis of the MBP protein bands normalized to actin (B).
Figure 29B:
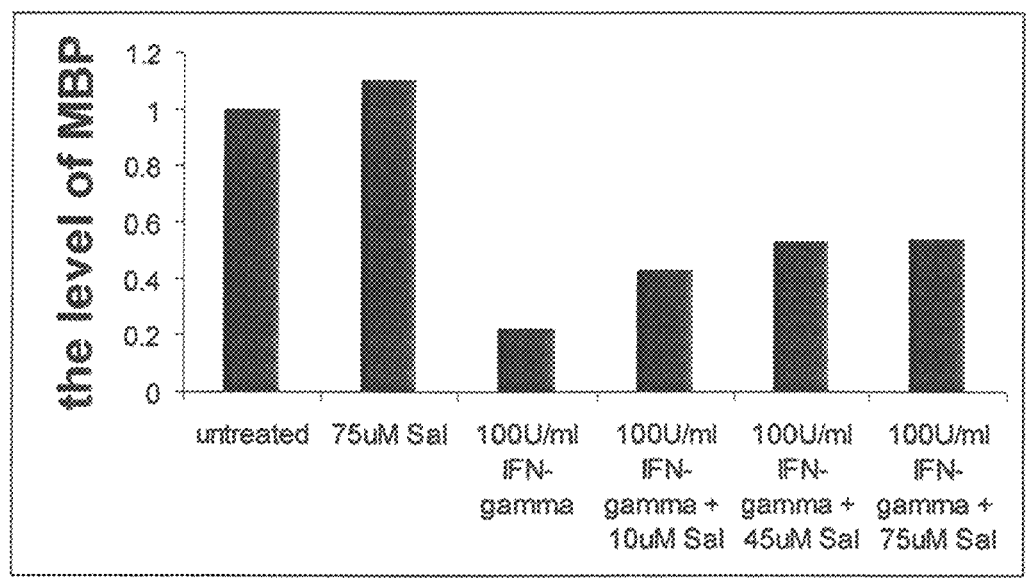

Hippocampal organotypic cultures (HOC), which have been shown to myelinate well in vitro. HOCs, were prepared and maintained as described previously (Kunkler and Kraig (1997) J Cereb Blood Flow Metab. 17:26-43), and were maintained in vitro for 7 days before use. SAL at various concentrations was combined with 100 U/ml IFN-γ and added to the HOC cultures for 7 days. Robust myelination was observed in untreated HOCs, as demonstrated by abundant levels of the myelin-specific protein myelin basic protein (MBP) in the cultures (FIG. 29). After 7 days of 100 U/ml IFN-γ exposure, the levels of MBP decreased approximately 80% in the HOCs (FIG. 29). SAL treatment alone did not affect MBP expression. However, SAL treatment markedly attenuated the reduction of MBP expression elicited by IFN-γ exposure (FIG. 29). The presence of IFN-γ has been shown to inhibit remyelination in demyelinated lesions (See Examples 2-7). Taken together, these data indicate that treatment with agents that promote or prolong eIF2α phosphorlyation could promote myelin repair in immune-mediated demyelination diseases.

Example 26

Inhibition of the Cytokine Signaling Protects Oligodendrocytes from the Deleterious Effects of INF-γ

Figure 30:
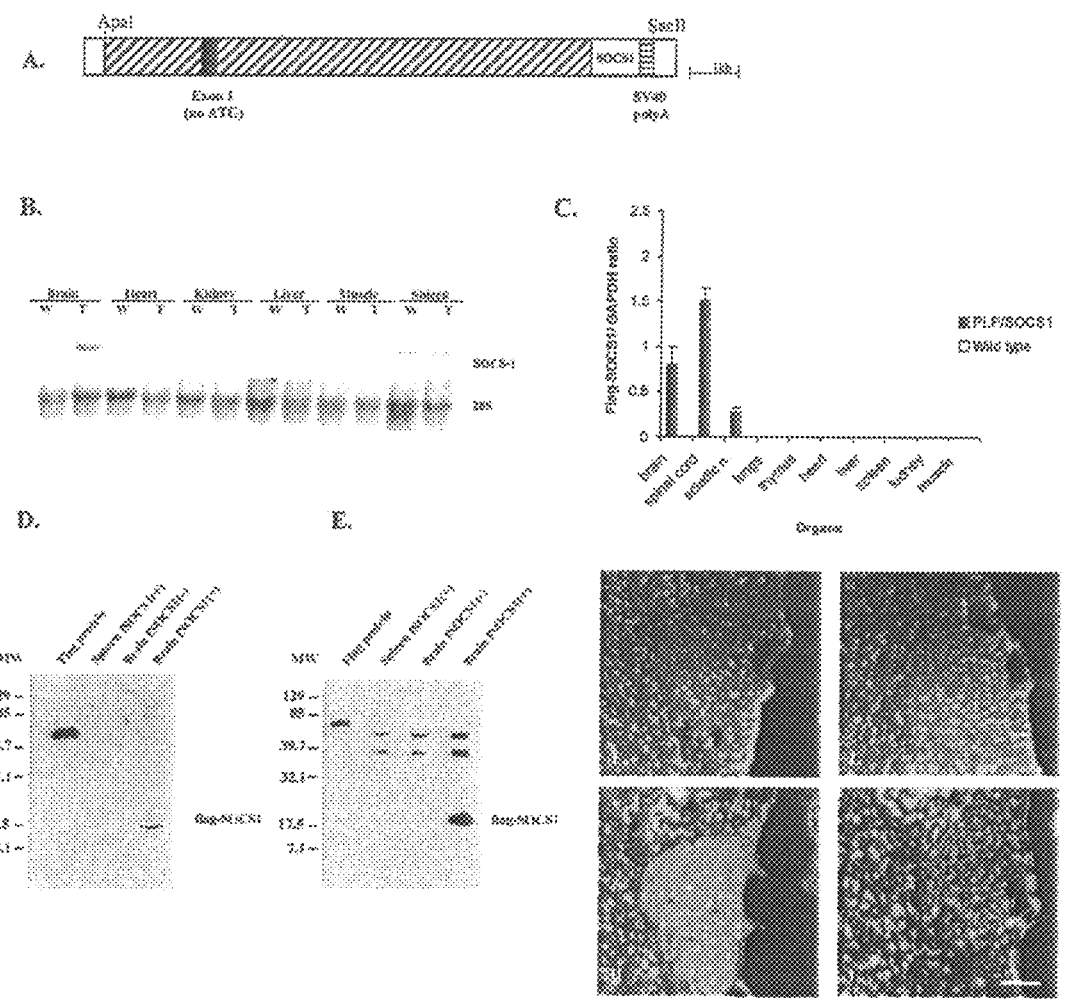
FIG. 30 shows the expression of Flag-SOCS1. A. PLP/SOCS1 construct contains 2.4 Kb of the PLP 5' flanking DNA, exon 1 (no ATG), intron 1 (diagonally striped boxes), Flag-SOCS1 and SV40 polyA signal sequence. Expression of the PLP/SOCS1 transgene was characterized at postnatal day 21 using several methods. B. Northern blot analysis demonstrated Flag-SOCS1 expression in PLP/SOCS1 brain, lane 2 (T, transgenic brain), compared to wild-type brain, lane 1 (WT, wild-type brain). C. Q-PCR analysis with transgene-specific primers revealed the highest concentrations of transgene-derived SOCS1 mRNA were in the brain, spinal cord, and sciatic nerve, with significantly lower levels in other organs. D. Western blot. E. Immunoprecipitation. Both demonstrated a single 19 KD Flag positive band, the expected molecular weight of SOCS1, only in the lanes loaded with brain samples from PLP/SOCS1 mice (brain fSOCS1+). Flag protein was used as a positive control for the antibody reaction; 15% SDS-PAGE, anti-Flag (M2) antibody. Immunostaining with anti-SOCS1/FITC (F, H, green), and anti-Flag/FITC antibodies (G, I, green) demonstrated positive signal only in PLP/SOCS1 (H, I, green), and not in the wild-type mouse samples (F, G). Cell nuclei were contrastained with ethidium bromide (F-I, red). Coronal section sections of thalamic fiber; Bar=20 µm.

1. Generation and Evaluation of Transgenic Mice a) Generation of Transgenic Mice that Express SOCS1 in Oligodendrocytes The transgenic mouse line PLP/SOCS1 was generated using a construct containing a PLP expression cassette and SOCS1 cDNA (FIG. 30A). The PLP expression cassette has been described elsewhere and has been used for oligodendrocyte-specific expression of a number of transgenes (Wight et al., 1993; Fuss et al., 2000; Doerflinger et al., 2003; Gonzales et al., 2005). A SOCS1 cDNA clone (Starr et al., 1998) was used as it contained a Flag-epitope sequence that served as a marker for SOCS1 expression in polymerase chain reaction (PCR)-based or anti-Flag antibody-based detection methods (Einhauer and Jungbauer, 2001). Briefly, the Flag-SOCS1 cDNA was excised from the original expression vector pEF-FLAG-I/m4A2 with XbaI. The fragment was Klenow filled and subcloned into an intermediate vector (modified pNEB/193 vector) at the SmaI restriction site. The resulting pNEB193/SOCS1 vector was further digested with AscI (partial digestion) and PacI to release the Flag-SOCS1 fragment, which was subcloned into the polylinker region of the PLP expression cassette at the same restriction sites. The PLP/SOCS1 vector was digested with ApaI and SacII (partial digestion) and a linear 15-kb transgene was isolated for microinjection into fertilized (C57BL/6J×DBA/2J) oocytes. Offspring positive for the transgene were identified by amplifying tail DNA by PCR using transgene-specific primers. The identified founders were subsequently bred with C57BL/6J mice (Jackson Laboratories, Bar Harbor, Me.) establishing a transgenic line.

b) Generation of Lines of Transgenic Mice that Express INF-γ in the CNS

The transgenic mice MBP/IFN-γ (line 172) and GFAP/tTA×TRE/IFN-γ (lines 184/110 and 184/67) that overexpress IFN-γ in the CNS have been described elsewhere (Corbin et al., 1996; Gao et al., 2000; Lin et al., 2004, 2005). Briefly, MBP/IFN-γ (line 172) mice are transgenic animals in which IFN-γ expression is driven by the myelin basic protein (MBP) transcriptional control region (Gao et al., 2000). GFAP/tTA×TRE/IFN-γ are double-transgenic mice obtained by mating single-transgenic GFAP/tTA (line 184) to single-transgenic TRE/IFN-γ (lines 110 and 67) mice. The two TRE/IFN-γ mouse lines, line 110 and line 67, used in the experiments produce different amounts of IFN-γ when crossed to GFA/tTA mice (184/110 and 184/67) (Lin e al., 2004, 2005). GFAP/tTA×TRE/IFN-γ is a tetracycline-off-inducible system in which the glial fibrilary acidic protein (GFAP) transcriptional control region drives the expression of tTA, which in turn, binds to the TRE (tet responsive element) and initiates the expression of IFN-γ. Administration of doxycycline suppresses tTA DNA binding and IFN-γ expression, and doxycycline removal allows for temporally-controlled induction of IFN-γ expression (Gao et al., 1999).

c) Breeding and Evaluation of Transgenic Animals

IFN-γ-overexpressing mice were crossed to the PLP/SOCS1 mice in double-transgenic, (MBP/IFN-γ×PLP/SOCS1) and triple-transgenic (GFAP/tTA×TRE/IFN-γ×PLP/SOCS1) mating systems. MBP/IFN-γ×PLP/SOCS1 (172×PLP/SOCS1) mating was performed according to a standard mating protocol. The GFAP/tTA×TRE/IFN-γ×PLP/SOCS1 matings were performed in a 2-step mating process:

GFAP/tTA mice (line 184) were initially crossed to PLP/SOCS1 mice, and double-positive (184×PLP/SOCS1) offspring were then crossed to the TRE/IFN-γ lines 110 and 67, separately. This second mating step was performed according to the previously described "tet-off" protocol. Doxycycline 0.05 mg/ml (Sigma-Aldich) was added to the water of impregnated female mice until embryonic day 14, after which the animals were switched back to normal water, thereby allowing initiation of IFN-γ transcription, which peaks during the postnatal period (Lin et al., 2005).

The litters of the mating systems (F1 generation) were examined daily and sacrificed at postnatal day 21. Clinical evaluation included behavioral observation and challenged ladder walking to elicit tremor. Histological examination included quantitation of the number and density of oligodendrocytes and examination of the myelination patterns. Brain tissue was simultaneously obtained from each animal at the time of sacrifice to verify and measure the expression of IFN-γ and Flag-SOCS1 (see below). The clinical and histological findings were subsequently stratified according to genotype. All animal procedures were conducted in compliance with the *National Institutes of Health Guide for Care and Use of Laboratory Animals* and were approved by the Institutional Animal Care and Use Committee at The University of Chicago.

d) Polymerase Chain Reaction and Genotyping of Transgenic Animals

All experimental animals were genotyped using isolated tail DNA (Biotek 2000 automatic system, Beckman-Coutler, Fullerton, Calif.). PCR (Qiagen PCR kit, Valencia, Calif.) for transgene detection was performed using the following transgene-specific screening primers: Flag-SOCS1 sense primer, 5'-CCAGGACGACGATGACAAGA-3' (SEQ ID NO: 41) and Flag-SOCS1 anti-sense primer, 5'-TCAGGGGTCCCCAATAGAAG-3' (SEQ ID NO: 42); MBP/IFN-γ sense primer, 5'-ATGAGGAAGAGCTGCAAAGC-3' (SEQ ID NO: 43), and MBP/IFN-γ anti-sense primer, 5-GGTGACAGACTCCAAGCACA-3' (SEQ ID NO: 44); GFAP/tTA sense primer, 5'-TCGCTTTCCTCTGAACGCTTCTCG-3' (SEQ ID NO: 45) and GFAP/tTA anti-sense primer, 5'-TCTGAACGCTGTGACTTGGAGTGTCC-3' (SEQ ID NO: 46); TRE/IFN-γ sense primer 5'-CGAATTCGAGCTCGGTACCC-3' (SEQ ID NO: 47) and TRE/IFN-γ anti-sense primer 5'-CCATCCTTTGCCATTCCTCCAG-3' (SEQ ID NO: 48) (Integrated DNA Technologies Inc.).

e) Northern Blot Analyses and Quantitative PCR Methods

Total RNA was isolated from the examined animals with TRIzol reagent (Invitrogen Corp., Carlsbad, Calif.). Northern blots were performed by separating 20 μg of total RNA in a 1.2% denaturing agarose gel. The samples were transferred to a nylon membrane and hybridized overnight with a SOCS1 probe that had been randomly labeled by PCR (GenAmp2400; Perkin-Elmer, Welleslay, Mass.) with [γ-$^{32}$P] dCTP and [γ-$^{32}$P] dATP (New England Nuclear/Perkin-Elmer, Welleslay, Mass.). Kodak film was exposed to the hybridized membrane at −80° C. for 48 hrs and was developed using the M7B Kodak processor (Kodak, Rochester, N.Y.). To evaluate the relative levels of total RNA present in each lane the membrane was stripped and hybridized with a radiolabeled probe specific for the 28S ribosomal RNA (Baerwald et al., 1998).

Quantitative (Q-PCR, or real-time PCR) was performed by first reverse transcribing 1 μg of DNAaseI-treated (Invitrogen) total RNA using oligo(dT)$_{12-18}$ and SuperScript II reverse transcriptase (Invitrogen RT-PCR kit). Q-PCR was performed using 20 ng of the cDNA in a reaction containing iQSupermix and the following primers and probes for Flag-SOCS1 and IFN-γ. Flag-SOCS1 sense primer, 5'-GATGACAAGACGCGCCAGATG-3' (SEQ ID NO: 49), Flag-SOCS1 anti-sense primer, 5'-GAGGACGAGGAGGGCTCTGA-3' (SEQ ID NO: 50), and Flag-SOCS1 probe, 5'-56FAM-CGCACCCAGCTGGCAGCCGACATT-3BHQ-1/-3' (SEQ ID NO: 51); IFN-γ sense primer, 5'-GATATCTCGAGGAACTGGCAAAA-3' (SEQ ID NO: 52), IFN-γ anti-sense primer 5'-CTACAAAGAGTCTGAGGTAGAAAGAGATAAT-3' (SEQ ID NO: 53), and IFN-γ probe 5'-FAM-TGGTGACATGAAAATCCTGCAGAGCCA-BHQ1-3' (SEQ ID NO: 54); GAPDH sense primer 5'-CTCAACTACATGGTCTACATGTTCCA-3' (SEQ ID NO: 55); GAPDH anti-sense primer 5'-CCATTCTCGGCCTTGACTGT-3' (SEQ ID NO: 56), and GAPDH probe, 5'-5TxRd-XN/TGACTCCACTCACGGCAAAT-TCAACG-3BHQ-2-3' (SEQ ID NO: 57) (Integrated DNA Technologies, Inc.). The reactions were performed using a BioRad I-cycler Real-Time PCR unit, under the following conditions: 1 cycle at 95° C. for 3 min, 40 cycles at 95° C. for 30 s and 60° C. for 30 s (Bio-Rad Laboratories). The mRNA levels of Flag-SOCS1 and IFN-γ were normalized to the expression levels of GAPDH based on threshold cycles (Flag-SOCS1/GAPDH and IFN-γ/GAPDH ratios) (Lin et al., 2005).

f) Western Blot Analyses and Immunoprecipitation Methods

Total lysates from brain and spleen of several PLP/SOCS1 mice and wild-type mice were obtained by tissue homogenization in RIPA buffer (Santa Cruz Biotechnology, Santa Cruz, Calif.). After incubation on ice for 15 min, lysates were centrifuged at 14,000 rpm for 30 min and the supernatants collected. Protein samples (50 μg) were electrophoresed on 15% SDS-polyacrylamide gels, transferred to PVDF membranes (Trans-blot SD apparatus, Bio-Rad Laboratories), incubated overnight with mouse anti-Flag antibody (M2, diluted to 1:1000) (Sigma-Aldrich, St. Louis, Mo.), and detected with ECL Western blot detection reagents (Amersham Biosciences, Piscataway, N.J.). Flag protein (Sigma-Aldrich), a polymer of the Flag oligopeptide, was used as a positive control for the reaction.

Immunoprecipitation was performed with an immunoprecipitation kit (Roche Molecular Biochemicals, Indianapolis, Ind.) by incubating the protein extracts from the brain and spleen of PLP/SOCS1 and wild-type mice with anti-Flag antibody (M2) for 4 hrs at 4 C, followed by overnight incubation with protein A/C agarose at 4° C. The immune complexes were collected by centrifugation at 14,000 rpm for 20S and the protein was separated from protein A/C agarose with kit-supplied reagents. Western blot of the immunoprecipitated protein was performed as described above.

g) Immunohistochemistry

Animals were anesthetized with 0.01 ml/g of 2.5% Avertin (Sigma-Aldrich) administered intraperitoneally and perfused with saline followed by 2% paraformaldehyde for 10 min. Brains were removed, postfixed for 1 hr with 2% paraformaldehyde, cryopreserved with 30% sucrose for 48 h, prepared as frozen blocks (OCT compound, Sacura, Torrance, Calif.), and sectioned at a thickness of 7 μm at −20° C. (Leica CM1800 cryostat, Leica Microsystems). Prior to immunostaining, the sections were treated with 0.1% Triton X-100 (Sigma-Aldrich) for 10 min and incubated with 10% bovine serum albumin (Sigma-Aldrich) or goat serum (Invitrogen) for 30 min. Indirect immunostaining was performed by sequential incubation with primary antibodies (for 2 h at room temperature or overnight at 4° C.) and FITC-conjugated or Cy3-congugated secondary antibodies (for 30 min). All of the following primary and secondary antibodies used in the study were commercially available: mouse and rabbit anti- Flag antibody (dilution, 1:100; Sigma-Aldrich), mouse anti-CC1 antibody (dilution, 1:20; Oncogene), mouse MHC class I antibody (dilution, 1:100; Chemicon International, Temecula, Calif.), mouse anti-PLP, proteolipid protein, antibody (dilution, 1:100; Chemicon International), mouse and rabbit anti-SOCS1 antibody (dilution, 1:100; Santa Cruz Biotechnology, Santa Cruz, Calif.), rabbit anti-Stat1 antibody (dilution, 1:100; Santa Cruz Biotecnology), anti-mouse or anti-rabbit FITC-conjugated secondary antibody (dilution, 1:100; Jackson Immunoresearch, Bar Harbor, Me.), and anti-mouse or anti-rabbit Cy3-congugated antibody (dilution, 1:500; Jackson Immunoresearch). The immunostained sections were mounted using Vectorshield mounting medium containing DAPI nuclear stain (Vector Laboratories, Burlingame, Calif.) and examined using a fluorescent microscope (Axoplan; Carl Zeiss Microimaging).

Oligodendrocyte cell density was assessed digitally using Axiovision software, at postnatal day 21, as previously described (Lin et al., 2005). The brains were sectioned sagittally through the corpus callosum dividing the brain in two symmetrical halves. Ten frozen sections from each half were prepared at 7 μm thickness, and numbered in the sequence of their preparation. The brains of three animals per study group were prepared in this fashion. Following the CC1 immunostaining the corresponding area of corpus callosum of each section was digitally selected and the corresponding total area obtained. CC1 cell counting was performed manually within the selected areas of each section, and the number of CC1 positive cells per square area ($mm^2$) calculated. The results were presented as mean±SD of CC1 (+) cells/$mm^2$ with n=3 animals per study group.

h) Electron Microscopy

Mice selected for electron microscopy studies were perfused with 4% paraformaladehyde and 2.5% glutaraldehyde. Brains were harvested, and white matter structures were sectioned using a stereotype microscope (Wild M3C; Wild AG, Heebrugg, Switzerland). The tissue was further postfixed in osmium tetroxide and embedded in freshly prepared Epoxy resin (Epon-812; Electron Microscope Sciences, Fort Washington, Pa.) for 48 hrs at 60° C. The resin blocks were sectioned at 90 nm using Leica Ultracut ultramicrotome (Leica Microsystems) and stained with 5% uracyl acetate and 2.5% lead citrate. Utrastructure of the tissue samples was examined using the Tecnai-F30 transmission electron microscope (FEI Company, Hillsboro, Oreg.).

Myelination patterns of the examined animals were assessed at postnatal day 21 by calculating the percent unmyelinated axons and ratio of the axon/fiber diameters (G ratio) with Image J software (National Institutes of Health, Bethesda, Md.) as previously described (Lin at al., 2005). The brains were sectioned sagittally through the corpus callosum dividing the brain in two symmetrical halves. Approximately 2 $mm^3$ samples from the genu and the splenum of both halves of corpus callosum were obtained using a Wild M3C stereotype microscope. The orientation of the specimen in the resin blocks yielding axonal cross sections (well seen myelin rings) was chosen, and established by toluedine blue staining of a few sample sections. The resin blocks with the chosen orientation were processed for electron microscope examination. Randomly selected areas were examined and ten representative pictures from both genu and splenum corpus callosum were obtained at 12000× magnification. The number of unmyelinated axons was assessed by manual counting of axons that lacked myelin and were encircled solely by their own plasma membrane. All unmyelinated axons present in the representative images were counted, and their percentage calculated by examining a total of five hundred axons per tissue sample. The G ratio (axonal diameter/fiber diameter ratio) of myelinated axons was assessed by digitally selecting the area encircled by the inner and outer surfaces of the myelin sheath, obtaining the axonal (inner) and the fiber (outer) diameters, and dividing their corresponding values (axonal diameter/fiber diameter ratio). The brains of three animals per group were examined, and the G ratios of a total of 150 nerve fibers from both genu and splenum were examined. The results were presented as mean±SD of G ratio and percent unmyelinataed axons with n=3 animals per study group.

i) Mixed Primary Oligodendrocytes Cultures and STAT1 Translocation Assay

Mixed primary oligodendrocyte cultures were prepared as previously described (Baerwald et al., 2000). Briefly, brain tissue was harvested from 2-3-day-old newborn pups of PLP/SOCS1 and C57Bl/6J matings. Because the litters contained transgenic and wild-type pups, the brain of each animal was processed individually, cultured separately, and later genotype matched. Each brain was digested separately using 0.25% trypsin and 10 μg/ml of DNAaseI (Invitrogen) in Dulbecco's modified Eagle's medium (DMEM) for 20 min at 37° C., and cells were cultured on separate poly-D-lysine-coated 75-$mm^2$ flasks (Sigma-Aldrich). The cultures were maintained with 10% fetal bovine serum DMEM at 37° C. with 5% $CO_2$ for 12 days, and then switched to a defined medium containing 5 μl/ml of insulin, 50 μg/ml of transferrin, 30 nM of selenium, 10 nM of biotin, 10 nM of progesterone, 15 nM of T3, 0.1% bovine serum albumin, and 1% ampicillin-streptomycin (Sigma-Aldrich). On the fifth day of differentiation, the cultures were treated with 100 U/mL of IFN-γ (Calbiochem, San Diego, Calif.) for 30 min. Dual immunostaining for anti-PLP and anti-Stat1 antibodies, and DAPI nuclear staining were performed as described above. The Stat1 nuclear translocation assay was performed in six separate culture preparations. One hundred PLP positive cells were manually counted in both wild-type and PLP/SOCS1 cultures. The results were presented as mean±SD percent cells positive for Stat1 nuclear translocation.

j) Statistical Analysis

All data were generated from three independent experiments. Means, standard deviations, and p-values were calculated using Average, Stdev, and Anova in Microsoft Excel (Microsoft, Redmond, Wash.). A statistically significant difference was defined as a p-value of <0.05.

2. Characterization of the PLP/SOCS1 Transgenic Mouse Line

The PLP/SOCS1 transgenic mice, which were generated as described in Example 25, were designed to express Flag epitope-tagged SOCS1 in myelinating cells (FIG. 30A). These mice exhibit no phenotypic abnormalities, breed and produce transgenic progeny in a Mendelian fashion, and live a normal life span. Histological evaluation, including electron microscopy, performed at different time points up to 1 year of age revealed no significant differences in the myelination patterns or the number, density, or morphology of oligodendrocytes (see below) between transgenic and wild-type littermates.

Expression of the PLP/SOCS1 transgene was characterized at postnatal day 21 using several methods. Northern blot analysis with a SOCS1 cDNA hybridization probe revealed a band of increased intensity in RNA samples from the brains of transgenic mice relative to control brain samples but not from other tissues (FIG. 30B). Real-time PCR analysis with transgene-specific primers revealed the highest concentrations of transgene-derived SOCS1 mRNA in brain, spinal cord, and sciatic nerve, with significantly lower levels in other organs including heart, thymus, spleen, and liver (FIG. 30C). Transgene expression appeared to be stable up to 12 months of age (data not shown).

Western blot analysis, using an antibody to the Flag tag, revealed a 19-kD band corresponding to the expected size of SOCS1 in the PLP/SOCS1 brain lysates, but not in wild-type brain lysates or PLP/SOCS1 spleen lysates (FIG. 30D). To further confirm Flag-SOCS1 protein expression, we performed immunoprecipitation with the anti-Flag antibody, which again detected a 19-kD positive band in the PLP/SOCS1 brain immunoprecipitates, but not in the wild-type brain or PLP/SOCS1 spleen immunoprecipitates (FIG. 30E).

Indirect immunostaining of wild-type and PLP/SOCS1 brains with both anti-SOCS 1 and anti-Flag antibodies also demonstrated expression of the transgene (FIG. 30F-I). We detected both anti-Flag and anti-SOCS1 immunopositivity only in PLP/SOCS1 brains.

Figure 31:
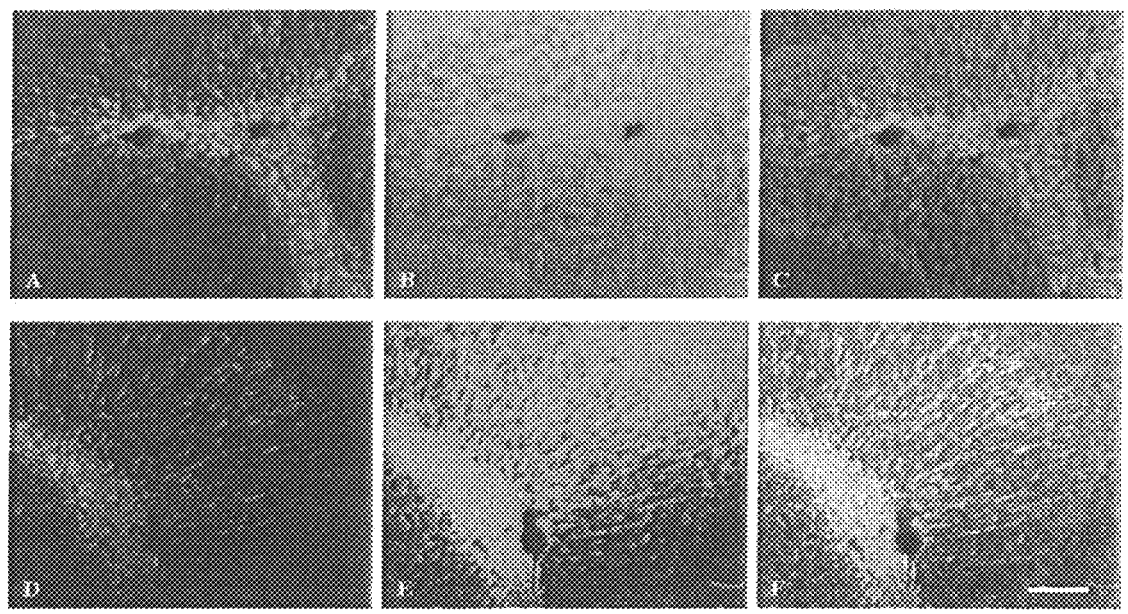
FIG. 31 shows the colocalization of Flag-SOCS1 and PLP in vivo. Dual immunostaining of wild-type (A-C, top row) and PLP/SOCS1 (D-F, bottom row) cerebellar tissue, harvested at postnatal day 21, was performed using anti-PLP/Cy3 (A, D, red) and anti-Flag/FITC (B, E, green) antibodies, and DAPI nuclear stain (C, F, blue). PLP positive structures of the wild-type samples (A, red) demonstrated no immunopositivity for anti-Flag (B) and no signal colocalization was established (C). In contrast, PLP positive structures of PLP/SOCS1 samples (D) expressed Flag-SOCS1 (E), and strong co-localization between the anti-PLP and anti-Flag immunopositivity was detected (F, yellow color signifies co-localization). Sagittal sections of cerebellum; Bar=20 µm.

To localize the expression of Flag-SOCS1 in the CNS, we performed dual immunostaining of wild-type and PLP/SOCS1 brain tissue with the anti-Flag antibody and either anti-PLP antibody, a marker for myelin, or anti-CC1 antibody, a marker for the oligodendrocyte cell body. A strong colocalization between anti-PLP and anti-Flag antibodies, as well as between anti-CC1 and anti-Flag antibodies (data not shown) was found, suggesting that Flag-SOCS1 was localized to the white matter and oligodendrocytes (FIG. 31). Non-colocalizing immunopositivity for anti-Flag, anti-PLP or anti-CC1 antibodies was not detected.

Figure 32:
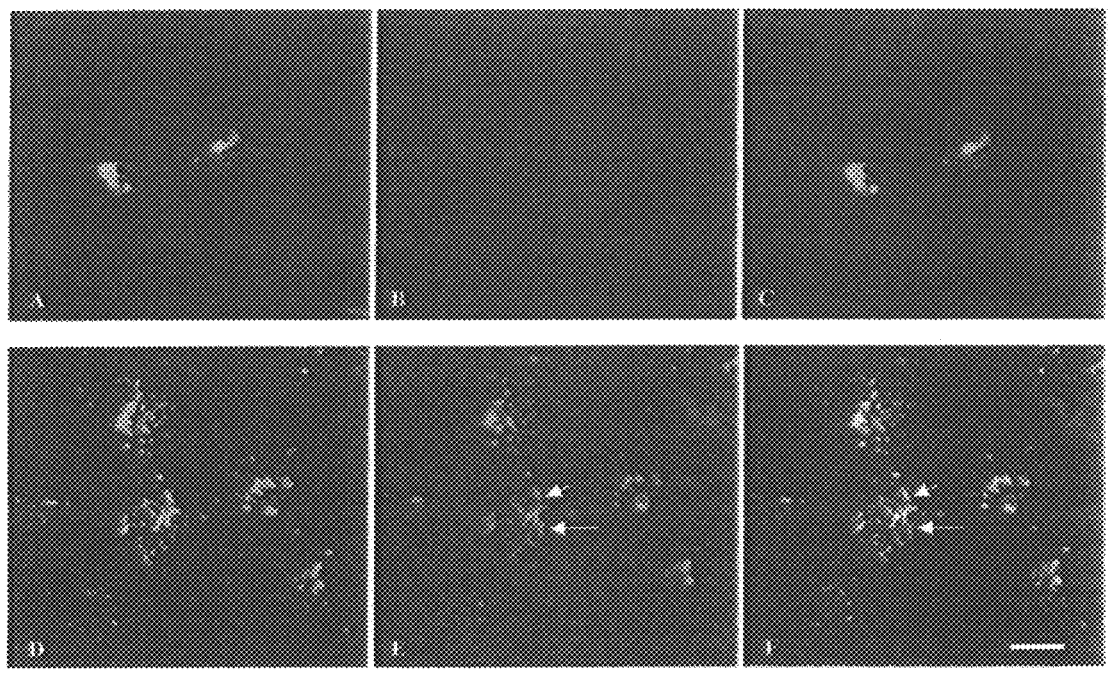
FIG. 32 shows the Colocalization of flag-SOCS1 and PLP in vitro. Dual immunostaining of wild-type (A-C, top row) and PLP/SOCS1 (D-F, bottom row) mixed primary oligodendrocyte cultures was performed using anti-PLP/FITC (A, D, green) and anti-Flag/Cy3 (B, E, red) antibodies. PLP positive oligodendrocytes in the wild-type culture (A) demonstrated no immunopositivity for anti-Flag (B), and no signal colocalization was established (C). In contrast, PLP positive oligodendrocytes (D) in the PLP/SOCS1 cultures expressed Flag-SOCS1 (E), and strong colocalization between anti-PLP and anti-Flag signals was detected (F). Flag-SOCS1 appeared to be localized in the cell body (large arrows) and cell processes (small arrows) of oligodendrocytes. Bar=20 µm.

The expression of Flag-SOCS1 in primary mixed oligodendrocyte cultures established from transgenic animals by dual immunostaining with anti-PLP and anti-Flag antibodies was also detected (FIG. 32). Expression of Flag-SOCS1 was detected only in cultures from PLP/SOCS1 animals and only in cells expressing PLP. Virtually all PLP-positive cells were also positive for Flag-SOCS1. The colocalization between anti-Flag and anti-PLP immunoreactivity appeared to involve both the cell body and cell processes (FIG. 32F).

3. Oligodendrocytes from PLP/SOCS1 Mice Exhibit Diminished Responsiveness to INF-γ

Figure 33:
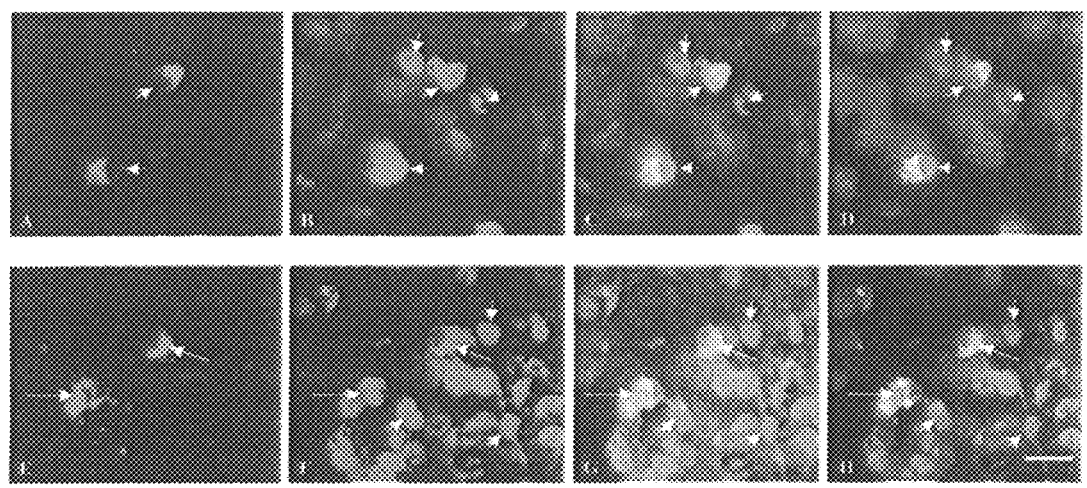
FIG. 33 shows the differential inhibition of Stat1 nuclear translocation. Mixed primary oligodendrocyte cultures from wild-type (A-D; top row) and PLP/SOCS1 (E-H; bottom row) mice were stimulated with 100 U IFN-γ for 30 min, and dual immunostainings using anti-PLP/Cy3 (A, E; red), anti-Stat1 (B, F; green), and DAPI nuclear stain (D, H; blue) were performed and the fluorescent signals digitally overlayed (C and G, overlay between PLP/Cy3 and Stat1/FITC signals; D and H, overlay between PLP/Cy3, Stat1/FITC and DAPI signals). In the wild-type cultures, Stat1 was colocalized with DAPI stained nuclei of all cells, including the PLP positive oligodendrocytes (small arrows) (B, D, colocalization between Stat 1 and DAPI). In the PLP/SOCS1 cultures, Stat1 was colocalized with DAPI positive nuclei of the PLP negative cells (small arrows), but not of the PLP positive oligodendrocytes (large arrows) (F, H). Stat1 in the PLP positive oligodendrocytes did not colocalize with DAPI stained nuclei, but remained in the cytoplasm (large arrows) (F, H). Bar=10 µm.

The responsiveness of PLP/SOCS1 oligodendrocytes to IFN-γ was studied in primary mixed glial cultures. To determine whether expression of transgenic SOCS1 would interfere with the nuclear translocation of the IFN-γ-signaling molecule Stat1, the cell cultures were treated with 100 U/mL of IFN-γ for 30 min and immunostained using anti-PLP and anti-Stat1 antibodies along with the DAPI nuclear stain (FIG. 33). Examination of Stat1 subcellular localization in wild-type cultures revealed strong colocalization with DAPI-positive nuclei in all cells, including PLP-positive oligodendrocytes. In contrast, subcellular localization of Stat1 in PLP/SOCS1 cultures revealed a differential response to IFN-γ. In transgenic PLP-positive oligodendrocytes, Stat1 remained in the cytoplasm and did not colocalize with cell nuclei in the presence of IFN-γ, (FIG. 33E-H). This was in contrast to the response of the surrounding PLP-negative cells, which, similarly to wild-type cells, responded to IFN-γ with Stat1 nuclear translocation. Virtually all PLP positive oligodendrocytes (96±3 cells) in the wild-type cultures responded to IFN-γ stimulation with Stat1 nuclear translocation. In contrast, Stat1 nuclear translocation was detected only in occasional PLP positive oligodendrocytes (6±2 cells) following IFN-γ stimulation (p<0.05).

Figure 34:
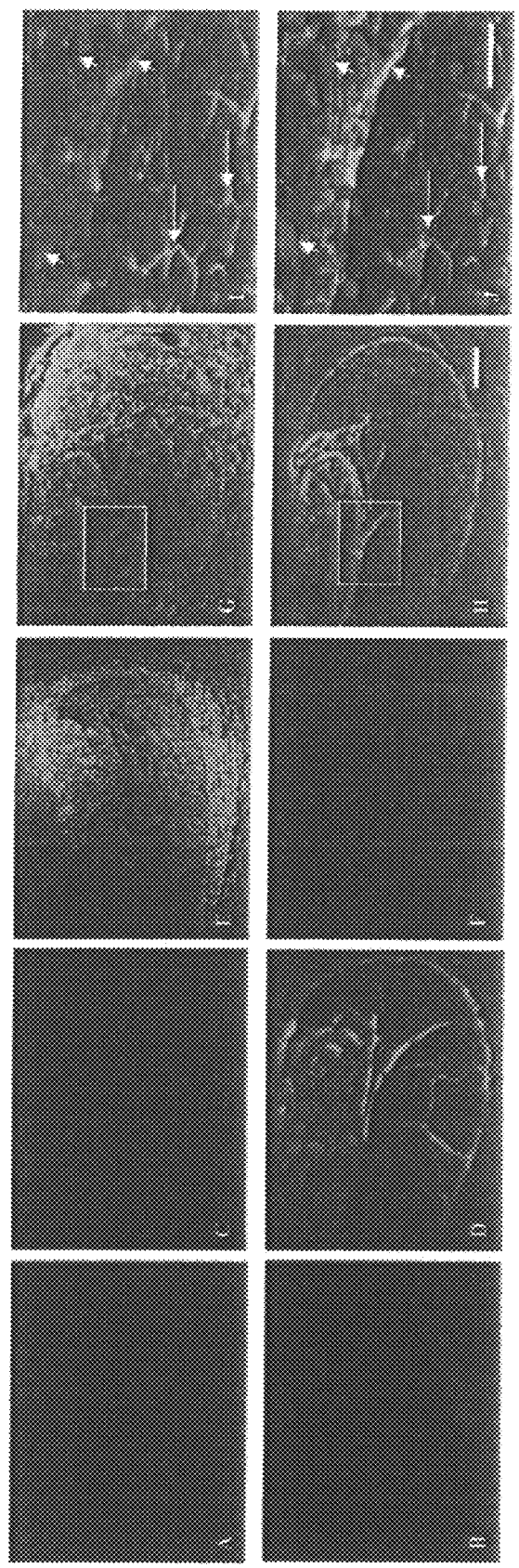
FIG. 34 shows the differential expression of MHC class I molecule in MBP/IFN-γ×PLP/SOCS1 mice. Wild-type (A, B), PLP/SOCS1 (C, D), MBP/IFN-γ (E, F) and MBP/IFN-γ× PLP/SOCS1 (G, H, I, J) mouse brains, harvested at postnatal day 21, were dual immunostained with anti-MHC class I/FITC (A, C, E, G, I; green) and anti-flag/Cy3 (B, D, F, H, J; red) antibodies, and DAPI nuclear stain (J, blue). Wild-type samples were double negative (A, B). PLP/SOCS1 samples were negative for MHC class I molecule (C) and positive for Flag (D). MBP/IFN-γ samples were single positive for MHC class I molecule (E) and negative for Flag (F). Double transgenic MBP/IFN-γ×PLP/SOCS1 samples were double positive for MHC class I molecule (G) and Flag (H). Higher magnification of MBP/IFN-γ×PLP/SOCS1 samples (outlined square in G, H) revealed differential distribution of the immunopositivity (I, J); MHC class I positive cells (large arrows) were negative for Flag, whereas Flag positive cells (small arrows) were negative for MHC class I molecules. Sagittal sections of corpus callosum; Bar=20 µm (A-H); Bar=10 µm (I, J).

We next characterized the responsiveness of PLP/SOCS1 oligodendrocytes to IFN-γ in vivo using the induction of major histocompatibilty complex class I (MHC class I) molecule expression as an indication of IFN-γ sensitivity. The capacity of SOCS1 to inhibit IFN-γ-mediated induction of MHC class I molecule was examined in a double-transgenic system. MBP/IFN-γ (line 172) single-transgenic mice, which express a low level of IFN-γ in the CNS (Gao et al., 2000), were mated to PLP/SOCS1 mice, and the single and double transgenic progeny were examined for differences in MHC class I molecule expression (FIG. 34). MHC class I molecule expression was neither detectable in control wild-type mice nor PLP/SOCS1 mice (FIG. 34A-D). Consistent with previous reports, MBP/IFN-γ mice exhibited upregulated expression of the MHC class I molecule, with diffuse protein localization along the myelin sheath (FIG. 34E, F) (Corbin et al., 1996). The double-transgenic mice (MBP/IFN-γ×PLP/SOCS1), however, displayed a differential pattern of MHC class I molecule expression (FIG. 34G-J). As shown in FIG. 34, oligodendrocytes and myelin positive for Flag-tagged SOCS1 did not express detectable levels of MHC class I molecule, whereas, cells negative for transgene expression, and in close proximity to the SOCS1-positive cells, demonstrated strong immunoreactivity (FIG. 34G-J). Similar differential upregulation of MHC class I molecule expression was observed following the direct administration of IFN-γ in the brain of PLP/SOCS1 mice (data not shown). Together, these data indicate that oligodendrocytes from PLP/SOCS1 mice display diminished responsiveness to IFN-γ.

4. PLP/SOCS1 Mice are Protected Against Injurious Effects of INF-γ During Development Transgenic expression of IFN-γ in the CNS of developing mice results in oligodendrocyte loss and hypomyelination (Corbin et al., 1996; Lin et al 2005). To determine whether SOCS1 expression could protect developing oligodendrocytes from the injurious effects of IFN-γ, we crossed PLP/SOCS1 mice to three transgenic mouse lines overexpressing IFN-γ in the CNS at different levels: MBP/IFN-γ (line 172), GFAP/tTA×TRE/IFN-γ (lines 184/110) and GFAP/tTA×TRE/IFN-γ (lines 184/67) and the following three mating systems were established (detailed in the Material and Methods): MBP/IFN-γ×PLP/SOCS1 (172×PLP/SOCS1, a double transgenic system) and GFAP/tTA×TRE/IFN-γ×PLP/SOCS1 (184/110×PLP/SOCS1 and 184/67×PLP/SOCS1, two triple-transgenic systems). The litter (F1 generation) of each mating system was divided into four study groups depending on their genotype: wild-type/single transgenic controls, mice expressing SOCS 1 only, mice expressing IFN-γ only, and mice expressing both IFN-γ and SOCS1. A total of 40 animals per mating system (10 animals per each study group) were collected and examined clinically and histologically at postnatal day 21.

Phenotypic comparisons of littermates were performed from birth to postnatal day 21 and evaluation consisted of behavioral observation and challenged ladder walking to elicit tremor. MBP/IFN-γ (line 172) mice express low levels of IFN-γ in the CNS and displayed no behavioral abnormalities, in accordance with findings reported elsewhere (Corbin et al., 1996). Mice from the F1 generation of the MBP/IFN-γ×PLP/SOCS1 (172×PLP/SOCS1) mating system similarly displayed no behavioral abnormalities regardless of genotype. Double-transgenic GFAP/tTA×TRE/IFN-γ (lines 184/110) and GFAP/tTA×TRE/IFN-γ (lines 184/67) mice display mild to moderate tremor that appears during the second postnatal week and peaks by 21 days of age (Lin et al., 2004; 2005). Mice from the F1 generation of the GFAP/tTA×TRE/IFN-γ×PLP/SOCS1 mating systems exhibited tremor, the incidence of which was dependent on genotype (Table 2).

TABLE 2

Incidence of tremor among the transgenic littermates

|  | Wild-type/ controls | SOCS1 | IFN-γ | IFN-γ × SOCS1 |
| --- | --- | --- | --- | --- |
| 172 × PLP/SOCS1 | 0% | 0% | 0% | 0% |
| 184/110 × PLP/SOCS1 | 0% | 0% | 80% (8/10) | 10% (1/10) |
| 184/67 × PLP/SOCS1 | 0% | 0% | 100% (10/10) | 30% (3/10) |

Littermates from three transgenic mating systems, 172× PLP/SOCS1, 184/110×PLP/SOCS1 and 184/67×PLP/SOCS1 were stratified according to their genotype into four groups: Wild-type/control mice, mice expressing SOCS1 only, mice expressing IFN-γ only, and mice expressing both IFN-γ and SOCS1. Ten mice per group were clinically followed during the first three postnatal weeks and the incidence of tremor recorded.

The phenotypes of wild-type mice and single-transgenic control mice (GFAP/tTA [184], TRE/IFN-γ [67 and 110]), and PLP/SOCS1 mice were clinically normal. The tremoring phenotype, which varied in severity, was identified in almost all double-transgenic GFAP/tTA×TRE/IFN-γ mice overexpressing IFN-γ: 80% (8/10) of 184/110 mice and 100% (10/10) of 184/67 mice. Triple-transgenic GFAP/tTA×TRE/IFN-γ×PLP/SOCS1 mice overexpressing both IFN-γ and SOCS 1 appeared to be protected, because only 10% (1/10) of 184/110×PLP/SOCS1 mice, and 30% (3/10) of 184/67×PLP/SOCS1 mice developed tremor (Table 2).

Figure 35:
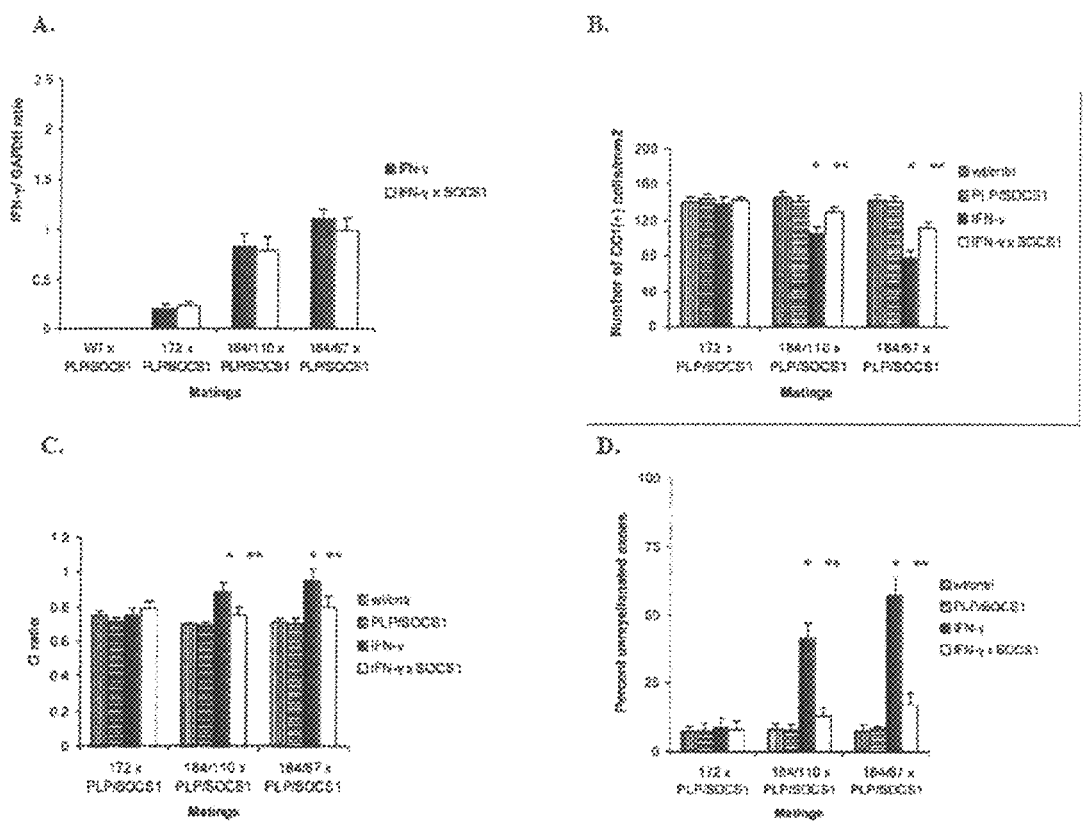
FIG. 35 shows the SOCS1-mediated protection of oligodendrocytes and myelin. The IFN-γ expression (A), oligodendrocyte density (CC1 cells/mm$^2$) (B), G ratio (C), and percent unmyelinated axons (D) were examined among littermates of three transgenic systems: 172×PLP/SOCS1, 184/110×PLP/SOCS1 and 184/67×PLP/SOCS1 at postnatal day 21 (see Results for complete description). The relative amount of IFN-γ expression differed among the systems but no statistical difference was found in the levels of expression between littermates from the same transgenic system overexpressing either IFN-γ only (IFN-γ) or both IFN-γ and SOCS1 (IFN-γ× SOCS1) (A). The IFN-γ overexpressing littermates (IFN-γ) displayed significant dose-dependent oligodendrocyte cell loss (B) and hypomyelination (C, D) as compared to the wild type, single transgenic control (wt/cntrl) and PLP/SOCS1 littermates (*p<0.05, n=3 animals per study group). The triple transgenic littermates expressing both IFN-γ and SOCS1 (IFN-γ×SOCS1) displayed significant oligodendrocyte (B) and myelin preservation (C, D) as compared to those overexpressing IFN-γ only (IFN-γ) (**p<0.05, n=3 animals per study group).

The clinically examined littermates of all three transgenic mating systems were further evaluated for histological abnormalities at postnatal day 21. Three animals per study group from each mating system were examined histologically for oligodendrocyte and myelin abnormalities. Brain tissue was obtained from each animal at the time of sacrifice (prior to the fixating perfusion) and total RNA isolated. The possibility that SOCS1 expression affected the expression of the IFN-γ transgene was examined in all three transgenic mating systems using quantitative PCR (Q-PCR) (FIG. 35A). IFN-γ expression was detected in MBP/IFN-γ single-transgenic and MBP/IFN-γ×PLP/SOCS1 double-transgenic littermates of the 172×PLP/SOCS1 transgenic system, in GFAP/tTA×TRE/IFN-γ double-transgenic and GFAP/tTA×TRE/IFN-γ×PLP/SOCS1 triple-transgenic littermates of the 184/110×PLP/SOCS transgenic system, and in GFAP/tTA×TRE/IFN-γ double-transgenic and GFAP/tTA×TRE/IFN-γ×PLP/SOCS1 triple-transgenic littermates of the 184/67×PLP/SOC1 transgenic system. Two characteristics of IFN-γ expression were observed. First, the three mating systems differed in their expression levels; MBP/IFN-γ×PLP/SOCS1 (172×PLP/SOCS1) expressed the lowest, and GFAP/tTA×TRE/IFN-γ×PLP/SOCS1 (184/67×PLP/SOC1) expressed the highest IFN-γ levels. Secondly, the littermates of the same mating system, expressing IFN-γ only or both IFN-γ and SOCS1, did not differ in their expression levels. No detectible levels of IFN-γ were found in the wild-type, the GFAP/tTA and TRE/IFN-γ single-transgenic, and the PLP/SOCS1 littermates (FIG. 35A).

Figure 36:
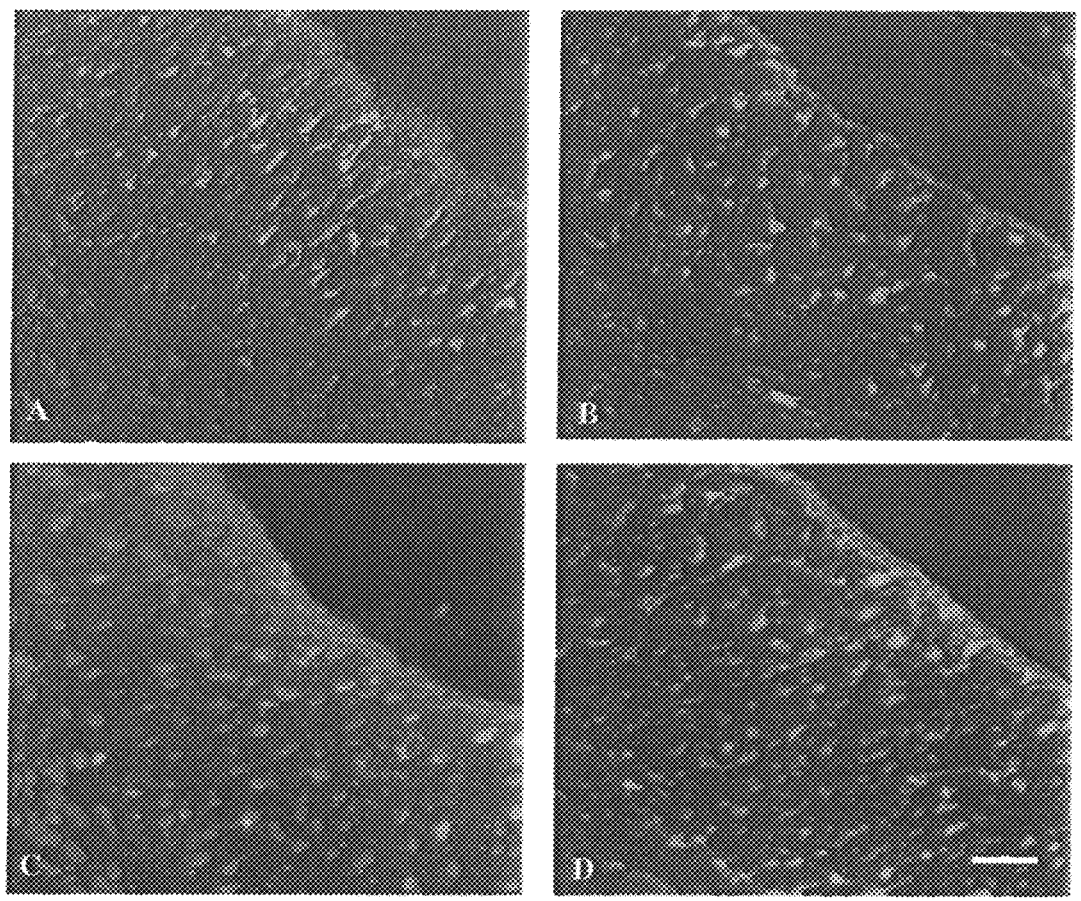
FIG. 36 shows SOCS1-mediated oligodendrocyte protection. Representative images of the quanitated areas from GFAP/tTA×TRE/IFN-γ×PLP/SOCS1 (184/67×PLP/SOCS1) mice at postnatal day 21: A. Wild-type; B. PLP/SOCS1; C. 184/67 and D; 184/67×PLP/SOCS1. Immmunostaining with CC1/Cy3 (red) and DAPI nuclear stain (blue). Sagittal sections of corpus callosum; Bar=20 μm. Note the loss of CC1 positivity in the sample from an IFN-γ-overexpressing mouse (C) compared to the samples from wild-type (A) and PLP/SOCS1 mice (B), and the significant oligodendrocyte preservation in the sample from a mouse overexpressing both IFN-γ and SOCS1 (D).

The cerebra of three animals per study group from all transgenic mating systems were processed for immunohistochemical analysis with the CC1 antibody to determine oligodendrocyte density (FIG. 35B and FIG. 33). The MBP/IFN-γ mice expressed the lowest levels of IFN-γ in the CNS compared to GFAP/tTA×TRE/IFN-γ mice, and displayed no significant abnormalities in CC1-positive cell density, in accordance with results reported previously (Gao et al., 2000). We found no statistically significant difference in the oligodendrocyte density among mice from the F1 generation of the MBP/IFN-γ×PLP/SOCS1 (172×PLP/SOCS1) mating system. In the triple-transgenic systems (GFAP/tTA×TRE/IFN-γ×PLP/SOCS1), we found that the oligodendrocyte density in mice from the F1 generation differed depending on genotype (FIG. 35B and FIG. 36). Wild-type mice and the single-transgenic mice (PLP/SOCS1, GFAP/tTA, and TRE/IFN-γ) had comparable oligodendrocyte densities. We found severe dose-dependent oligodendocyte loss in the GFAP/tTA×TRE/IFN-γ mice overexpressing IFN-γ, compared with the wild-type and single-transgenic littermates: approximately 20% of oligodendrocytes were lost in 184/110 mice (from 146±6 CC1 (+) cells/mm$^2$ in the wild-type mice to 115±8 CC1 (+) cells/mm$^2$ in the IFN-γ mice), and approximately 40% were lost in 184/67 mice (from 144±5 CC1 (+) cells/mm$^2$ in the wild-type mice to 79±9 CC1 (+) cells/mm$^2$ in the IFN-γ overexpressing mice). In contrast, GFAP/tTA×TRE/IFN-γ×PLP/SOCS1 triple-transgenic littermates that overexpressed both IFN-γ and SOCS1 lost statistically significantly fewer oligodendrocytes compared with mice overexpressing IFN-γ only: approximately 8% of oligodendrocytes were lost in 184/110×PLP/SOCS1 mice (from 141±6 CC1 (+) cells/mm$^2$ in the PLP/SOCS1 mice to 129±6 CC1 (+) cells/mm$^2$ in the IFN-γ and SOCS1 overexpressing mice), and approximately 15% were lost hi 184/67×PLP/SOCS1 mice (from 142±5 CC1 (+) cells/mm$^2$ in the PLP/SOCS1 mice to 112±7 CC1 (+) cells/mm$^2$ in the IFN-γ and SOCS1 overexpressing mice) (FIG. 35B and FIG. 36).

Figure 37:
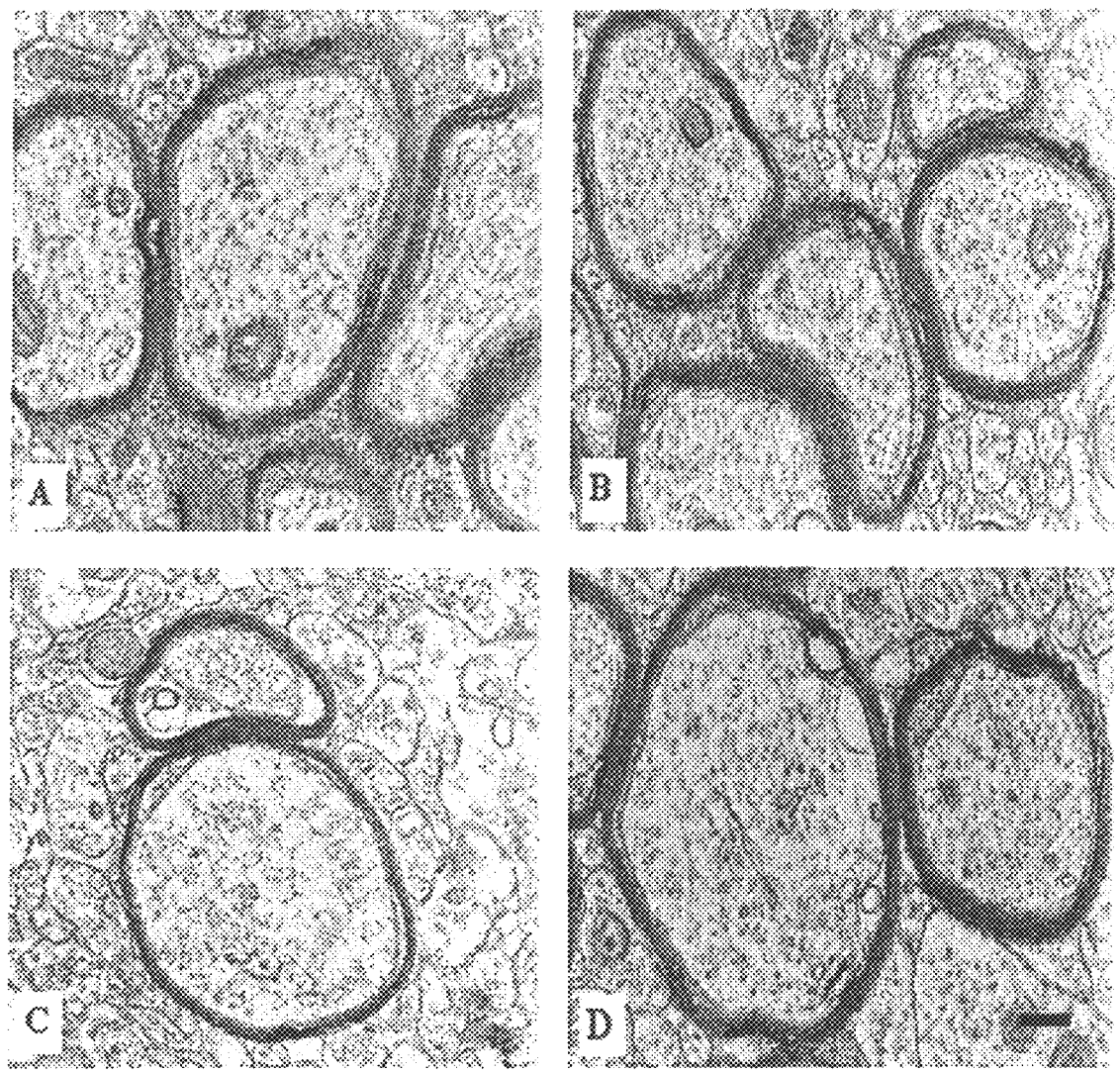
FIG. 37 shows SOCS1-mediated myelin protection. Representative images of the quanitated areas from GFAP/tTA× TRE/IFN-γ×PLP/SOCS1 (184/67×PLP/SOCS1) mice at postnatal day 21: A. Wild-type; B. PLP/SOCS1; C. 184/67 and D; 184/167×PLP/SOCS1. Electron micrographs of corpus callosum; Bar=500 nm. Note the hypomyelination in the sample from an IFN-γ-overexpressing mouse (C) compared to the samples from wild type (A) and PLP/SOCS1 mice (B), and the significant myelin preservation in the sample from a mouse overexpressing both IFN-γ and SOCS1 (D).

Myelination patterns in the harvested cerebra were further evaluated with electron microscopy, and the level of myelination was assessed by calculating the G ratio (axon diameter/fiber diameter ratio) and the percentage of unmyelinating axons (FIGS. 35C and D, and FIG. 37). We found no statistically significant difference in G ratios among wild-type, the single-transgenic, and double transgenic littermates from the MBP/IFN-γ×PLP/SOCS1 (172×PLP/SOCS1) mating system. In the triple-transgenic systems (GFAP/tTA×TRE/IFN-γ×PLP/SOCS1), significant differences in G ratios were found among the F1 generation mice, depending on genotype (FIG. 35C and FIG. 36). G ratios among the wild-type and the GFAP/t TA, TRE/IFN-γ, and PLP/SOCS1 single-transgenic littermates were similar. IFN-γ-overexpressing GFAP/tTA×TRE/IFN-γ littermates displayed significantly increased G ratios indicating hypomyelination (defined as a G ratio>0.8): 0.89±0.02 for 184/110 mice and 0.95±0.04 for the 184/67 mice (FIG. 35C). In contrast, their triple-transgenic (GFAP/tTA×TRE/IFN-γ×PLP/SOCS1) littermates overexpressing both IFN-γ and SOCS1 had significantly lower G ratios: 0.75±0.03 (within the normal range) for 184/110×PLP/SOCS1 mice, and 0.82±0.08 for 184/67×PLP/SOCS1 mice (FIG. 35C and FIG. 37).

The myelin abnormalities were further quantified by determining the percentage of unmyelinated axons in the various transgenic genotypes (FIG. 35D). We found no significant difference in the percentage of unmyelinated axons (less than 9%) among the F1 generation littermates of the MBP/IFN-γ×PLP/SOCS1 (172×PLP/SOCS1) double-transgenic system, regardless of genotype (FIG. 35D). In the triple-transgenic GFAP/tTA×TRE/IFN-γ×PLP/SOCS1 systems, however, the distribution of unmyelinated axons differed depending on genotype (FIG. 35D). There was a significantly increased percentage of unmyelinated axons in IFN-γ-overexpressing GFAP/ITA×TRE/IFN-γ littermates compared to wild-type and single-transgenic control mice: 41%±6 in 184/110 mice and 57%±7 in 184/67 mice. In contrast, triple-transgenic GFAP/tTA×TRE/IFN-γ×PLP/SOCS1 overexpressing both IFN-γ and SOCS1 had a significantly lower percentage of unmyelinated axons compared with mice overexpressing IFN-γ alone: only 13%±3 for 184/110×PLP/SOCS1 mice and 17%±4.5 for 184/67×PLP/SOCS1 mice (FIG. 35D). Together, these data demonstrate that oligodendroglial expression of SOCS1 protects mice from the clinical and morphological consequences of IFN-γ expression in the CNS during development.

The presence of the T-cell-derived cytokine IFN-γ within the CNS is believed to play a critical role in the pathogenesis of immune-mediated demyelinating disorders (Panitch et al, 1987; Galbinski et al., 1999; Tran et al., 2000; Vartanian et al., 1996; Horwitz et al. 1997; Steinman, 2001). Nevertheless, the cellular target of the cytokine's effect remains unresolved. In this report we describe the generation of transgenic mice in which the oligodendrocytes display a significantly reduced capacity to respond to IFN-γ. These mice are protected from the injurious effect of ectopic expression of IFN-γ within the CNS, suggesting that a direct deleterious effect of IFN-γ on oligodendrocytes contributes to immune-mediated disease pathogenesis. As discussed below, the work described has significant clinical implications.

Transgenic animals that ectopically express IFN-γ in the CNS during postnatal development are hypomyelinated and contain reduced numbers of oligodendrocytes (Corbin et al., 1996; LeFerla et al., 2000; Lin et al., 2005). Moreover, the induction of IFN-γ expression in the CNS following demyelinating insults results in reduced oligodendroglial repopulation of the demyelinating lesions and impaired remyelination (Lin et al., in press). Previously reported data from our laboratory suggests that the presence of IFN-γ in the CNS activates an ER stress response in oligodendrocytes, which contributes to the observed pathological effects (Lin et al, 2005; in press). It is unclear, however, if the injurious effect of IFN-γ on oligdodendrocytes is a result of a direct action or whether it represents a secondary effect, possibly through microglial activation.

IFN-γ has also been shown to have harmful effects on oligodendrocytes and their progenitors in vitro. There is considerable evidence to suggest that at least part of the injurious effect of this cytokine is mediated through the activation of microglial cells. IFN-γ-treated microglia release cytotoxic agents, including nitric oxide and tumor necrosis factor alpha, which are known to be damaging to oligodendrocytes (Merrill et al., 1991, 1993, Loughlin et al., 1997). Studies using purified oligodendrocytes in vitro, however, suggest that the cytokine may have a direct, harmful effect on oligodendrocytes (Tones et al., 1995; Agresti et al., 1996; Baerwald et al., 1998; Andrews et al., 1998; Lin et al., 2005). IFN-γ has been shown to inhibit cell cycle exit of oligodendroglial progenitor cells, which may predispose these cells to apoptotic death (Chew et al., 2005). Additionally, IFN-γ has been shown to be a very powerful apoptosis-inducing agent for developing oligodendrocytes (Baerwald et al., 1998, 2000; Lin et al., 2005). Oligodendrocytes that have been allowed to differentiate in vitro to the point of expressing mature oligodendroglial markers are less sensitive to the presence of the cytokine, although they do eventually succumb to necrosis (Baerwald et al., 1998).

In an effort to differentiate direct versus indirect effects of IFN-γ on oligodendrocytes in vivo, we generated transgenic mice that exhibited diminished oligodendrocyte-specific responsiveness to IFN-γ. Transgenic mice expressing either the dominant-negative form of IFN-γ receptor subunit 1 (IFNGR1) or the suppressor of cytokine signaling 1 (SOCS 1) have been previously described (Flodstrom et al., 2001; Gonzales at al., 2005, Hindinger et al., 2005). Overexpression of the dominant-negative form of IFNGR1 resulted in accelerated degradation of wild-type IFNGR1 and elimination of the IFN-γ cellular binding sites (Dighe et al., 1994). SOCS1 is an intracellular protein that blocks IFN-γ mediated Stat1 activation (i.e., phosphorylation) by Jak kinases (Starr et al., 1997; Song and Shuai 1998; Sakamoto et al., 2000; Yasukawa et al., 2000; Kubo et al., 2003; Stark et al., 1998; Levy and Darnell, 2002). Mouse mutants with a targeted null mutation in the SOCS1 gene exhibit abnormal hypersensitivity to IFN-γ and die of multi-organ failure in the presence of normal levels of the cytokine (Starr et al., 1998; Alexander et al., 1999; Bullen et al., 2001). Moreover, forced expression of SOCS 1 has been shown to result in a state of IFN-γ unresponsiveness in a variety of cell types (Tunley et al., 2001, 2002; Chong et al., 2001, Federici et al., 2002; Flodstom et al., 2001).

The PLP/SOCS1 mice exhibited no phenotypic or histological abnormalities, indicating that Stat1 activation is not required for normal oligodendrocyte development, even though its involvement in growth factor signaling has been suggested in vitro (Dell'Albani et al., 1998). Our finding is supported by the phenotypic characteristics of Stat1 (−/−) knockout mice, which displayed no oligodendrocyte or myelin abnormalities but do have significantly impaired IFN-γ cellular responses (Meraz et al., 1996). Thus, it appears that Stat1 activation plays a differential role in oligodendrocyte injury and development.

Functional examination of the PLP/SOCS1 mice further demonstrated a diminished oligodendrocyte-specific responsiveness to IFN-γ, including inhibition of Stat1 activation (i.e. phosphorylation) and nuclear translocation, and MHC class I molecule upregulation. When crossed with transgenic mice overexpressing IFN-γ in the CNS, PLP/SOCS1 mice were protected from the deleterious clinical and histological effects of IFN-γ. IFN-γ-overexpressing transgenic mice that also carried the PLP/SOCS1 transgene displayed significant oligodendrocyte and myelin preservation and lower prevalence of tremor compared to IFN-γ expressing mice without the PLP/SOCS1 transgene. Results of our study thereby indicate that IFN-γ exerts a direct injurious effect on developing oligodendrocytes.

Overexpression of SOCS1 provided cellular protection to oligodendrocytes, suggesting that inhibition of IFN-γ signaling results in reduced cellular effects. Wild-type oligodendrocytes, as reported by others and also observed by us, express nearly undetectable amounts of SOCS1 under normal, and even inflammatory conditions, and have much lower SOCS1 expression compared to the surrounding glial and inflammatory cells (Polizzotto et al., 2000; Wang and Campbell 2002; Maier et al., 2002). Such low constitutive expression may limit the oligodendrocyte capacity for effective downregulation of IFN-γ/Jak/Stat1 signaling, resulting in enhanced IFN-γ cellular effects. The rescuing effect of SOCS1 overexpression in oligodendrocytes that was observed in our experimental system supports this possibility.

Circumstantial and experimental evidence suggests that IFN-γ plays a deleterious role in the immune-mediated demyelinating disorder multiple sclerosis (Popko et al., 1997, Steinman 2001). IFN-γ is found in demyelinated lesions and its levels in cerebrospinal fluid correlate with disease severity (Vartanian et al., 1996; Calabresi et al., 1998; Becher et al., 1999; Moldovan et al., 2003). Administration of IFN-γ to MS patients exacerbated the disease, and neutralizing antibodies to IFN-γ have been shown to delay disease progression (Panitch et al, 1987; Skurkovich et al., 2001). Diminishing the local effect of IFN-γ, perhaps through the targeted expression of SOCS1 by oligodendrocytes, can be therapeutically beneficial. Remyelinating oligodendrocytes after a demyelinating insult are more sensitive to the presence of IFN-γ (Lin et al., in press); therefore, such protection might be particularly useful for the promotion of remyelination.

Stem cell therapy is rapidly gaining interest as a potential therapeutic approach to demyelinating disorders such as multiple sclerosis and adrenoleukodystrophy (review in Keirstead 2005). Stem cells engineered to be resistant to the harmful cytokines present in the extracellular milieu of the breached CNS is expected to stand a better chance of surviving and accomplishing remyelination. It is, therefore, of therapeutic interest to identify signaling pathways that play differential roles in oligodendrocyte injury and development. Our results describing inhibition of IFN-γ-mediated oligodendrocyte injury without induction of any observable oligodendrocyte or myelin abnormalities provide support for such an approach.

In summary, we have demonstrated that the forced expression of SOCS1 in oligodendrocytes of transgenic mice protects against the deleterious effects of IFN-γ on oligodendrocytes and the process of myelination. Our results strongly indicate that the deleterious effect of IFN-γ on myelinating oligodendrocytes is due, at least in part, to a direct adverse effect on these cells. Moreover, our work suggests that forced expression of SOCS1 in oligodendrocytes can provide protection against the harsh environment in immune-mediated demyelinating disorders.

REFERENCES

Agresti C, Bernardo A, Del Russo N, Marziali G, Battistini A, Aloisi F, Levi G, Coccia E (1998) Synergistic stimulation of MHC class I and IRF-1 gene expression by IFN-gamma and TNF-alpha in oligodendrocytes. Eur J Neurosci 10:2975-2983.

Agresti C, D'Urso D, Levi G (1996) Reversible inhibitory effects of interferon-gamma and tumor necrosis factor-alpha on oligodendroglial lineage cell proliferation and differentiation in vitro. Eur J Neurosci 8:1106-11016.

Alexander W. Starr R, Fenner J, Scott C, Handman E, Spring N, Corbin J, Cornish, A Darwishe R, Owczarek C, Kay T, Nicola N, Hertzog P, Metcalf D, Hilton D (1999) Socs1 is a critical inhibitor of interferon-gamma signaling and prevents the potentially fatal action of this cytokine. Cell 98:598-608.

Andrews T, Zhang P, Bhat N (1998) TNFalpha potentiates IFN gamma-induced cell death in oligodendrocyte progenitors. J Neurosci Res 54:574-583.

Becher B, Giacomini P S, Pelletier D, McCrea E, Prat A, Antel J (1999) Interferon-gamma secretion by peripheral blood T-cell subsets in multiple sclerosis: correlation with disease phase and interferon-beta therapy. Ann Neurol 45:247-250.

Baerwald K, Popko B (1998) Developing and mature oligodendrocytes respond differently to the immune cytokine interferon-gamma. J Neurosci Res 52:230-239.

Baerwald K, Corbin J, Popko B (2000) Major histocompatibility complex heavy chain accumulation in the endoplasmic reticulum of oligodendrocytes results in myelin abnormalities. J Neurosci Res 15:160-169.

Billiau A (1996) Interferon-γ: biology and role in pathogenesis. Adv Immunol 62:61-130.

Bullen D, Darwich R, Metcalf D, Handman E, Alexander W (2001) Neutralization of interferon-gamma in neonatal SOCS1−/− mice prevents fatty degeneration of the liver but not subsequent inflammatory disease. Immunol 2001, 104:92-98.

Calabresi P, Tranquill L, McFarland H, Cowan E (1998) Cytokine gene expression in cells derived from CSF of multiple sclerosis patients. J Neuroimmunol 14:198-205.

Chew L., King W., Kenedy A, Gallo V (2005) Interferon-gamma inhibits cell cycle exit in differentiating oligodendrocyte progenitor cells. Glia 52:127-143.

Chong M, Thomas H, Kay T (2001) gamma-Interferon signaling in pancreatic beta-cells is persistent but can be terminated by overexpression of suppressor of cytokine signaling-1. Diabetes 50:2744-2751.

Corbin J, Kelly D, Rath E, Baerwald K, Suzuki K, Popko B (1996) Targeted CNS expression of interferon-gamma in transgenic mice leads to hypomyelination, reactive gliosis, and abnormal cerebellar development. Mol Cell Neurosci 7:354-370.

Dell'Albani, Kahn M, Cole R, Condorelli D, Giuffrida-Stela A, Vellis J (1998) Oligodendrocyte survival factors, PFGF-AA and CNTF, activate Jak/STAT signaling pathways. J Neurosci Res 54:191-205.

Dighe A, Richards E, Old L, Schreiber R (1994) Enhanced in vivo growth and resistance to rejection of tumor cells expressing dominant negative IFN gamma receptors. Immunity 1:447-456.

Doerflinger N, Macklin W, Popko B (2003) Inducible site-specific recombination in myelinating cells. Genesis 35:63-72.

Einhauer A, Jungbauer A (2001) The flag peptide, a versatile fusion tag for the purification of recombinant proteins. J Biochem Biophys 49:455-465.

Federici M, Giustiziri M, Scarponi C, Girolomini G, Albanesi C (2002) Impaired IFN-gamma-dependent inflammatory response in human keratinocytes overexpressing the suppressor of cytokine signaling 1. J Immunol 169:434-443.

Flodstrom M, Maday A, Balakrisha D, Cleary M, Yoshimura A, Starvetnick N (2001) Target cell defense prevents development of diabetes after viral infection. Nat Immunol 3:373-382.

Fuss B, Mallon B, Phan T, Ohlemeyer C, Kirchoff F, Nishiyama A, Macklin W (2000) Purification and analysis of in vivo-differentiated oligodendrocytes expressing the green fluorescent protein. Dev Biol 218:259-274.

Gao X, Gilling T, Ye P, D'Ercole J, Matsushima G, Popko B (2000) Interferon-γ protects against cuprizone-induced demyelination. Mol Cell Neurosci 16:338-349.

Gao X, Kemper A, Popko B (1999) Advanced transgenic and gene-targeting approachs. Neurochem Res 24:1183-1190.

Glabinski A, Kranowski M, Han Y, Owens T, Ransohoff R (1999) Chemokine expression in GRO mice (lacking interferon-gamma) with experimental autoimmune encephalomyelitis. J Neurovirol 51:95-101.

Gonzales J, Bergmann C, Fuss B, Hinton D, Kangas C, Macklin W, Stohhnan S (2005) Expression of dominant negative IFN-γ receptor on mouse oligodendrocytes. Glia 51:22-34.

Hindinger C, Gonzalez J, Bergmann C, Fuss B, Hinton D, Atkinson R, Macklin W, Stohlman S (2005) Astrocyte expression of a dominant-negative interferon-gamma receptor. J Neurosci Res 82:20-31.

Horwitz M, Evans C, McGavem D, Rodriguez M, Oldstone M (1997) Primary demyelination in transgenic mice expressing interferon-gamma. Nature Med 3:1037-1041.

Keirstead H (2005) Stem cells for the treatment of myelin loss. Trends Neurosci 28:677-683.

Kubo M, Hanada T, Yoshimura A (2003) Suppressors of cytokine signaling and immunity. Nature Immunol 4:1169-1176.

LaFerla F, Sugarman M, Lane T, Leissring M (2000) Regional dysplasia in transgenic mice with astrocyte-derived expression of interferon-gamma. J Mol Neurosci 15:45-59.

Levy D, Darnell J (2002) Stats: transcriptional control and biological impact. Nature Rev Mol Cell Biol 651-662.

Lin W, Kemper A, McCarthy K, Pytel P Wang J, Campbell I, Utset M, Popko B (2004) Interferon-gamma induces medullobalstoma in the developing cerebellum. J Neurosci 24:10074-10083.

Lin W, Harding H, Ron D, Popko B (2005) Endoplasmic reticulum stress modulates the response of myelinating oligodendrocytes to the immune cytokine interferon-gamma. J Cell Biol 169:603-612.

Lin W, Kemper A, Dupree J, Harding H, Ron D, Popko B. Interferon-gamma inhibits central nervous system remyelination through a process modulated by endoplasmic reticulum stress. Brain (in press).

Loughlin A, Copelman C, Hall A, Armer T, Young B, Landon D, Cuzner M (1997) Myelination and remyelination of aggregate rat brain cell cultures enriched with macrophages. J Neurosci Res 47:384-392.

Maier J, Kincaid C, Pagenstecher A, Campbell I (2002) Regulation of signal transducer and activator of transcription and suppressor of cytokine-signaling gene expression in the brain of mice with astrocyte-targeted production of interleukin-12 or experimental autoimmune encephalomyelitis. Am J Pathol 160:271-288.

Merrill J, Zimmerman R (1991) Natural and induced cytotoxicity of oligodendrocytes by microglia is inhibitable by TGF beta. Glia 4:327-31.

Merrill J, Ignarro L, Sherman M, Melinek J, Lane T (1993) Microglial cytotoxicity of oligodendrocytes is mediated through nitric oxide. J Immunol 151:2132-2141.

Meraz M, White J, Sheehan K, Bach E, Roding S, Dighe A, Kaplan D, Riley J, Greenlund A, Campbell D, Caver-Moore K, Dubois R, Clark R, Aguet M, Schreiber R (1996) Targeted disruption of Stat1 gene in mice reveals unexpected physiological specificity in the Jak/STAT signaling pathway. Cell 84:431-442.

Moldovan I R, Rudick R A, Cotleur A C, Born S E, Lee J C, Karafa M T, Pelfrey C M (2003) Interferon gamma responses to myelin peptides in multiple sclerosis correlate with a new clinical measure of disease progression. J Neuroimmunol 141:132-140.

Panitch N, Hirsch R, Haley A, Johnson K (1987) Exacerbations of multiple sclerosis in patients treated with gamma interferon. Lancet 1:893-895.

Polizzotto M, Bartlett P, Turnley A (2000) Expression of "suppressor of cytokine signaling" (SOCS) genes in the developing and adult mouse nervous system. J Compar Neurol 423:348-358.

Popko B, Corbin J, Baerwald K, Dupree J, Garcia A (1997) The effects of interferon-gamma on the central nervous system. Mol Neurobiol 14:19-35.

Pouly S, Becher B, Blain M, Antel J (2000) Interferon-gamma modulates human oligodendrocyte susceptibility to Fas-mediated injury. J Neuropathol Exp Neurol 59:280-286.

Sakamoto H, Kinjyo I, Yoshimura A (2000) The janus kinase inhibitor, Jab/SOCS1, is an interferon-gamma inducible gene and determines sensitivity to interferons. Leuk Lymphoma 38:49-58.

Skurkovich S, Boiko A, Beliaeva I, Buglak I, Alekseeva T, Smirnova T, Kulakova O, Tchechonin V, Gurova O, Deomina T, Favarova O, Skurkovith B, Gusev E (2001) Randomized study of antibodies to IFN-gamma and TNF-alpha in secondary progressive multiple sclerosis. Mult Scler 7:277-284.

Song M, Shuai K (1998) The suppressor of cytokine signaling (SOCS1) and SOCS3 but not SOCS2 proteins inhibit interferon-mediated antiviral and antiproliferative activities. J Biol Chem 25:35056-35062.

Steiman L (2001) Blockade of gamma interferon might be beneficial in MS. Mult Scler 7:275-276.

Stark G, Kerr I, Williams B, Silverman R, Schreiber R (1998) How cells respond to interferons. Ann Rev Biochem 67:257-264.

Starr R, Wilson T, Viney E, Murray L, Rayner J, Jenkins J, Brendan J, Gonda T, Alexander W, Metcalf D, Nicola N, Hilton J (1997) A family of cytokine inducible inhibitors of signaling. Nature 387:917-921.

Starr R. Donald M, Elefanty A, Brysha, M, Wilson T, Nicola A, Hilton D, Alexander W (1998) Liver degeneration and lymphoid deficiency in mice lacking suppressor of cytokine signaling-1. PNAS USA 95:14395:14999.

Torres C, Aranguez I, Rubio N (1995) Expression of interferon-gamma receptors on murine oligodendrocytes and its regulation by cytokines and mitogens. Immunology 86:250-255.

Tran E, Prince E, Owens T (2000) IFN-gamma shapes invasion of the central nervous system via regulation of chemokines. J Immunol 164:2759-2768.

Traugott U (2001) Evidence for immunopathogenesis. In: Handbook of Multiple sclerosis (Cook S, ed) 3d edition, pp 163-192, New York: Marcel Deker.

Tunley A, Starr R, Bartlett P (2002) Failure of sensory neurons to express class I MHC is due to differential SOCS1 expression. J Neuroimmunol 123:35-40.

Tunley A, Starr R, Bartlett P (2001) SOCS 1 regulates interferon-gamma mediated sensory neuron survival. Neuroreport 16:3443-3445.

Vartanian T, Li Y, Zhao M, Stefansson K (1995) Interferon-γ induced oligodendrocyte cell death: implications for the pathogenesis of multiple sclerosis. Mol Med 1:732-743.

Wang J, Campbell I (2002) Cytokine signaling in the brain: putting a SOCS in it? J Neurosci Res 67:423-427.

Wight P, Duchala C, Readhead C, Macklin W (1993) A myelin proteolipid protein-lacZ fusion protein is developmentally regulated and targeted to the myelin membrane in transgenic mice. J Cell Biol 123:443-454.

Yasukawa H, Sasaki A, Yoshimura A (2000) Negative regulation of signaling pathways. Annu Rev Immunol 18:143-164.

The invention claimed is:

1. A method of reducing neuronal demyelination comprising administering to a myelinating cell an effective amount of a small molecule, wherein said small molecule reduces neuronal demyelination when administered to a transgenic mouse whose genome comprises:
   (a) a stably integrated transgenic nucleotide sequence encoding interferon-gamma (IFN-γ) operably linked to an inducible promoter; and
   (b) a heterozygous knock-out of the endogenous pancreatic endoplasmic reticulum (ER) kinase gene (PERK), wherein upon expression of said IFN-γ, said transgenic mouse exhibits a greater degree of demyelination relative to a transgenic mouse having a stably integrated transgenic nucleotide sequence encoding IFN-γ as in (a), but lacking said heterozygous knock-out of the PERK gene,
   wherein said small molecule is characterized in that upon said administration and upon said expression of said IFN-γ in said transgenic mouse neuronal demyelination is reduced, and wherein said small molecule is effective to decrease growth and DNA damage protein 34 (GADD34) activity or increase pancreatic ER kinase (PERK) activity, resulting in an increase of phosphorylated eukaryotic translation initiation factor 2 alpha (p-eIF-2α) inside said myelinating cell.

2. The method of claim 1, wherein said small molecule is effective to reduce a sustained stress level of endoplasmic reticulum (ER) in a myelinating cell.

3. The method of claim 1, wherein said small molecule is an interferon-gamma (INF-γ) antagonist.

4. The method of claim 1, wherein said small molecule is an interferon-gamma (INF-γ) agonist administered prior to the onset of neuronal demyelination to yield a prophylactic effect.

5. The method of claim 1, wherein said myelinating cell is located in a subject's central nervous system or peripheral nervous system.

6. The method of claim 1, wherein said myelinating cell is from a subject suffering from multiple sclerosis.

7. The method of claim 1, wherein said myelinating cell is from a subject suffering from a neuronal demyelination inflicted by a pathogen or virus.

8. The method of claim of 1, wherein said neuronal demyelination is inflicted by an inflammatory agent.

9. The method of claim 1, wherein said small molecule is salubrinal.

10. The method of claim 1, wherein said reduction of neuronal demyelination when said small molecule is administered to said transgenic mouse comprises a reduction in the loss of oligodendrocytes or Schwann cells in the nervous system of said mouse.

11. The method of claim 10, wherein said reduction in the loss of oligodendrocytes or Schwann cells in the nervous system of said mouse when said small molecule is administered to said transgenic mouse is determined by characterizing a reduction in the level of an oligodendrocyte marker or a Schwann cell marker.

12. The method of claim 11, wherein said oligodendrocyte marker is proteolipid protein (PLP).

13. The method of claim 1, wherein said reduction of neuronal demyelination when said small molecule is administered to the transgenic mouse comprises an increase in myelinated axons in the nervous system of said mouse.

14. The method of claim 1, wherein said small molecule inhibits protein phosphatase-1-growth and DNA damage protein 34 (PP1-GADD34) phosphatase activity in said myelinating cell.

* * * * *

SEQUENCE LISTING

<160> NUMBER OF SEQ ID NOS: 57

<210> SEQ ID NO 1

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attccccaaa ggcccatgt                                                19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtctccacaa gctccatgtc c                                             21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tgctgggccc tgggcttcta cc                                            22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctccctgcc ccagaagt                                                 18

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtcacaatg ttcttgaaga aatgg                                         25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
agcacggccg gacccaagat g                                             21

<210> SEQ ID NO 7
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 7
cacttacaac ttcgccgtcc t                                              21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggagtttct atgggagctc aga                                            23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
aactcatggg ccgaggcacc aa                                             22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttatcggaaa ttcacaagga tcaa                                           24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggcgaagaa tgtagtctat ccaata                                         26

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ccggccaccc tgtcaatcgg                                                20

<210> SEQ ID NO 13
<211> LENGTH: 20
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 13
ggcaggttct gtccctttca                                                 20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accgcctgga gttctgga                                                   18

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cccaaggcgc cacatctccc t                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctacagcgga agcacagcag                                                 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atttgaaggt gagcatcctg gg                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
agcagcagca gcagcagcag ca                                              22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
ctctatggtc agcgttccaa ca                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaggtagcg tgattgacac at                                              22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
cctcaccctc ggcatccagc agc                                             23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atgctgttgc tgctgctgag                                                 20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttggacacg ctgagctttg ag                                              22

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cgctgctgcc ttcactgtag ccgc                                            24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```
cttctccgtt ccaagatcct tcg                                             23

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcactaagg gctcagtcag a                                               21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
tgctgctccg tgggcaaaga ccc                                             23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctgggctgt acaaaccttc c                                               21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttgaggtcta aaggctccgg                                                 20

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tgtccgaagc aaacatcaca ttcagatcc                                       29

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
actccggcgt gaggtagaaa                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agagcggaac aggtccatgt                                               20

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ttctcagaga cccttactcg ggccaaatt                                     29

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccaccacacc tgaaagcaga a                                             21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aggtgccccc aatttcatct                                               20

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tgagtccctg cctttcacct tggaga                                        26

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgctgacag ctcctcatgg a                                             21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
tgagagccag acgtgttcgt                                              20

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gatatctcga ggaactggca aaa                                          23

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
cttcaaagag tctgaggtag aaagagataa t                                 31

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
ccaggacgac gatgacaaga                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42 tcagggggtcc ccaatagaag                                             20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
atgaggaaga gctgcaaagc                                              20

<210> SEQ ID NO 44
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtgacagac tccaagcaca                                              20

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tcgctttcct ctgaacgctt ctcg                                         24

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctgaacgct gtgacttgga gtgtcc                                       26

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgaattcgag ctcggtaccc                                              20

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccatcctttg ccattcctcc ag                                           22

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gatgacaaga cgcgccagat g                                            21

<210> SEQ ID NO 50
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 50
gaggacgagg agggctctga                                                    20

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
cgcacccagc tggcagccga catt                                               24

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gatatctcga ggaactggca aaa                                                23

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctacaaagag tctgaggtag aaagagataa t                                       31

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
tggtgacatg aaaatcctgc agagcca                                            27

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctcaactaca tggtctacat gttcca                                             26

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 56
ccattctcgg ccttgactgt                                                 20

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
tgactccact cacggcaaat tcaacg                                          26
```